(12) United States Patent
Schwartz et al.

(10) Patent No.: US 10,335,495 B2
(45) Date of Patent: Jul. 2, 2019

(54) BIOMOLECULE CONJUGATES

(71) Applicant: CELGENE CORPORATION, Summit, NJ (US)

(72) Inventors: Eric Schwartz, Lynnfield, MA (US); Laura Akullian D'Agostino, Sudbury, MA (US); Hernan Cuervo, Arlington, MA (US); Wesley Austin, Cambridge, MA (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 15/532,255

(22) PCT Filed: Dec. 3, 2015

(86) PCT No.: PCT/US2015/063774
§ 371 (c)(1),
(2) Date: Jun. 1, 2017

(87) PCT Pub. No.: WO2016/090157
PCT Pub. Date: Jun. 9, 2016

(65) Prior Publication Data
US 2017/0360952 A1 Dec. 21, 2017

Related U.S. Application Data

(60) Provisional application No. 62/087,369, filed on Dec. 4, 2014.

(51) Int. Cl.
*A61K 31/5365* (2006.01)
*A61K 47/68* (2017.01)
*A61K 47/54* (2017.01)
*A61K 47/60* (2017.01)

(52) U.S. Cl.
CPC ...... *A61K 47/6803* (2017.08); *A61K 31/5365* (2013.01); *A61K 47/545* (2017.08); *A61K 47/60* (2017.08); *A61K 47/6835* (2017.08); *A61K 47/6889* (2017.08)

(58) Field of Classification Search
CPC .. A61K 31/5365; A61K 47/48; A61K 47/545; A61K 47/60; A61K 47/6803; A61K 47/6835; A61K 47/6889
See application file for complete search history.

(56) References Cited

FOREIGN PATENT DOCUMENTS

WO  WO 2014/004639  *  1/2014
WO  WO 2014/065661  *  5/2014

* cited by examiner

*Primary Examiner* — Deepak R Rao
(74) *Attorney, Agent, or Firm* — Eckert Seamans Cherin & Mellott, LLC

(57) ABSTRACT

The present invention relates to biomolecule conjugates which comprise a biomolecule wherein at least one non-natural amino acid (NNAA) is integral to the structure of the biomolecule and wherein the NNAA is a point of attachment of a linker to which a payload, particularly a cytotoxic agent, is attached. More specifically, this invention relates to conjugates of cell-binding agents and active release products comprising cytotoxic agents wherein the conjugates are produced by means of a cycloaddition reaction. Methods of production, pharmaceutical compositions and methods of use are provided.

16 Claims, 27 Drawing Sheets

BIOMOLECULE CONJUGATES

CROSS-REFERENCE TO RELATED APPLICATIONS

This present application is a U.S. National Phase of International Application No. PCT/US2015/063774, filed Dec. 3, 2015, which claims priority to U.S. Provisional Patent Application No. 62/087,369, filed Dec. 4, 2014, which are incorporated herein by reference in their entirety.

FIELD OF THE INVENTION

The present invention relates to biomolecule conjugates which comprise a biomolecule wherein at least one non-natural amino acid (NNAA) is integral to the structure of the biomolecule and wherein the NNAA is a point of attachment of a linker to which a payload, particularly a cytotoxic agent, is attached. This invention further relates to conjugates of cell-binding agents and cytotoxic agents wherein the conjugates are produced by means of a cycloaddition reaction. Methods of production, pharmaceutical compositions and methods of use are provided.

BACKGROUND OF THE INVENTION

Next-generation antibody (NGA) therapeutics with antibody architecture modifications represent a key area of monoclonal antibody (mAb) research and development. Oncology is the main focus, with about 50% of the oncology mAb pipeline consisting of NGAs. Syed, B. A., et al., *Next-Generation Antibodies*, Nature Reviews Drug Discovery, 13:413 (2014).

Antibody-drug conjugates (ADCs), the most prominent of the new antibody technology platforms, generally comprise a cytotoxic agent attached to a mAb via chemical linkers. By offering targeted delivery of chemotherapeutic agents directly to the cancerous tissue, ADCs may increase the clinical efficacy of mAbs and enable the deployment of cytotoxins that are too potent for systemic administration. The first ADC product, gemtuzumab ozogamicin (MYLOTARG®; Wyeth), a calicheamicin-linked CD33-specific mAb for the treatment of acute myeloid leukaemia (AML), was approved in 2000 but withdrawn in 2010 over safety concerns. New platforms for ADC development, such as the targeted antibody payload platform (TAP; Seattle Genetics and ImmunoGen), have emerged. In late 2011, brentuximab vedotin (ADCETRIS®; Seattle Genetics), a CD30-specific mAb linked to the antimitotic agent monomethyl auristatin E (MMAE) for the treatment of non-Hodgkin's lymphoma (NHL), became the first of the new ADCs to gain approval from the US Food and Drug Administration (FDA). The second approval was ado-trastuzumab-emtansine (KADCYLA®; Genentech/Roche) in early 2013. Ado-trastuzumab-emtansine and the mAb pertuzumab (PERJETA®; Roche (approved in 2012)) were developed as line-extensions of trastuzumab (HERCEPTIN®; Roche), targeting HER2 (also known as ERBB2) with different modes of action; PERJETA® inhibits HER2-HER3 dimerization whereas ado-trastuzumab-emtansine delivers a cytotoxic payload to the cells.

Cytotoxic molecules, radionuclides, and certain chemotherapeutic drugs have been chemically linked to monoclonal antibodies that bind tumor-specific or tumor-associated cell surface antigens. See, e.g., International (PCT) Patent Application Nos. WO 00/02587, WO 02/060955, WO 02/092127; and, U.S. Pat. Nos. 8,198,417, 8,012,485, 5,475,092, 6,340,701, and 6,171,586.

Existing mAb development processes routinely make use of techniques such as hinge engineering and affinity maturation. However, a challenge remains to improve the efficacy and minimize the undesirable side effects of immunoconjugate therapy.

SUMMARY OF THE INVENTION

The present invention is directed to isolated biomolecule conjugates and to isolated biomolecule conjugates prepared by means of cycloaddition reactions described herein.

The current invention is also directed to methods of preparing isolated biomolecule conjugates by means of cycloaddition comprising

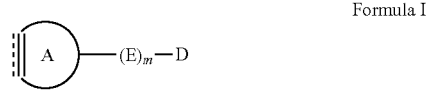

Formula I providing a compound of Formula I is provided which comprises a cyclic strained alkyne or alkene, (A) attached to a linker (spacer arm), $((E)_m)$, and wherein a payload (D), is also attached to the linker; and,

Formula II providing a compound of Formula II is provided, a biomolecule (CB), comprising at least one non-naturally occurring amino acid (NNAA) (M) integral to its structure wherein the NNAA exhibits an azide (azido-pheylalanine or azido-para-methyl-phenylalanine, for example) or a tetrazine group (T); and, reacting the compound of Formula I with the compound of Formula II to produce a compound (biomolecule conjugate) of Formula III, Formula III' or Formula III"

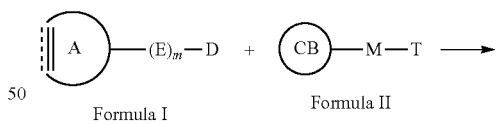

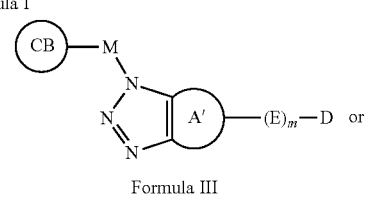

Formula III

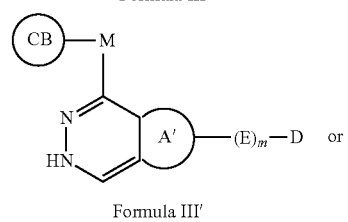

Formula III'

-continued

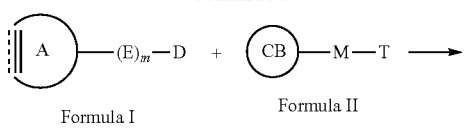
Formula I    Formula II

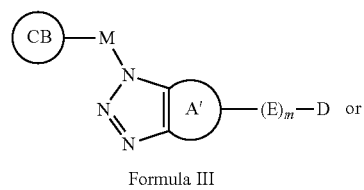
Formula III

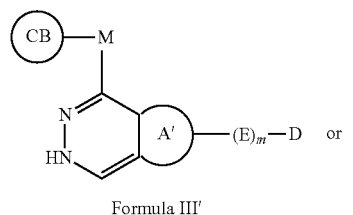
Formula III'

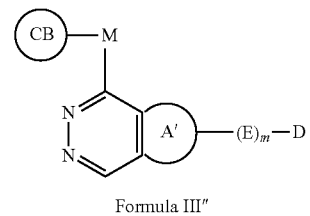
Formula III''

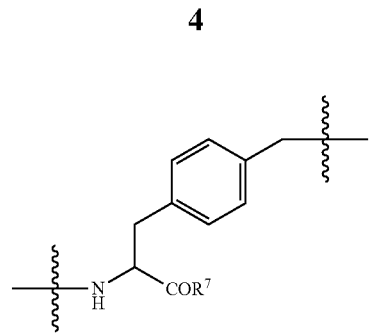
V

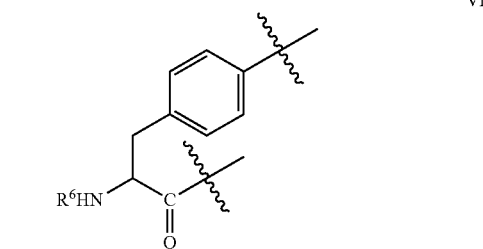
VI

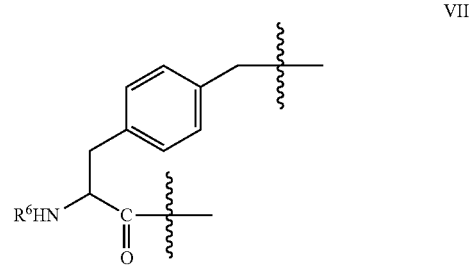
VII

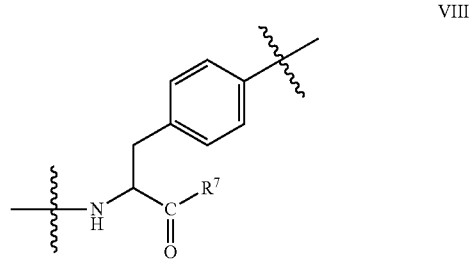
VIII

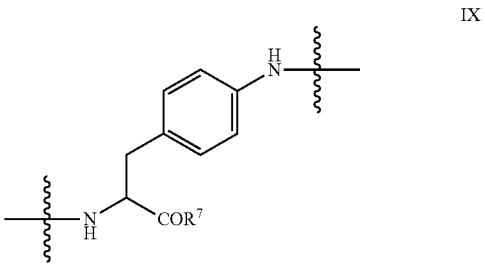
IX

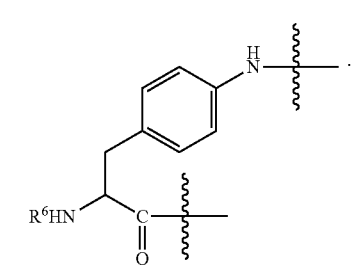
X

The invention is further directed to isolated biomolecule conjugates of Formula III, III', or III'' prepared by means of cycloaddition reactions described herein wherein the biomolecule conjugates comprise at least one non-naturally occurring amino acid (NNAA) (M) integral to the biomolecule

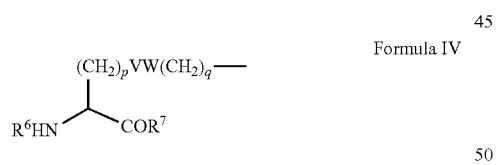
Formula IV wherein p and q are each an integer from 0-10;

$R^6$ is is H, an amino acid within a polypeptide, or a bond;

$R^7$ is OH, an amino acid within a polypeptide, or a bond;

V is an alkyl or aryl carbocycle, heterocycle, or absent; and,

W is O, N, S, or absent.

The invention is accordingly further directed to isolated biomolecule conjugates of Formula III, III' (or III'' (III'' shall also be considered within the scope throughout this disclosure)) prepared by means of cycloaddition reactions described herein wherein the biomolecule conjugates comprise at least one non-naturally occurring amino acid (NNAA) (M) integral to the biomolecule structure selected from the group consisting essentially of formulae In addition, the current invention is directed to isolated biomolecule conjugates of Formula III or III' prepared by means of cycloaddition reactions described herein wherein the biomolecule conjugates comprise at least one payload (D) which is a cytotoxic agent.

The invention is accordingly further directed to isolated biomolecule conjugates of Formula III or III' prepared by means of cycloaddition reactions described herein wherein the biomolecule conjugates comprise at least one maytansinoid as a payload (D).

The invention is accordingly further directed to isolated biomolecule conjugates of Formula III or III' prepared by means of cycloaddition reactions described herein wherein the biomolecule conjugates comprise at least one cytotoxic agent as a payload (D) of the structure

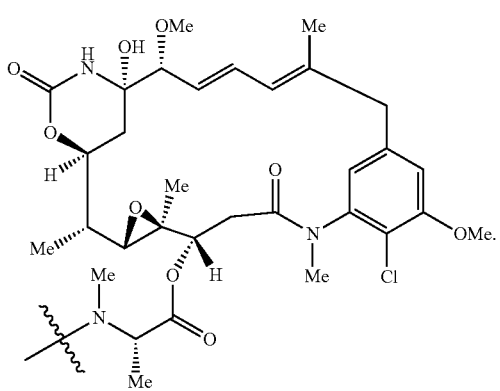

C1

The invention is further directed to pharmaceutical compositions which comprise a therapeutically effective amount of a biomolecule conjugate described herein and a pharmaceutically-acceptable carrier.

The invention is further directed to a method of treatment of an abnormal physiological condition in a mammal comprising administering an effective amount of a biomolecule conjugate described herein.

The invention is accordingly further directed to a method of treatment of a cell proliferative disorder in a mammal comprising administering an effective amount of a biomolecule conjugate described herein.

The invention is accordingly further directed to a method of treatment of a hematological oncology disorder in a mammal comprising administering an effective amount of a biomolecule conjugate described herein.

The current invention is also directed to an isolated compound

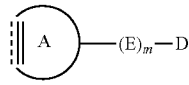

Formula I wherein A is a strained alkyne or alkene ring, wherein the ring is carbocyclyl or heterocyclyl, D is a payload;

Each E is independently selected from the group consisting of —CO—, —CR$^1$R$^2$—, —NR$^3$—, —S—S—, —S—, —SO—, —SO$_2$—, —O—, —CR$^3$=N—NR$^3$—, —CR$^3$=N—O—, —CR$^3$=N—NR$^3$—CO—, —N=N—CO—, alkyl, C3-C8 carbocyclyl, —O—(CR$^1$R$^2$)$_a$—, aryl, —(CR$^1$R$^2$)$_a$-aryl, heteroaryl, —(CR$^1$R$^2$)$_a$-heteroaryl, —(CR$^1$R$^2$)$_a$—C3-C8 carbocyclyl, heterocyclyl, —(CR$^1$R$^2$)$_a$-heterocyclyl, —(CH$_2$CH$_2$O)$_a$—, —(CH$_2$CH$_2$O)$_a$—(CH$_2$)$_b$-, —(CH$_2$)$_a$C(O)—, amino acid, and peptide;

R$^1$ and R$^2$ are each independently selected from the group consisting of H, F, Cl, Br, I, OH, —N(R$^3$)$_2$, —N(R$^3$)$_3^+$, C1-C8 alkylhalide, carboxylate, sulfate, sulfamate, sulfonate, —SO$_2$R$^3$, —S(=O)R$^3$, —SR$^3$, —SO$_2$N(R$^3$)$_2$, —C(=O)R$^3$, —CO$_2$R$^3$, —C(=O)N(R$^3$)$_2$, —CN, —N$_3$, —NO$_2$, C1-C8 alkoxy, polyethyleneoxy, phosphonate, phosphate, C1-C8 alkyl, C2-C8 alkenyl, C2-C8 alkynyl, aryl, heteroaryl, C3-C8 carbocyclyl, and C1-C20 heterocyclyl; or, when taken together, R$^1$ and R$^2$ form a carbonyl (=O), or spiro carbocyclic ring of 3 to 7 carbon atoms; and, R$^3$ is selected from the group consisting of H, C1-C8 alkyl, C2-C8 alkenyl, C2-C8 alkynyl, C6-C20 aryl, C5-C20 heteroaryl, C3-C8 carbocyclyl, and C1-C20 heterocyclyl;

alkyl, alkenyl, alkynyl, aryl, heteroaryl, carbocyclyl, and heterocyclyl are optionally independently substituted with one or more substituents selected from the group consisting of F, Cl, Br, I, OH, —N(R$^3$)$_2$, —N(R$^3$)$_3^+$, C1-C8 alkylhalide, carboxylate, sulfate, sulfamate, sulfonate, C1-C8 alkylsulfonate, C1-C8 alkylamino, 4-dialkylaminopyridinium, C1-C8 alkylhydroxyl, C1-C8 alkylthiol, —SO$_2$R, —S(=O)R$^3$, —SR$^3$, —SO$_2$N(R$^3$)$_2$, —C(=O)R$^3$, —CO$_2$R$^3$, —C(=O)N(R$^3$)$_2$, —CN, —N$_3$, —NO$_2$, C1-C8 alkoxy, C1-C8 trifluoroalkyl, C1-C8 alkyl, C3-C12 carbocycle, C6-C20 aryl, C6-C20 heteroaryl, C3-C8 carbocyclyl, C2-C20 heterocyclyl, polyethyleneoxy, phosphonate, and phosphate;

m is an integer from 1 to 100; and, a and b are each an integer from 1 to 100.

The current invention is further directed to an isolated compound of Formula I wherein each E is independently selected from the group consisting of —(CH$_2$CH$_2$O)$_a$—, —(CH$_2$)$_a$C(O)NR$^3$—, —(CH$_2$)$_a$NR$^3$C(O)—, —(CH$_2$)$_a$C(O)NR$^3$(CH$_2$)$_b$—, —(CH$_2$)$_a$C(O)NR$^3$(CH$_2$CH$_2$O)$_b$—, —(CH$_2$)$_a$C(O)NR$^3$(CH$_2$CH$_2$O)$_b$(CH$_2$)$_c$—, —(CH$_2$CH$_2$O)$_a$C(O)NR$^3$(CH$_2$CH$_2$O)$_b$—, —(CH$_2$CH$_2$O)$_a$C(O)NR$^3$(CH$_2$CH$_2$O)$_b$, —(CH$_2$CH$_2$O)$_a$C(O)NR$^3$(CH$_2$)$_b$—, —(CH$_2$CH$_2$O)$_a$—(CH$_2$)$_b$, —(CH$_2$)$_a$C(O)—, —CR$^3$=N—NR$^3$—, —CR$^3$=N—O—, —CR$^3$=N—NR$^3$—CO—, —N=N—CO—, —S—, —SO—, —SO$_2$—, amino acid, dipeptide, tripeptide;

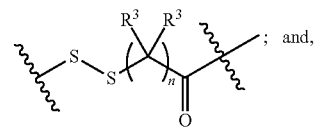

E1

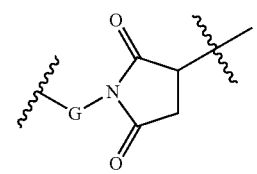

E2 wherein G is selected from the group consisting of alkyl, aryl, carbocyclyl, and heterocyclyl; and,

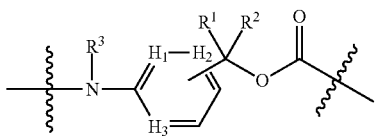

G1 wherein $H_1$, $H_2$, and $H_3$ are each independently selected from N or $CR^1$.

The current invention is further directed to an isolated compound of Formula I wherein each E is independently selected from the group consisting of wherein:

J is an amino acid or peptide;

d, e, g, i, j, and k are each independently an integer from 1 to 30;

h is an integer from 0 to 30;

$R^3$ is defined as above;

Each $R^4$ is independently selected from the group consisting of H, alkyl, $-N(R^3)_2$, $-SR^3$, and C1-C8 alkoxy, aryl; and, $R^5$ is selected from the group consisting of H, $-N(R^3)_2$, $-SR^3$, C1-C8 alkoxy, aryl, and $NO_2$.

The invention is further directed to each of the following exemplary isolated compounds of Formula I as well as analogs and derivatives thereof
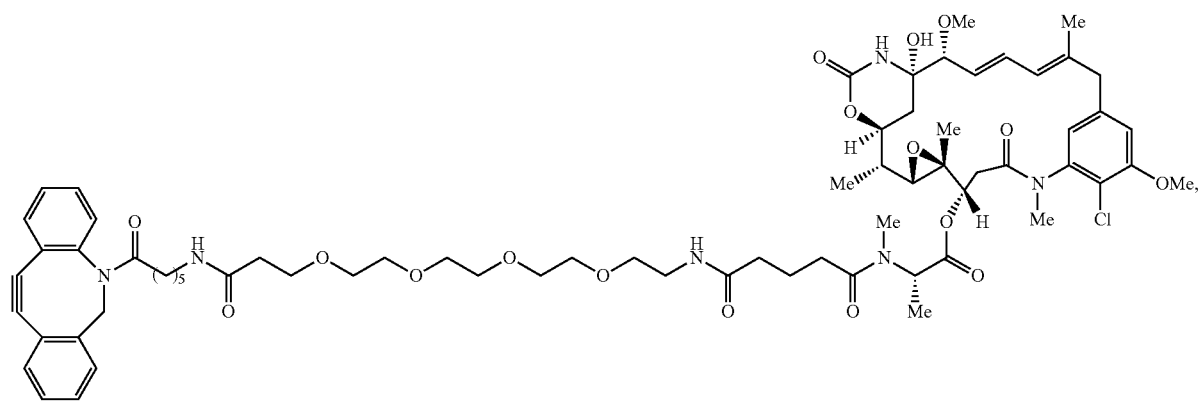
I1
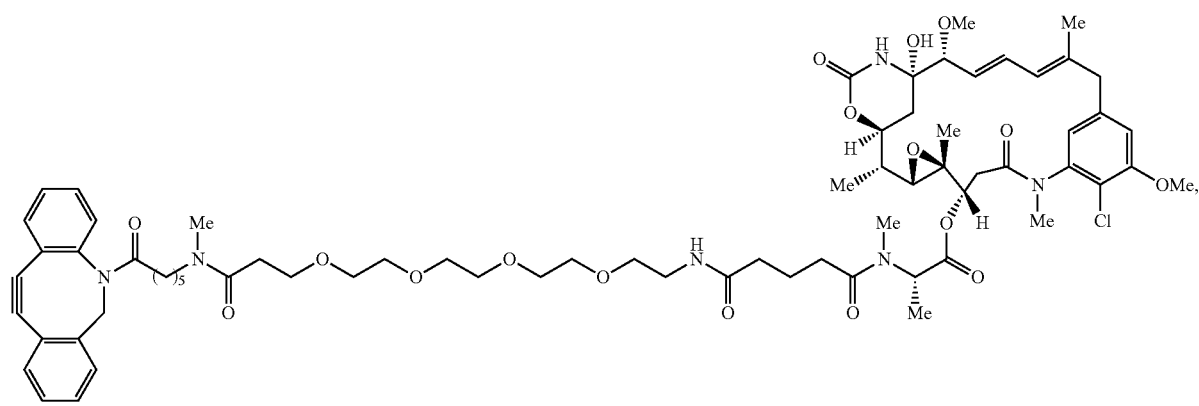
I2
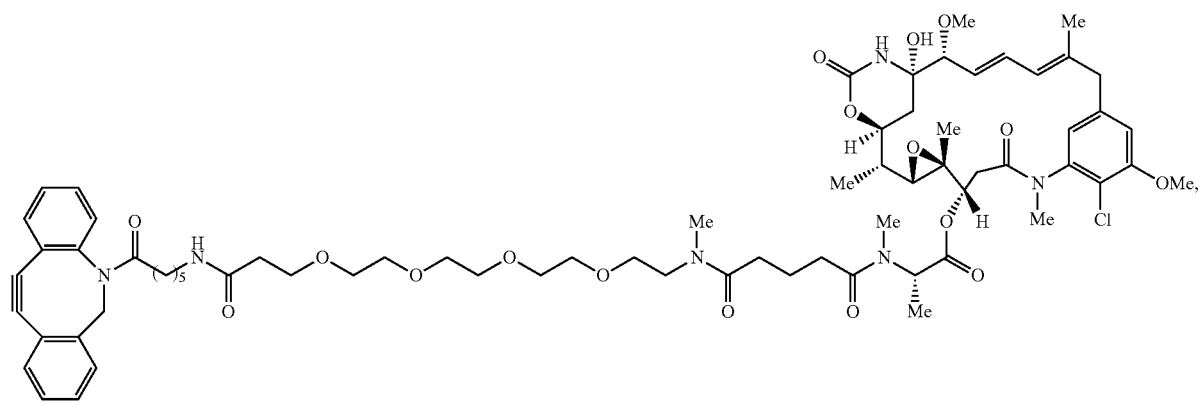
I3

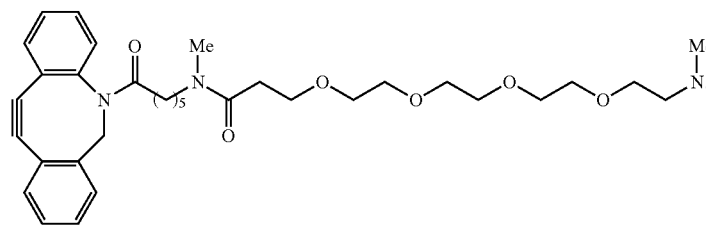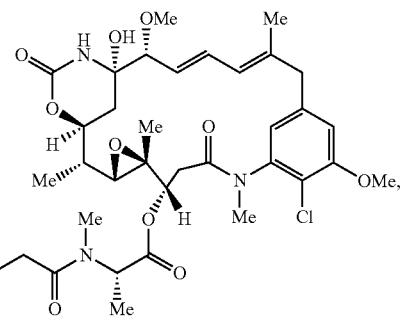
I4
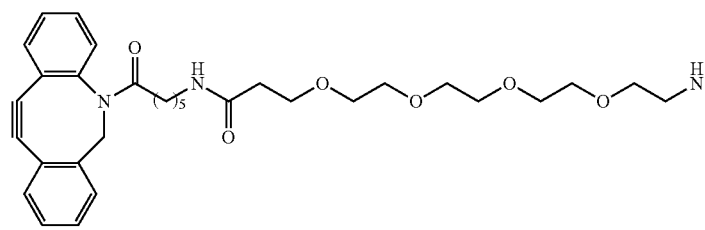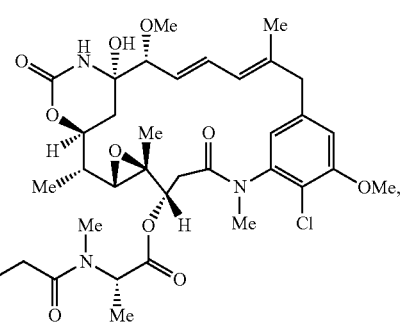
I5
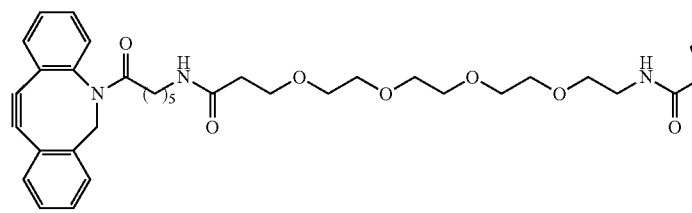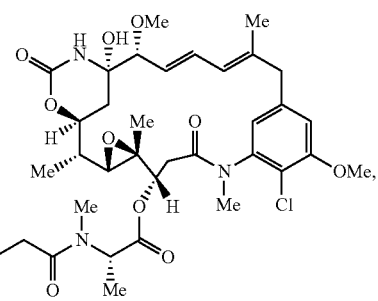
I6
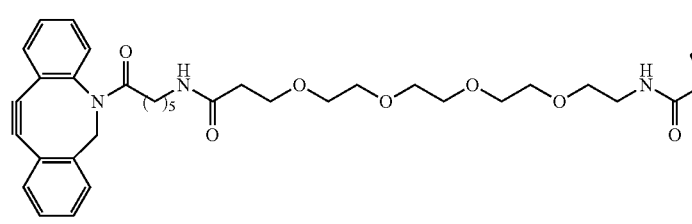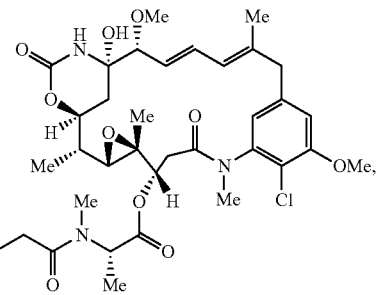
I7

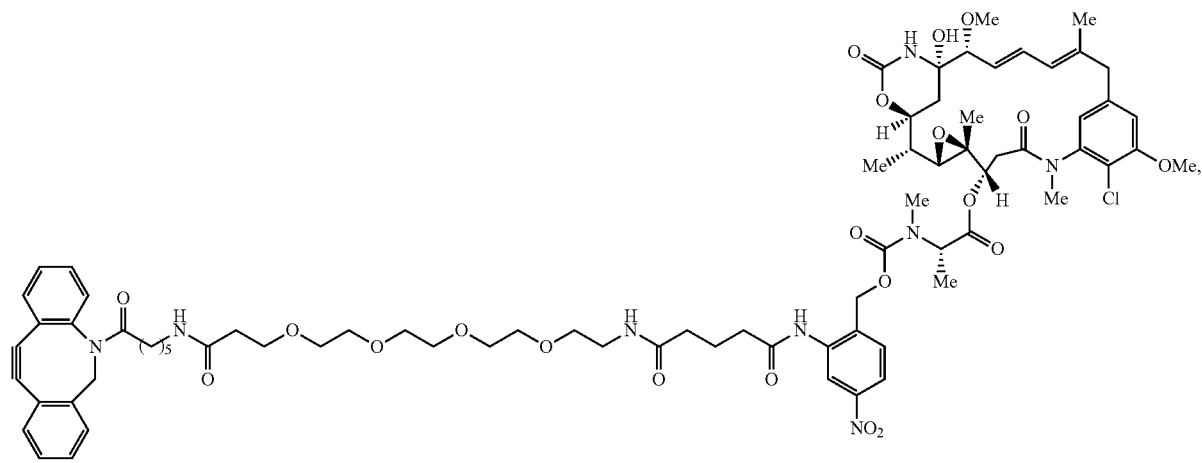
I8
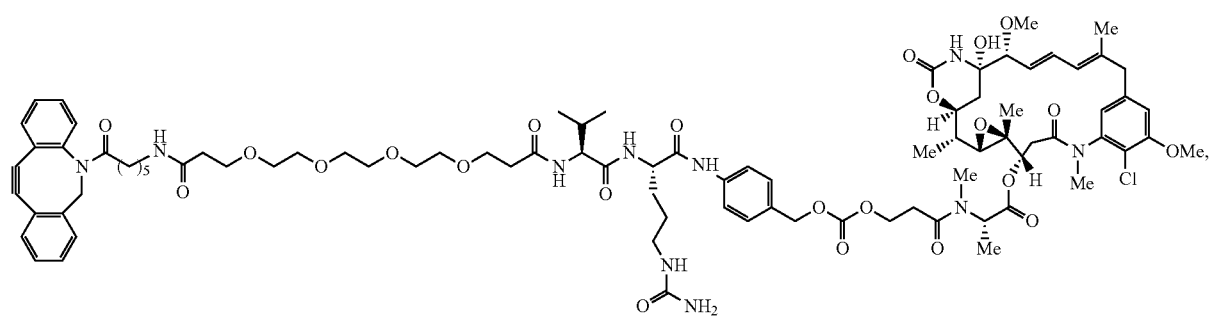
I9
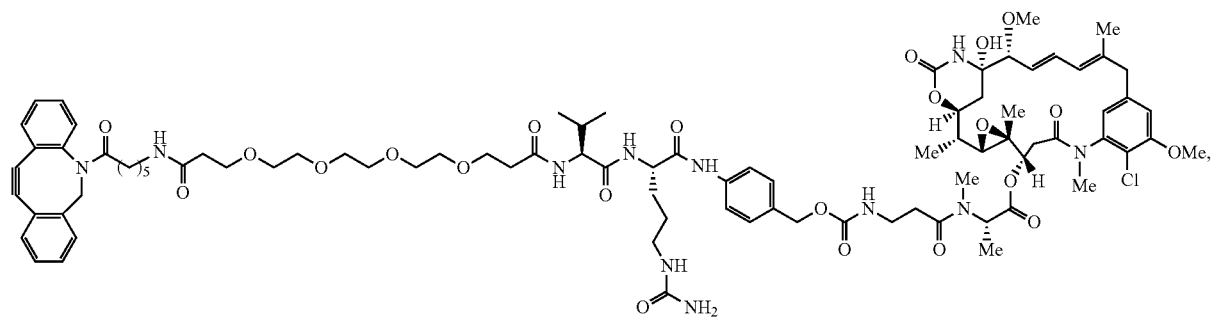
I10
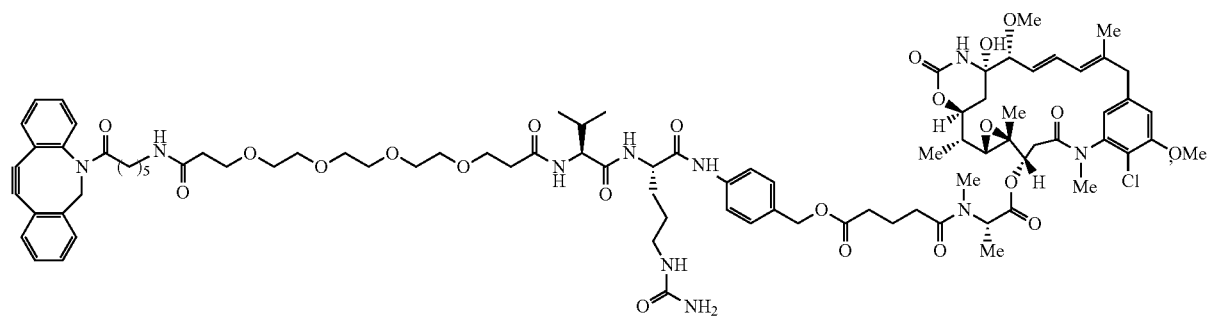
I11

-continued
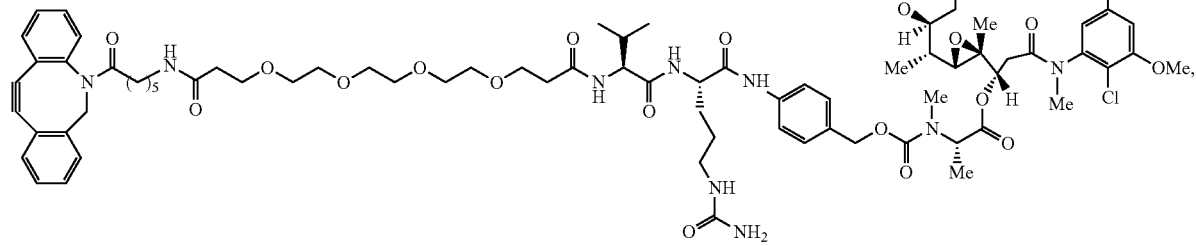
I12
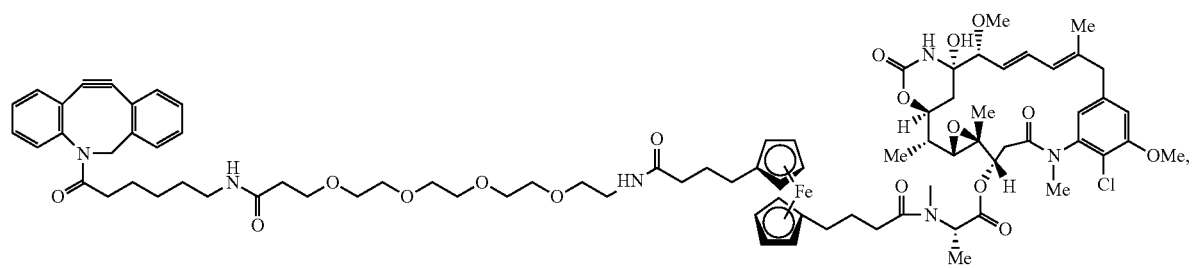
I13
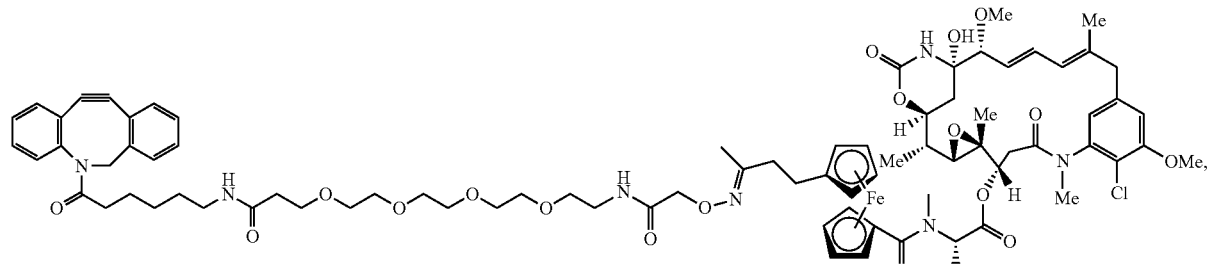
I14
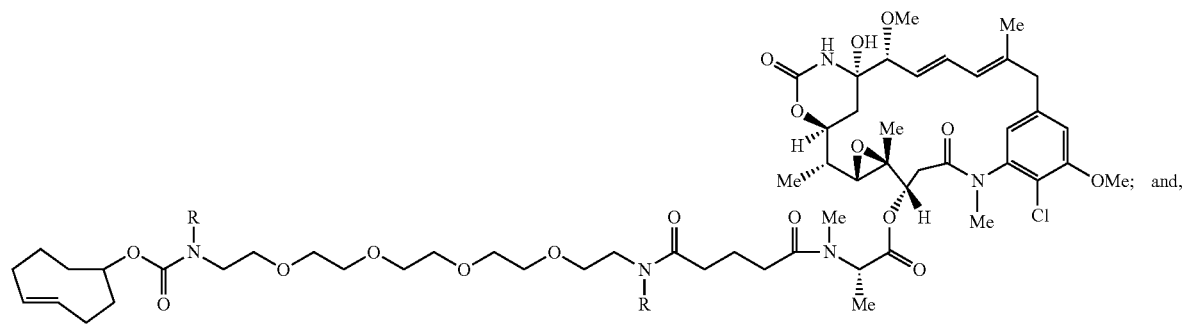
I15
R = H or CH₃ (methyl)

-continued

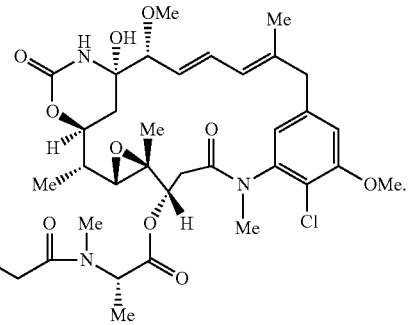

I16

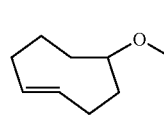

DETAILED DESCRIPTION OF THE INVENTION

Figure 1:
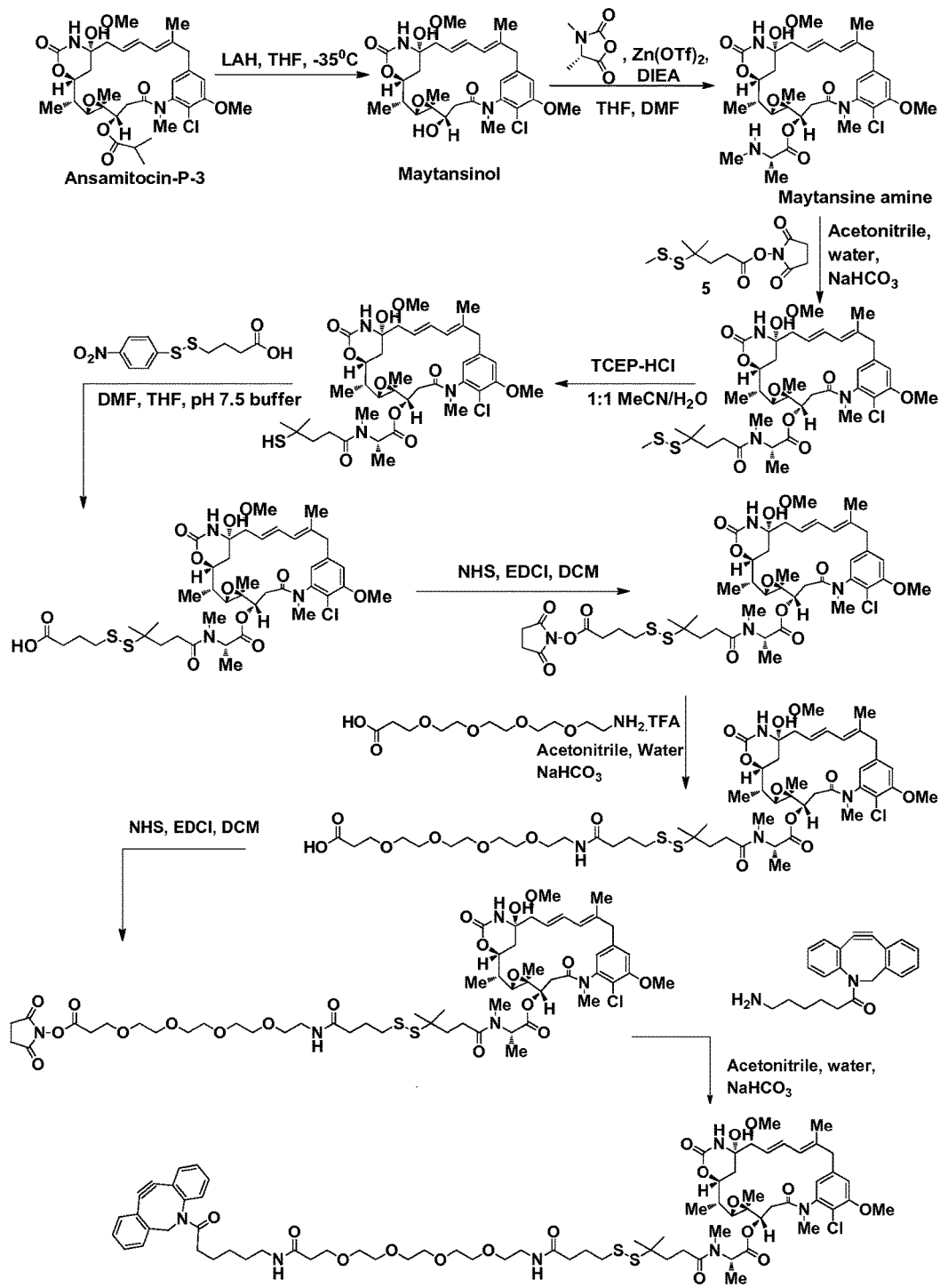
FIG. 1 illustrates an example preparation of a compound of Formula I by first forming an amide linking group followed by an extension of the linker.

Unless defined otherwise, all technical and scientific terms used herein have the same meaning as is commonly understood by one of skill in the art to which this invention belongs. All publications and patents referred to herein are incorporated by reference.

Targeted anti-cancer therapeutics described herein are designed to reduce nonspecific toxicities and increase efficacy relative to conventional cancer chemotherapy. This approach is embodied by the powerful targeting ability of monoclonal antibodies to specifically deliver highly potent, conjugated therapeutics to a cell which exhibits cancer-specific or cancer-associated antigens. Payloads, particularly cytotoxic agents are coupled to targeting molecules such as antibodies or ligands that bind with a high degree of specificity to cancer cells to form compounds referred to herein as biomolecule conjugates (conjugates) or antibody-drug conjugates (ADC) or immunoconjugates. Conjugates described herein should be less toxic because they direct a cytotoxic agent to cells, blood cancer cells, for example, that exhibit or otherwise overexpress the particular cell surface antigen or receptor.

Reference will now be made in detail to certain embodiments of the invention, examples of which are illustrated in the accompanying structures and formulas. While the invention will be described in conjunction with the embodiments disclosed herein, it will be understood that they are not intended to limit the invention to those embodiments. On the contrary, the invention is intended to cover all alternatives, modifications, and equivalents, which may be included within the scope of the present invention as well as defined by the claims appended hereto. One skilled in the art will recognize many methods and materials similar or equivalent to those described herein which can be used in the practice of the present invention. The present invention is in no way limited to the methods and materials described. It will be understood that in the following detailed description and appended claims, the abbreviations and nomenclature employed are those which are fundamentally standard in chemistry.

Unless stated otherwise, the following terms and phrases as used herein have the following definitions:

"Alkyl" is a C1-C18 hydrocarbon moiety containing normal, secondary, tertiary or cyclic carbon atoms. Examples of alkyl radicals include C1-C8 hydrocarbon moieties such as: methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, cyclopropyl, cyclobutyl, cyclopentyl, cyclohexyl, cycloheptyl, and cyclooctyl. An alkyl group can be substituted or unsubstituted.

"Alkenyl" is a C2-C18 hydrocarbon moiety containing normal, secondary, tertiary or cyclic carbon atoms with at least one site of unsaturation, i.e. a carbon-carbon, sp2 double bond. Examples of alkenyl radicals include C2-C8 hydrocarbon moieties such as, but not limited to: ethylene or vinyl (—CH═CH$_2$), allyl (—CH$_2$CH═CH$_2$), 1-cyclopent-1-enyl, 1-cyclopent-2-enyl, 1-cyclopent-3-enyl, 5-hexenyl (—CH$_2$CH$_2$CH$_2$CH$_2$CH═CH$_2$), 1-cyclohex-1-enyl, 1-cyclohex-2-enyl, and 1-cyclohex-3-enyl. An alkenyl group can be substituted or unsubstituted.

"Alkynyl" is a C2-C18 hydrocarbon moiety containing normal, secondary, tertiary or cyclic carbon atoms with at least one site of unsaturation, i.e. a carbon-carbon, sp triple bond. Examples of alkynyl radicals include C2-C8 hydrocarbon moieties such as, but not limited to: acetylenic (—C≡H) and propargyl (—CH$_2$C≡H). An alkynyl group can be substituted or unsubstituted.

"Amino" is substituted or unsubstituted unless otherwise noted. An amino group can be substituted by one or two substituents selected from hydrogen, alkyl, alkenyl, alkinyl, cycloalkyl, cycloalkylalkyl, arylalkyl, hydroxyalkyl, alkoxyalkyl, haloalkyl, unsubstituted or substituted aryl, aminoalkyl, acyl, e.g. formyl, alkylcarbonyl, arylcarbonyl, alkylsulfonyl or arylsulfonyl, and is preferably amino, methylamino, dimethylamino, propylamino, benzylamino, hydroxyethyl-methyl-amino, di(hydroxyethyl)amino, dimethylaminoethylamino, acetylamino, acetyl-methyl-amino, benzoylamino, methylsulfonylamino or phenylsulfonylamino, especially amino or dimethylamino.

"Aryl" means any carbon-based aromatic group including, but not limited to, benzene, naphthalene, phenyl, biphenyl, phenoxybenzene, and the like. An aryl group can be substituted or unsubstituted. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, 15 halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

"Heterocyclic or heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —CH$_2$— group can optionally be replaced by a —C(O)—, and a ring sulphur atom may be optionally oxidized to form S-oxide(s). Examples of heterocyclyls include, but are not limited to, pyrrolidinyl, morpholino, piperidyl, pyridyl, pyranyl, pyrrolyl, isothiazolyl, indolyl, quinolyl, thienyl, furyl, 1,3-benzodioxolyl, thiadiazolyl, piperazinyl, isoxazolyl, thiazolyl, thiazolidinyl, pyrrolidinyl, thiomorpholino, pyrazolyl, pyrrolinyl, homopiperazinyl, tetrahydropyranyl, imidazolyl, pyrimidyl, pyrazinyl, pyridazinyl, isoxazolyl, 4-pyridone, 1-isoquinolone, 2-pyrrolidone, 4-thiazolidone, imidazo[1,2-a]pyridine or 3-aza-8-oxabicyclo[3,2,1]hexane. Heterocycles are described in Paquette, Leo A., "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. A heterocyclic group can be substituted or unsubstituted.

"Carbamoyl" can be substituted or unsubstituted unless otherwise noted. A carbamoyl group may be substituted by one or two substituents selected from hydrogen, alkyl, alkenyl, alkinyl, cycloalkyl, cycloalkylalkyl, arylalkyl, hydroxyalkyl, alkoxyalkyl, haloalkyl, unsubstituted or substituted aryl, or aminoalkyl, or carbamoyl wherein the substituents and the nitrogen atom of the carbamoyl group represent a 5 or 6 membered heterocyclyl further comprising 0, 1 or 2 hetero atoms selected from N, O and S; and is preferably carbamoyl, methylcarbamoyl, dimethylcarbamoyl, propylcarbamoyl, hydroxyethyl-methyl-carbamoyl, di(hydroxyethyl)carbamoyl, dimethylaminoethylcarbamoyl, or pyrrolidinocarbonyl, piperidinocarbonyl, N-methylpiperazinocarbonyl or morpholinocarbonyl, especially carbamoyl or dimethylcarbamoyl.

"Carbocycle" and "carbocyclyl", synonymous, indicate a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl. An carbocycle group can be substituted or unsubstituted.

A non-natural amino acid (NNAA) fundamentally refers to an amino acid that is not one of the 20 amino acids found in nature. Examples of such NNAA include, but are not limited to, amino acids having an azide group or a tetrazine group. Example NNAA include, but are not limited to, azido-pheylalanine or azido-para-methyl-phenylalanine.

A "linking group" as defined herein, for example, refers to a functional group between a linker (E) and a payload (D). Examples of a linking group include, but are not limited to, amide, ester, carbamate, ether, thioether, disulfide, hydrazone, oxime, semicarbazide, urea, carbonate, acid labile group, photolabile group, peptidase labile group and esterase labile group. See, for example, U.S. Pat. Nos. 5,208,020; 5,475,092; 6,441,163; 6,716,821; 6,913,748; 7,276,497; 7,276,499; 7,368,565; 7,388,026 and 7,414,073.

A "linker" (spacer arm) (E) refers to a chemical moiety between two linking groups. CB-E-D. Linker (E) is the chemical moiety between a linking group to the cell binding agent (CB) and a linking group to a payload (D). A linker (E) can be cleavable or non-cleavable. A linker links a cytotoxic agent with a cell-binding agent or a chemical moiety which can be further connected to a cell-binding agent. For example, a linker (E) links a maytansinoid to a chemical moiety such as a strained alkyne, which is capable of being connected, as described herein, to an antibody containing an azide-substituted non-natural amino acid via Huisgen cycloadditions (aka Sharpless "click" reactions).

Preparations and applications of linkers are readily available to one of ordinary skill in the art. Goldmacher et al., Antibody-drug Conjugates and Immunotoxins: *From Preclinical Development to Therapeutic Applications*, Chapter 7, in *Linker Technology and Impact of Linker Design on ADC Properties*, Edited by Phillips GL; Ed. Springer Science and Business Media, New York (2013). Linker structures for use in the present invention are also disclosed in U.S. Pat. Nos. 8,198,417; 8,012,485; 7,989,434; 6,333,410; 5,416,064, and 5,208,020, for example; the entire disclosures of which are hereby incorporated by reference.

Cleavable linkers (E) are linkers that can be cleaved under mild conditions. Disulfide containing linkers are linkers cleavable through disulfide exchange which occur under physiological conditions. Acid-labile linkers are linkers cleavable at acid pH. For example, certain intracellular compartments, such as endosomes and lysosomes, have an acidic pH (pH 4-5), and provide conditions suitable to cleave acid-labile linkers. Linkers that are photolabile are useful at the body surface and in many body cavities that are accessible to light. Furthermore, infrared light can penetrate tissue. Certain linkers can be cleaved by native peptidases. See, e.g., Trouet, et al., 79 Proc. Natl. Acad. Sci. USA, 626-629 (1982) and Umemoto, et al., 43 Int. J. Cancer, 677-684 (1989). Peptides are composed of α-amino acids and peptidic bonds, which are amide bonds between the carboxylate of one amino acid and the α-amino group of another amino acid and so on and on. Other amide bonds, such as the bond between a carboxylate and the ε-amino group of lysine, are understood not to be peptidic bonds and are considered non-cleavable. Many linkers known in the art can be cleaved by esterases. Only certain esters known in the art can be cleaved by esterases present inside or outside cells. Esters are formed by the condensation of a carboxylic acid and an alcohol. Simple esters are esters produced with simple alcohols, such as aliphatic alcohols, and small cyclic and small aromatic alcohols.

A non-cleavable linker (E) is any chemical moiety that is capable of linking a payload, e.g., a cytotoxic agent, to a cell-binding agent in a stable, covalent manner and does not fall under the categories listed above as cleavable linkers. Thus, non-cleavable linkers are generally resistant to acid-induced cleavage, light-induced cleavage, peptidase-induced cleavage, esterase-induced cleavage, and disulfide bond cleavage. The term "pharmaceutically acceptable salt" as used herein, refers to pharmaceutically acceptable organic or inorganic salts of a compound of the invention, including biomolecule conjugates. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

The term "therapeutically effective amount" or "effective amount" means that amount of active compound or conjugate that elicits the desired biological response or therapeutic effect in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy is determined by standard pharmaceutical procedures in cell culture and animal studies. The effective amount of compound or conjugate of the present invention or other therapeutic agent to be administered to a subject will depend on the stage, category and status of the condition, multiple myeloma or leukemia, for example, and characteristics of the subject, such as general health, age, sex, body weight and drug tolerance. The effective amount of compound or conjugate of the present invention or other therapeutic agent to be administered will also depend on administration route and dosage form. Intravenous (IV) and subcutaneous (SC) administration routes are preferred. Dosage amount and interval can be adjusted individually to provide plasma levels of the active compound that are sufficient to maintain desired therapeutic effects.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Unless specified otherwise, compounds of this invention are intended to include all stereoisomers, which exist as a single isomer or in mixture with other isomers.

In Formula I compounds of the present invention, (A) is a strained ring, i.e., strained alkyne ring or strained alkene ring. The strained alkyne (A) or strained alkene (A) and cytotoxic agent, for example, (D) are connected via a linker $(E)_m$. Various linking groups for employment at the point of connection of $(E)_m$ (to (A) or (D), or both) include, for example, but are not limited to ester, amide, carbamate, amine, and thioether.

Formula I

A compound of Formula I:

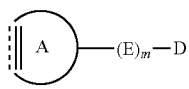

Formula I

A is a ring, provided that A is a ring with a strained alkyne when the dotted line represents a bond, or A is a ring with a strained alkene when the dotted line is absent;

Formula I, in other words, includes both following structures:

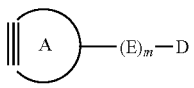

Formula Ia

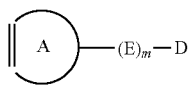

Formula Ib

D is a cytotoxic agent;

Each E is independently selected from the group consisting of —CO—, —CR$^1$R$^2$—, —NR$^3$—, —S—S—, —S—, —SO—, —SO$_2$—, —O—, —CR$^3$=N—NR$^3$—, —CR$^3$=N—O—, —CR$^3$=N—NR$^3$—CO—, —N=N—CO—, alkyl, C3-C8 carbocyclyl, —O—(CR$^1$R$^2$)$_a$—, aryl, —(CR$^1$R$^2$)$_a$-aryl, heteroaryl, —(CR$^1$R$^2$)$_a$-heteroaryl, —(CR$^1$R$^2$)$_a$—C3-C8 carbocyclyl, heterocyclyl, —(CR$^1$R$^2$)$_a$-heterocyclyl, —(CH$_2$CH$_2$O)$_a$—, —(CH$_2$CH$_2$O)$_a$—(CH$_2$)$_b$—, —(CH$_2$)$_a$C(O)—, amino acid, and peptide;

R$^1$ and R$^2$ are each independently selected from the group consisting of H, F, Cl, Br, I, OH, —N(R$^3$)$_2$, —N(R$^3$)$_3^+$, C1-C8 alkylhalide, carboxylate, sulfate, sulfamate, sulfonate, —SO$_2$R$^3$, —S(=O)R$^3$, —SR$^3$, —SO$_2$N(R$^3$)$_2$, —C(=O)R$^3$, —CO$_2$R$^3$, —C(=O)N(R$^3$)$_2$, —CN, —N$_3$, —NO$_2$, C1-C8 alkoxy, polyethyleneoxy, phosphonate, phosphate, C1-C8 alkyl, C2-C8 alkenyl, C2-C8 alkynyl, aryl, heteroaryl, C3-C8 carbocyclyl, and C1-C20 heterocyclyl; or when taken together, R$^1$ and R$^2$ form a carbonyl (=O), or spiro carbocyclic ring of 3 to 7 carbon atoms;

R$^3$ is independently selected from the group consisting of H, C1-C8 alkyl, C2-C8 alkenyl, C2-C8 alkynyl, C6-C20 aryl, C6-C20 heteroaryl, C3-C8 carbocyclyl, and C1-C20 heterocyclyl; When substituted, alkyl, carbocyclyl, alkenyl, alkynyl, aryl, heteroaryl, carbocyclyl, and heterocyclyl are independently substituted with one or more substituents selected from the group consisting of F, Cl, Br, I, OH, —N(R$^3$)$_2$, —N(R$^3$)$_3^+$, C1-C8 alkylhalide, carboxylate, sulfate, sulfamate, sulfonate, C1-C8 alkylsulfonate, C1-C8 alkylamino, 4-dialkylaminopyridinium, C1-C8 alkylhydroxyl, C1-C8 alkylthiol, —SO$_2$R, —S(=O)R$^3$, —SR$^3$, —SO$_2$N(R$^3$)$_2$, —C(=O)R$^3$, —CO$_2$R$^3$, —C(=O)N(R$^3$)$_2$, —CN, —N$_3$, —NO$_2$, C1-C8 alkoxy, C1-C8 trifluoroalkyl, C1-C8 alkyl, C3-C12 carbocycle, C6-C20 aryl, C6-C20 heteroaryl, C3-C8 carbocyclyl, C2-C20 heterocyclyl, polyethyleneoxy, phosphonate, and phosphate;

m is an integer from 1 to 100; and, a and b are each an integer from 1 to 100.

In certain embodiments, m is an integer from 1 to 30. In some embodiments, m is an integer from 1 to 25. In some embodiments, m is an integer from 1 to 20. In some embodiments, m is an integer from 1 to 15. In some embodiments, m is an integer from 1 to 10. In some embodiments, m is an integer from 1 to 5. In some embodiments, m is an integer from 1 to 3. In some embodiments, m is an integer from 1 to 2. In some embodiments, m is 1.

In certain embodiments, a and b are each independently an integer from 1 to 100. In some embodiments, a and b are each independently an integer from 1 to 30. In some embodiments, a and b are each independently an integer from 1 to 25. In some embodiments, a and b are each independently an integer from 1 to 20. In some embodiments, a and b are each independently an integer from 1 to 15. In some embodiments, a and b are each independently an integer from 1 to 10. In some embodiments, a and b are each independently an integer from 1 to 5. In some embodiments, a and b are each independently an integer from 1 to 3. In some embodiments, a and b are each independently an integer from 1 to 2. In some embodiments, a and b are each independently 1.

Each E in -(E)$_m$- can be the same or different. In one embodiment, for example, a combination of alkyl and carbocycle leads to -(E)$_2$-, wherein one E is alkyl and the other E is carbocycle.

In non-limiting exemplary embodiments, each E can be derived from a maleimido-based moiety selected from N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimidobutyric acid N-succinimidyl ester (GMBS), ε-maleimidcaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido) hexanoate (SMPH), N-succinimidyl 4-(p-maleimidophenyl)-butyrate (SMPB), N-(p-maleimidophenyl)isocyanate (PMPI), or a sulfo-succinimidyl variant or an analog thereof. In other non-limiting exemplary embodiments, each E can also be derived from a haloacetyl-based moiety selected from N-succinimidyl-4-(iodoacetyl)-aminobenzoate (SIAB), N-succinimidyl iodoacetate (SIA), N-succinimidyl bromoacetate (SBA), N-succinimidyl 3-(bromoacetamido) propionate (SBAP), or a sulfo-succinimidyl variant or an analog thereof.

In certain embodiments, each E is independently selected from the group consisting of —(CH$_2$CH$_2$O)$_a$—, —(CH$_2$)$_a$C(O)NR$^3$—, —(CH$_2$)$_a$NR$^3$C(O)—, —(CH$_2$)$_a$C(O)NR$^3$(CH$_2$)$_b$—, —(CH$_2$)$_a$C(O)NR$^3$(CH$_2$CH$_2$O)$_b$—, —(CH$_2$)$_a$C(O)NR$^3$(CH$_2$CH$_2$O)$_b$(CH$_2$)$_c$—, —(CH$_2$CH$_2$O)$_a$C(O)NR$^3$(CH$_2$CH$_2$O)$_b$—, —(CH$_2$CH$_2$O)$_a$C(O)NR$^3$(CH$_2$CH$_2$O)$_b$—, —(CH$_2$CH$_2$O)$_a$C(O)NR$^3$(CH$_2$)$_b$—, —(CH$_2$CH$_2$O)$_a$—(CH$_2$)$_b$—, —(CH$_2$)$_a$C(O)—, —CR$^3$=N—NR$^3$—, —CR$^3$=N—O—, —CR$^3$=N—NR$^3$—CO—, —N=N—CO, —S—S—, —S—, —SO$_2$—, —SO$_2$—, —O—, amino acid, peptide,

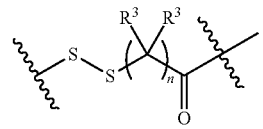

E1

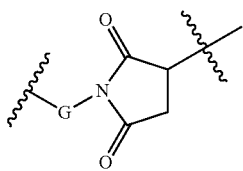

E2

Wherein G is selected from the group consisting of alkyl, aryl, and heterocyclyl, and

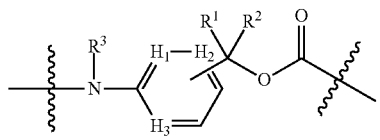

G1

Wherein $H_1$, $H_2$, and $H_3$ are each N or $CR^1$; and $R^1$, $R^2$, and $R^3$ are as defined above.

In some embodiments, each E is independently selected from the group consisting of wherein J is an amino acid or peptide;

d, e, g, i, j, and k are each independently an integer from 1 to 30;

h is an integer from 0 to 30;

$R^1$, $R^2$, and $R^3$ are as defined above;

Each $R^4$ is independently selected from the group consisting of H, alkyl, —$N(R^3)_2$, —$SR^3$; and, C1-C8 alkoxy, aryl;

$R^5$ is selected from the group consisting of H, —$N(R^3)_2$, —$SR^3$, C1-C8 alkoxy, aryl, and $NO_2$.

In certain embodiments, d, e, g, i, j, and k are each independently an integer from 1 to 30. In some embodiments, d, e, g, i, j, and k are each independently an integer from 1 to 25. In some embodiments, d, e, g, i, j, and k are each independently an integer from 1 to 20. In some embodiments, d, e, g, i, j, and k are each independently an integer from 1 to 15. In some embodiments, d, e, g, i, j, and k are each independently an integer from 1 to 10. In some embodiments, d, e, g, i, j, and k are each independently an integer from 1 to 5. In some embodiments, a and b are each independently an integer from 1 to 3. In some embodiments,

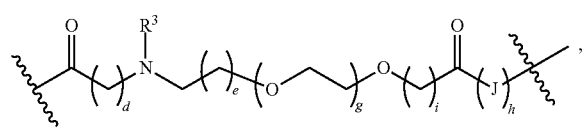

E3

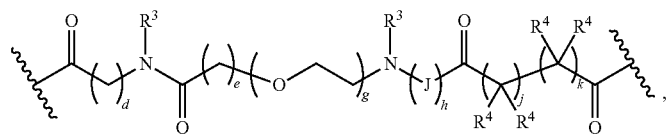

E4

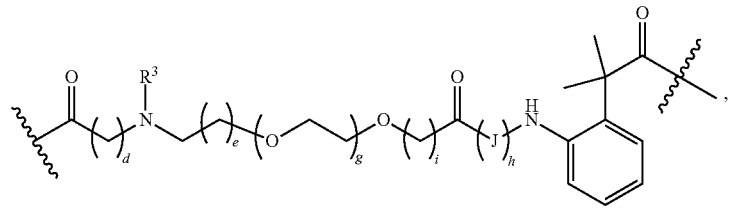

E5

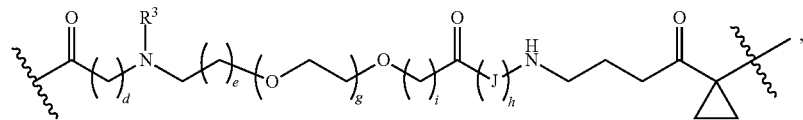

E6

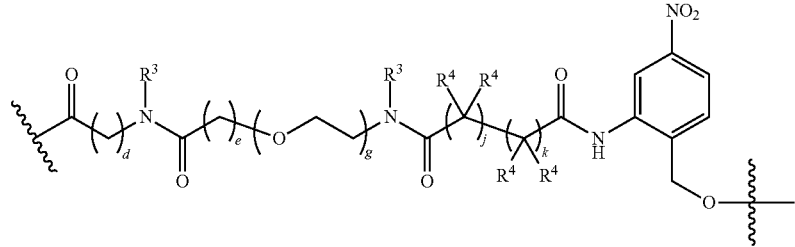

E7

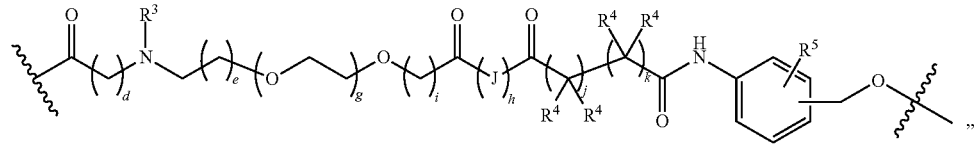

E8 d, e, g, i, j, and k are each independently an integer from 1 to 2. In some embodiments, d, e, g, i, j, and k are each independently 1.

In certain embodiments, h is an integer from 0 to 30. In some embodiments, h is an integer from 0 to 25. In some embodiments, h is an integer from 0 to 20. In some embodiments, h is an integer from 0 to 15. In some embodiments, h is an integer from 0 to 10. In some embodiments, h is an integer from 0 to 5. In some embodiments, h is an integer from 0 to 3. In some embodiments, h is an integer from 0 to 2. In some embodiments, h is 1. In some embodiments, h is 0.

In some embodiments, each E is independently selected from the group consisting of

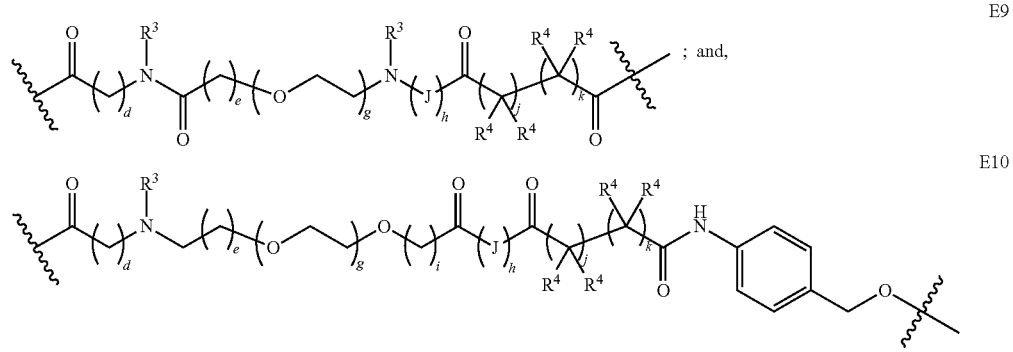

In non-limiting exemplary embodiments, E may have any of the following structures:

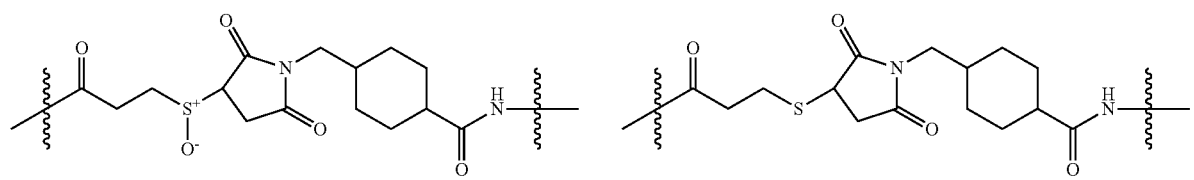

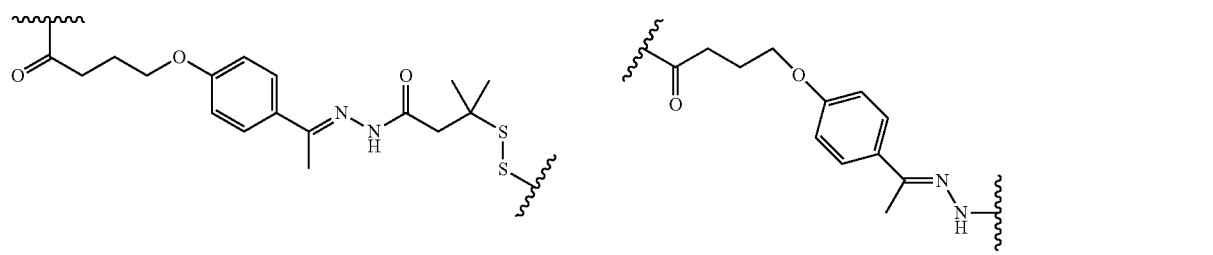

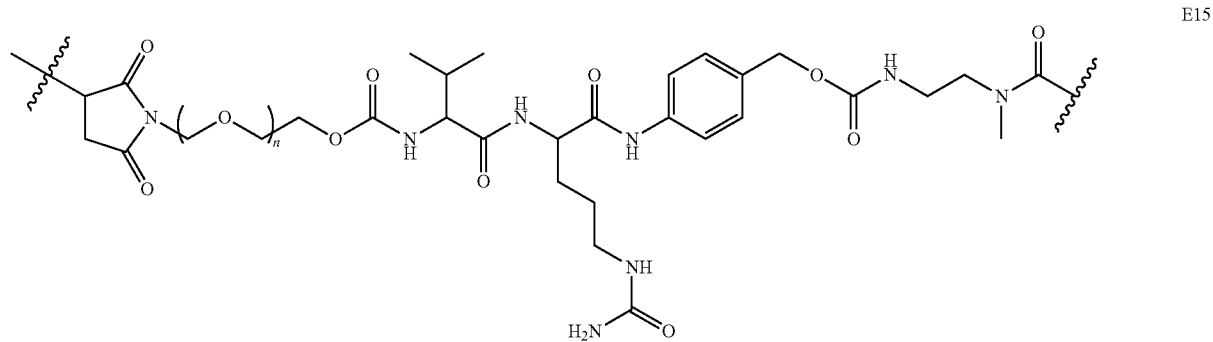

E16
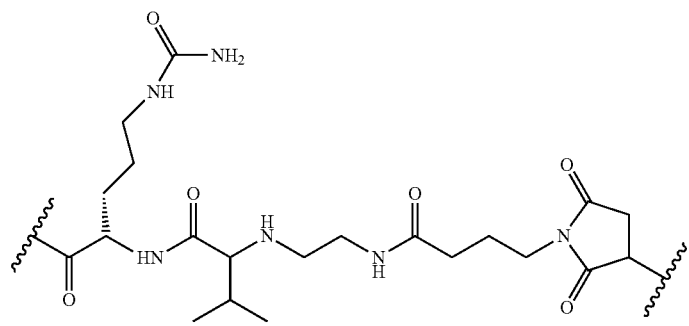
E17
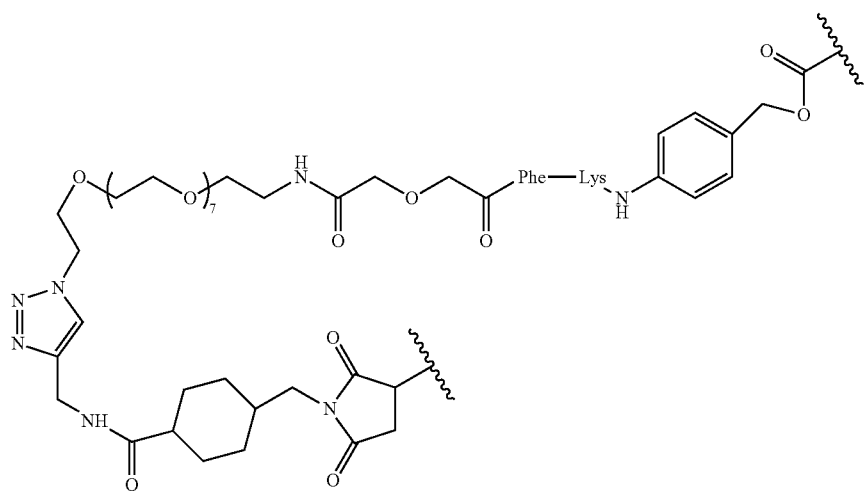
E18
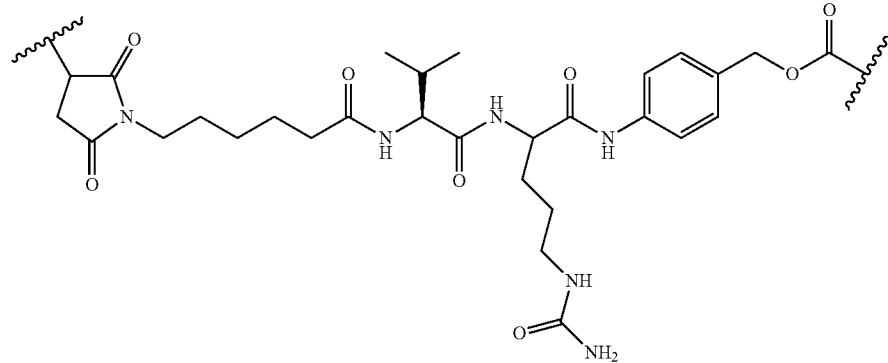
E19
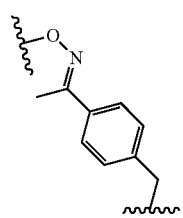
E20
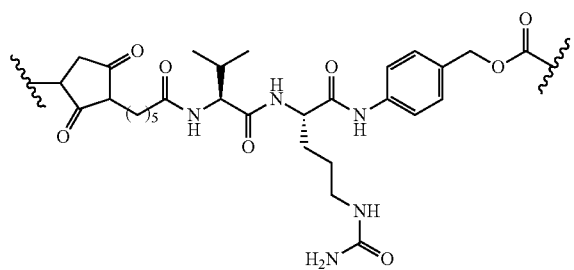

E21 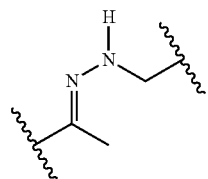
E22 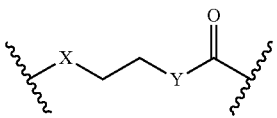
X = O, S, NH
Y = CH2, NR, O
E23 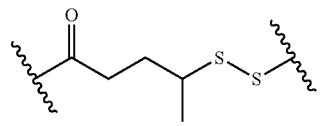
E24 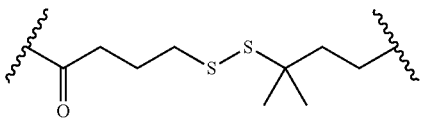
E25 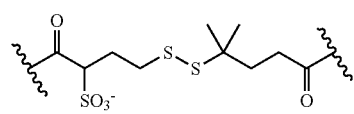
E26 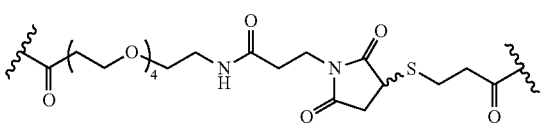
E27 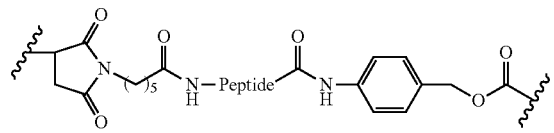
E28 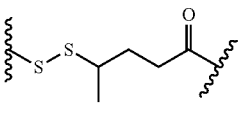
E29 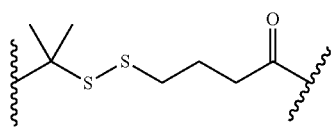
E30 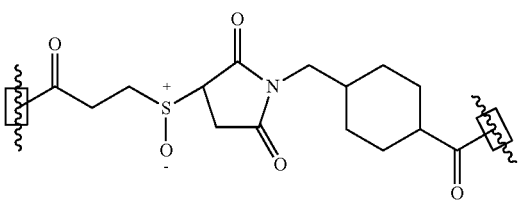
E31 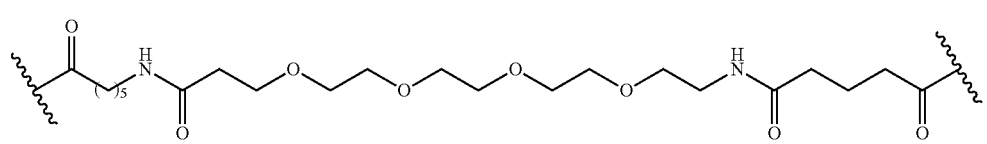
E32 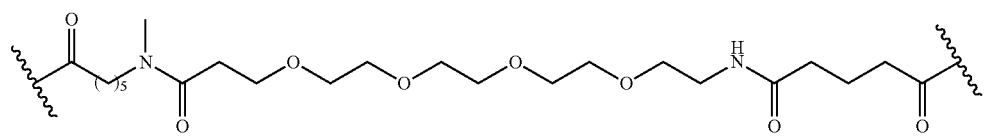
E33 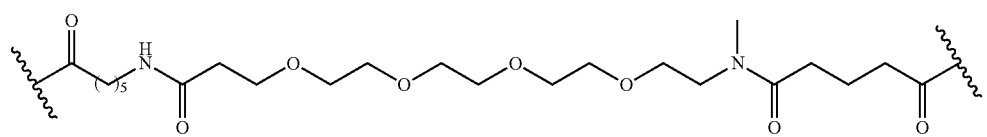
E34 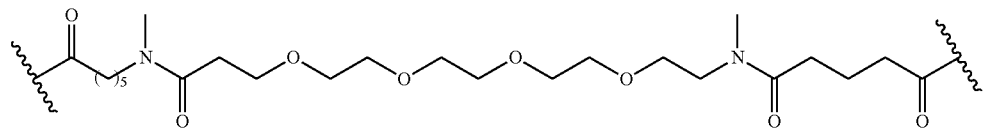
E35 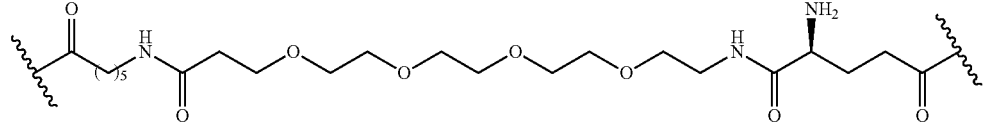

-continued

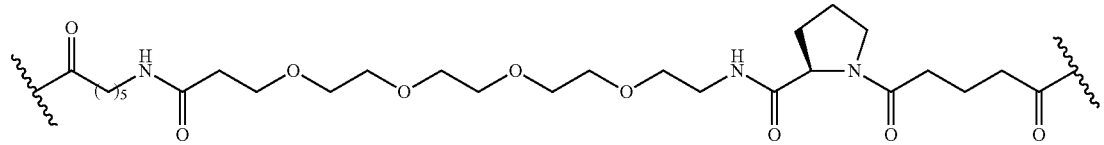

E36

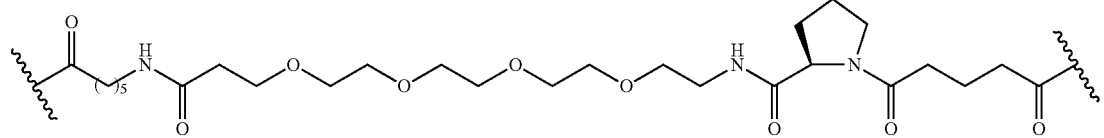

E37

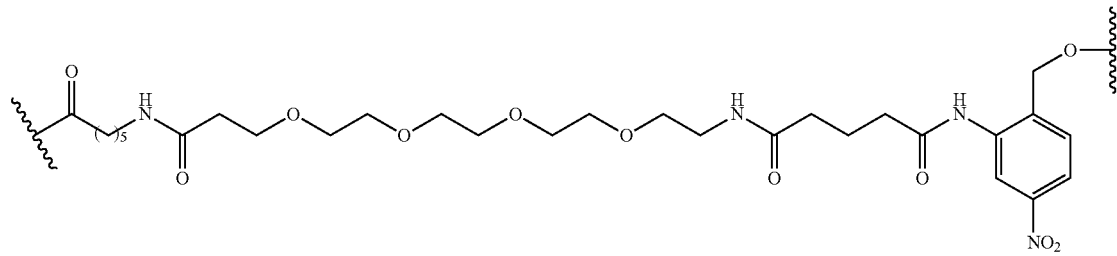

E38

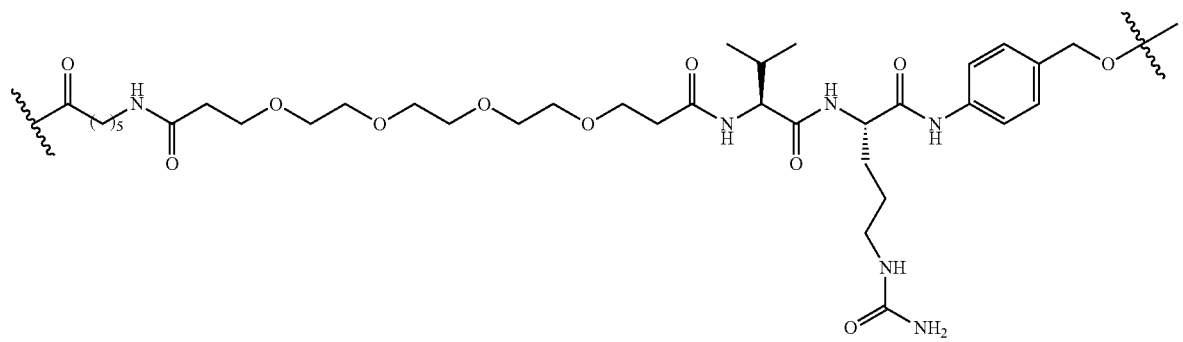

E39

Figure 2:
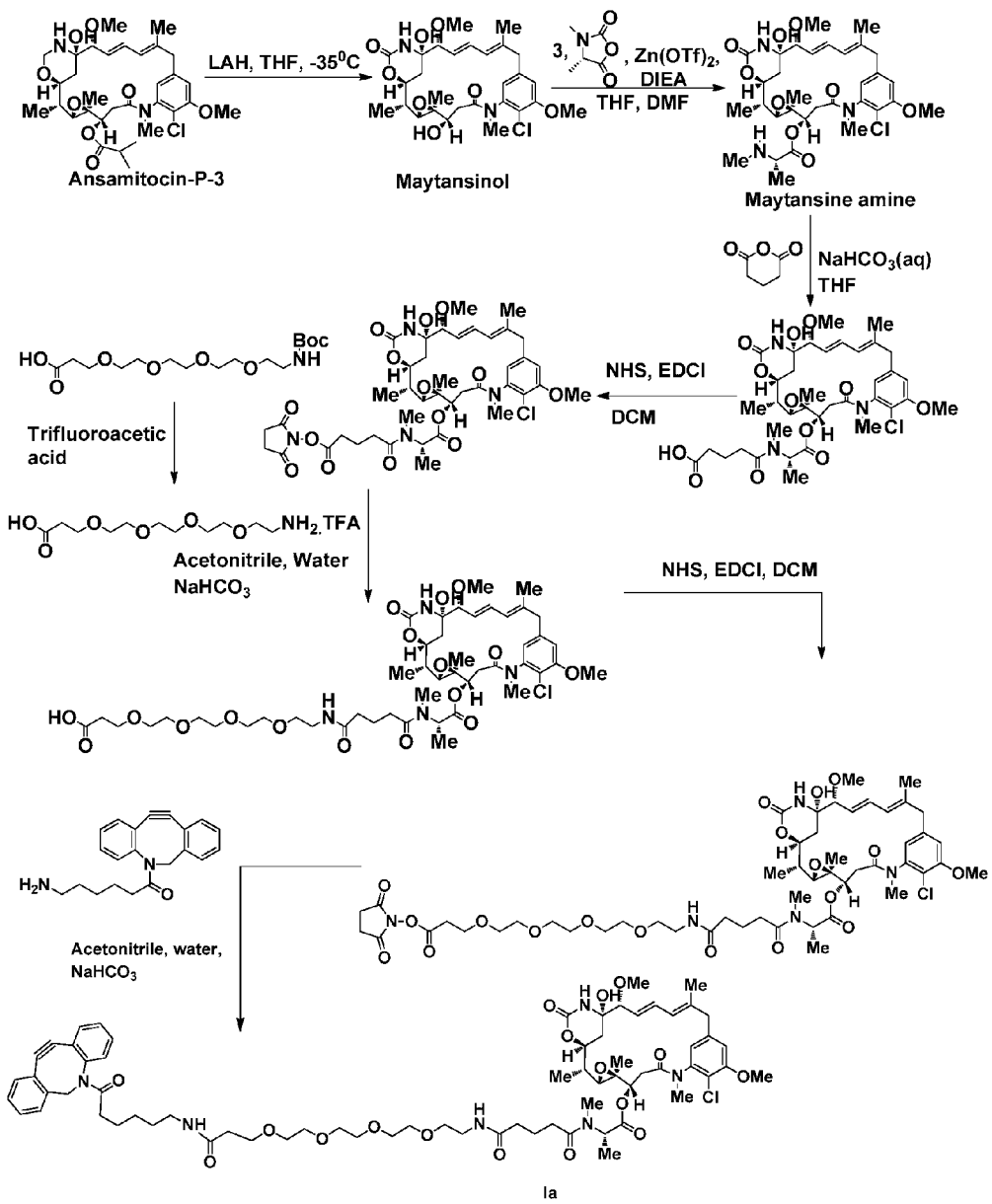
FIG. 2 illustrates an example preparation of a compound of Formula I and corresponding intermediates.
Figure 3:
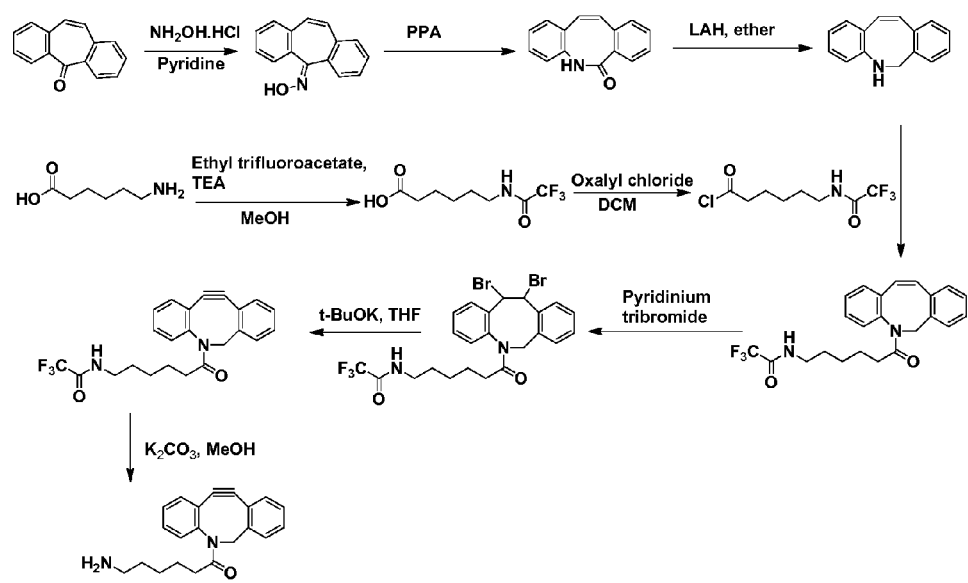
FIG. 3 shows the preparation of an intermediate wherein a strained alkyne is connected to a fragment of a linker.
Figure 4:
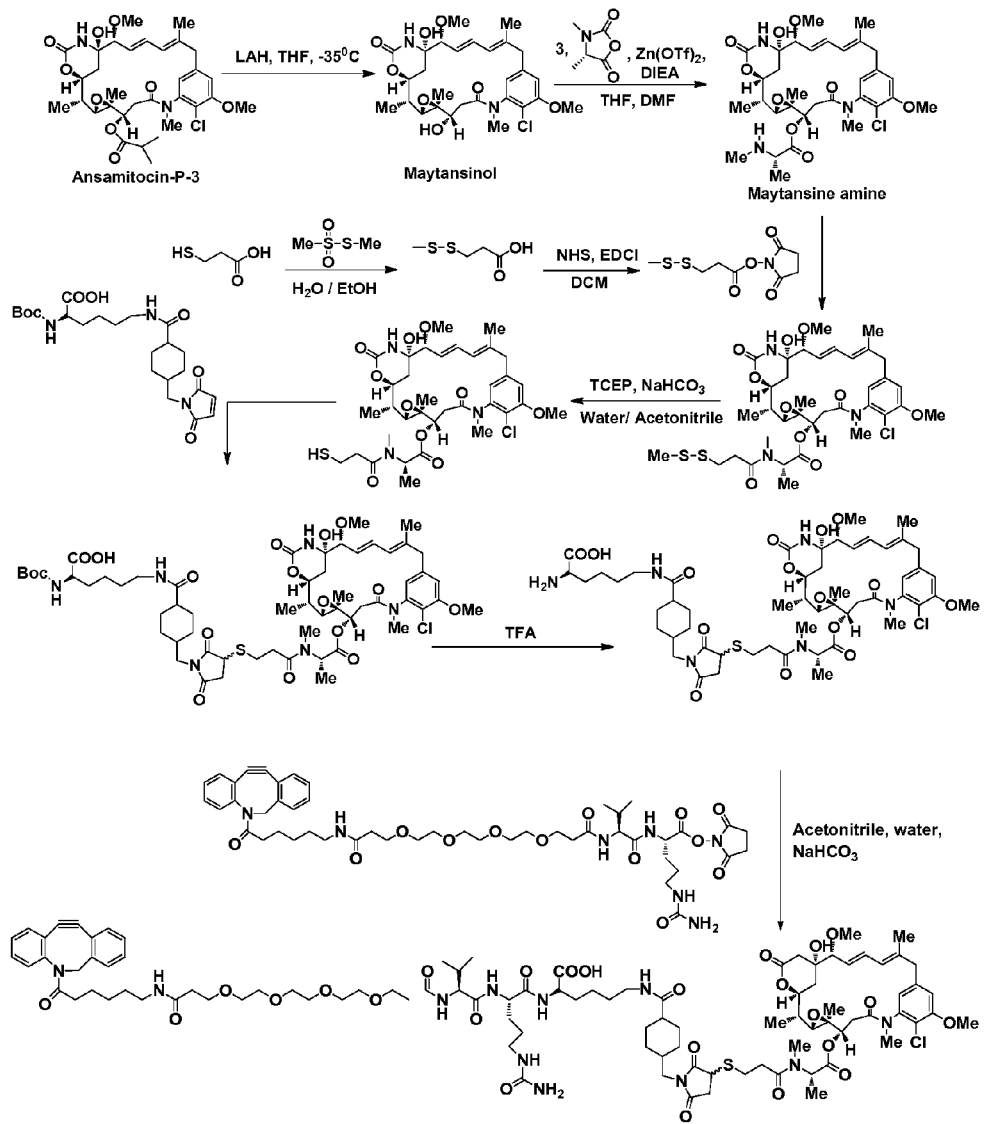
FIG. 4 describes the preparation of a compound of Formula I by first forming an amide linking group followed by extension of the linker.
Figure 5:
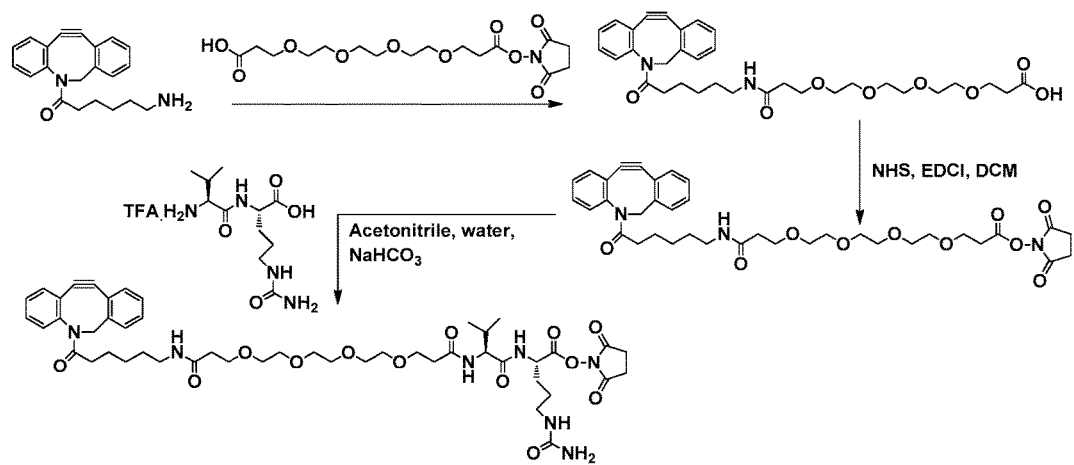
FIG. 5 describes the preparation of an intermediate wherein a strained alkyne is connected to a linker.

Synthesis of compounds of Formula I is well within the skill of one of ordinary skill in the art. Without being limited to any particular chemistry approach, exemplary routes readily accomplishable to the synthesis of compounds of Formula I and intermediates are illustrated in FIG. 1 and FIG. 2.

The term "strained ring" (A) as used herein refers to a strained alkyne or a strained alkene ring.

Strained Alkyne Rings (A) of Formula I

Strained alkyne rings (A) have bond angles for the sp-hybridized carbons less than 180°, in contrast to linear alkynes. Strained alkyne rings can be substituted on the rings and/or on their side chains. Strained alkynes, as referred to herein, may also include derivatives with reactive functional groups for connecting linkers (E).

Strained alkyne A of Formula I enables it to react efficiently with azide-containing NNAA under mild conditions without the addition of copper catalysts. Preparations of various strained alkynes and their reactions with azide-containing compounds are well known in the literature, including Martell et al., Molecules, 2014, 19(2), 1378-93; Sletten et al., Org. Lett. 2014, 16(6), 1634-7; Debets et al., Acc. Chem. Res. 2011, 44(9), 805-15; Jewett et al., Org. Lett. 2011, 13(22), 5937-9; Jewett et al., Chem. Soc. Rev. 2010, 39(4), 1272-9; Bertozzi et al., J. Am. Chem. Soc. 2010, 132, 3688; Jewett et al. Chem Soc Rev. 2010 April; 39(4):1272-9.

Non-limiting exemplary embodiments include strained alkyne regents dibenzocyclooctyne, cyclooct-4-ynol, (1R, 8S,9S)-bicyclo[6.1.0]non-4-yn-9-ylmethyl N-succinimidyl carbonate, as well as their derivatives and analogs.

Strained alkynes may be connected to a linker (E), for example, by an amide bond, amine bond, ether bond, or ester bond.

SA1

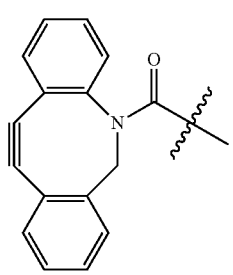

-continued

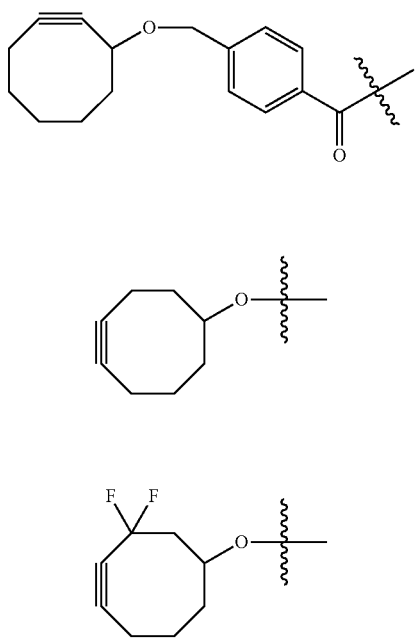

n = 1-2

Inverse electron-demand Diels-Alder reactions between strained alkenes (including norbornenes and trans-cyclooctenes) and tetrazines have emerged as an important class of rapid bioorthogonal reactions. The reactions can often proceed under very mild conditions. A host of literatures describes preparation and reactions of strained alkenes, including Kim et al., Curr. Opin. Chem. Biol. 2013, 17(3), 412-9; Sěckutė et al., Curr Opin Chem Biol. 2013, 17(5), 761-7; Seitchik et al., J. Am. Chem. Soc. 2012, 134(6), 2898-2901; Taylor, et al., J. Am. Chem. Soc. 2011, 133, 9646; Devaraj, et al., Bioconjugate Chem. 2008, 19, 2297; Devaraj, N. K.; Weissleder, R. Acc. Chem. Res. 2011, 44, 816; Taylor, M. T.; et al. J. Am. Chem. Soc. 2011, 133, 9646; Blackman, M. L.; et al. J. Am. Chem. Soc. 2008, 130, 13518.

Strained alkynes may be connected to a linker (E), for example, by an ether, amide, carbamate, or ester.

Example Strained Alkene Rings (A) of Formula I

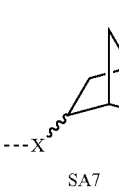
SA7

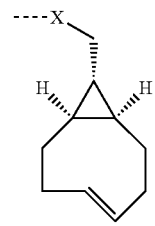
SA8

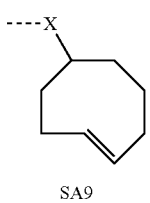
SA9

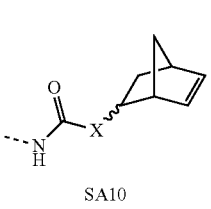
SA10

SA11

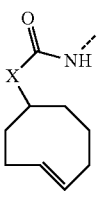
SA12

X = O or NH

In non-limiting exemplary embodiments, strained alkenes for employment in the present invention may have the following structures:

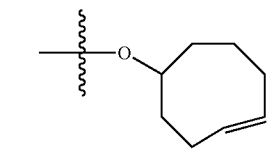

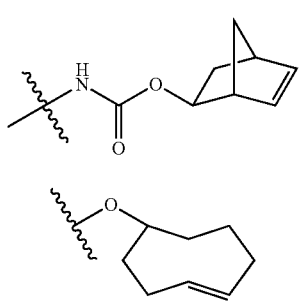

Example Species of Formula I
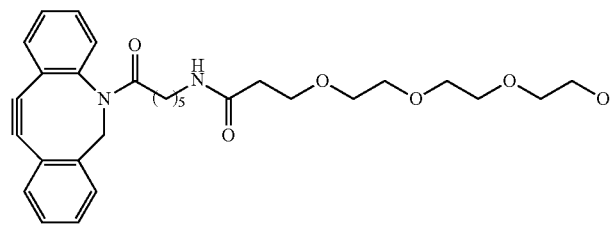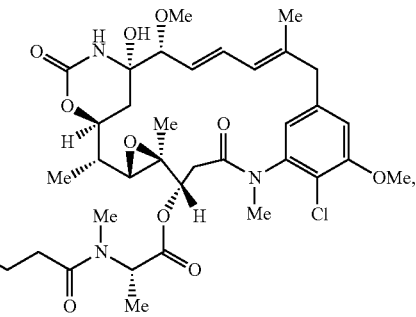
I17
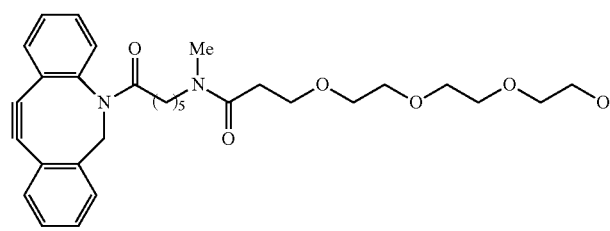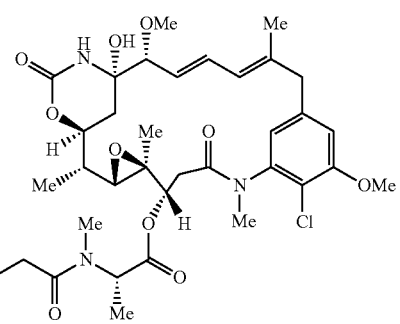
I18
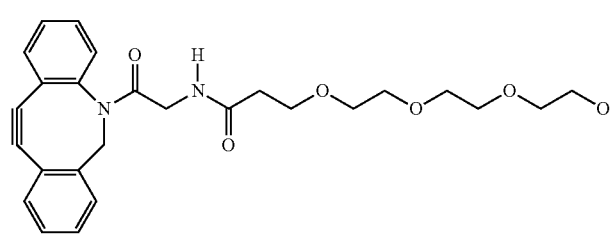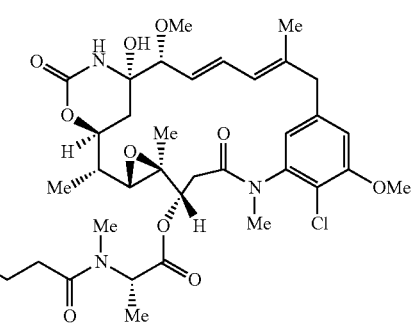
I19

-continued
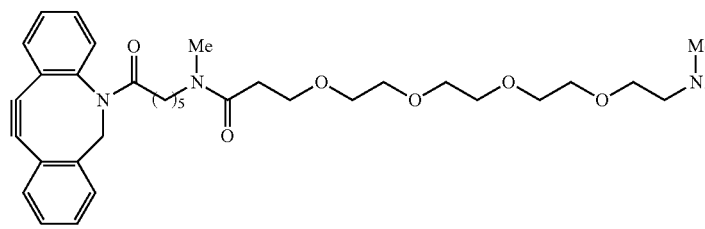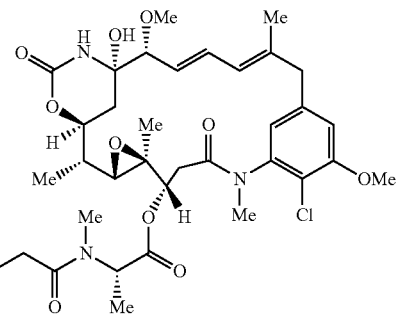
I20
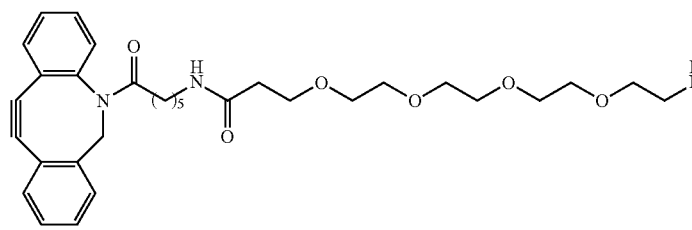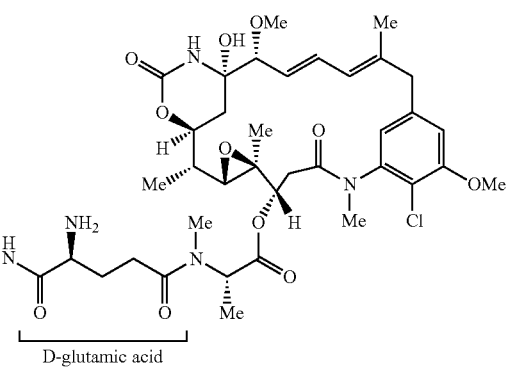
I21
D-glutamic acid
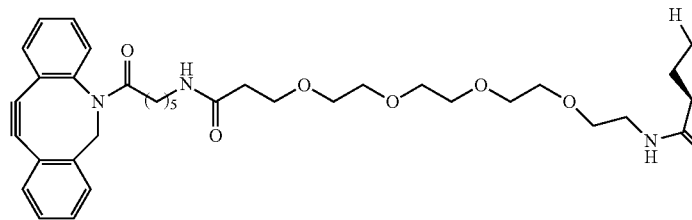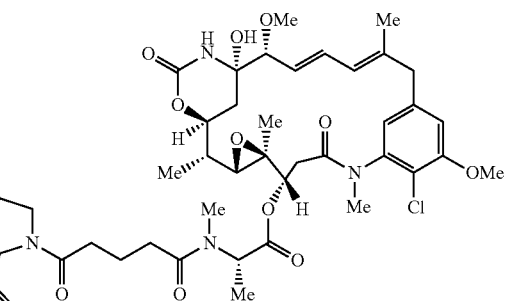
I22
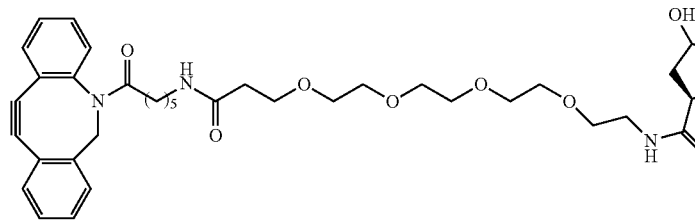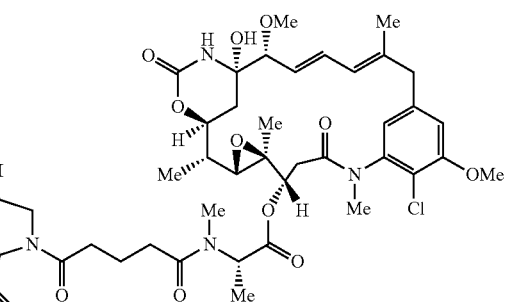
I23

-continued
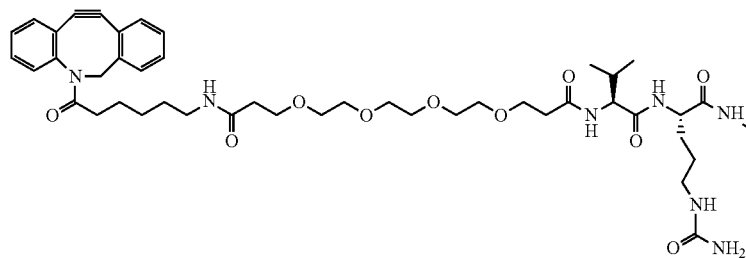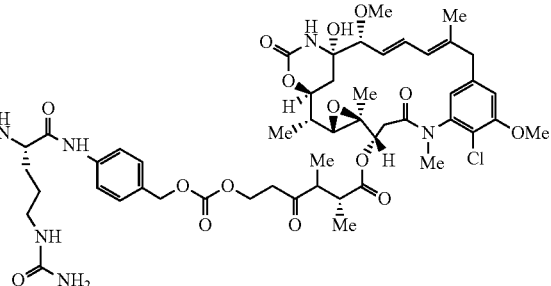
I24
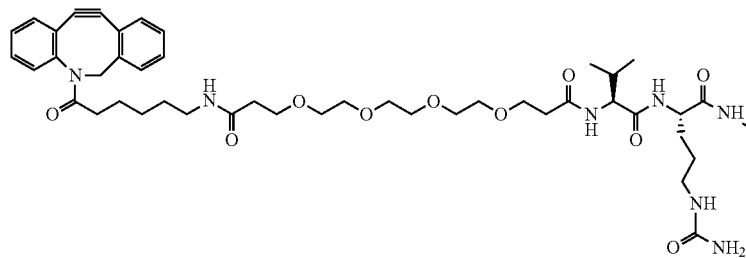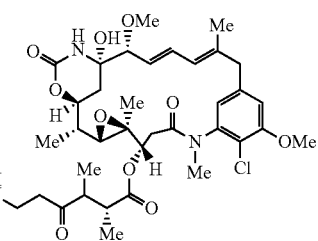
I25
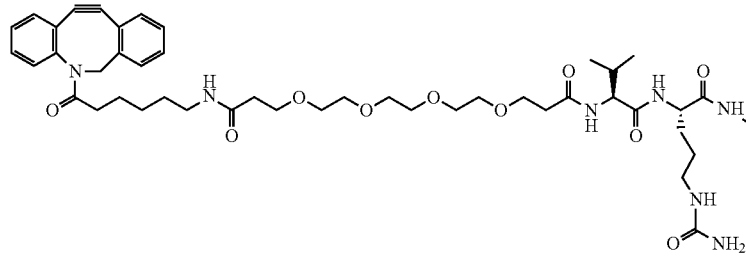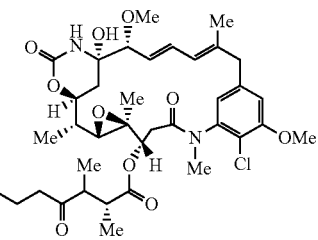
I26
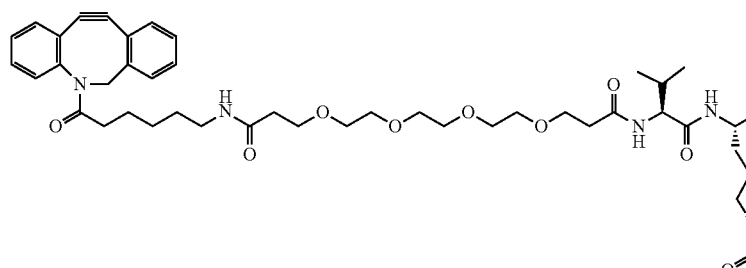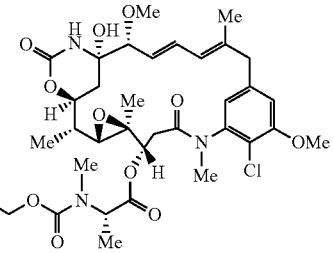
I27
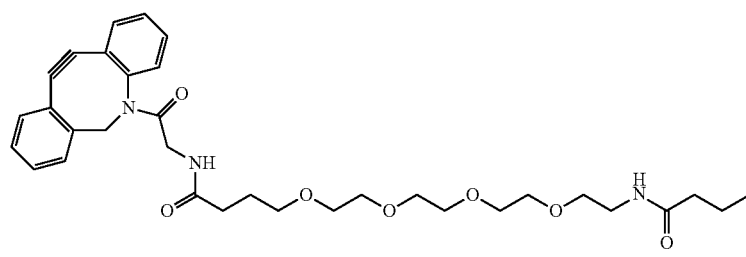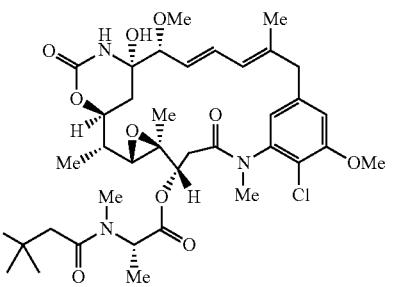
I28

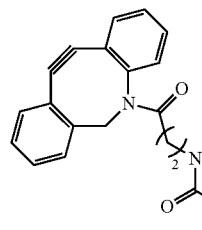 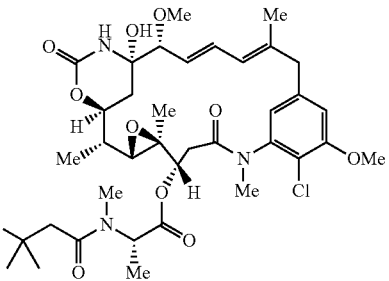
I29
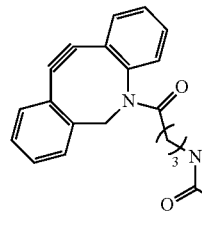 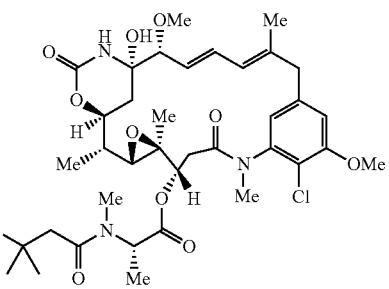
I30
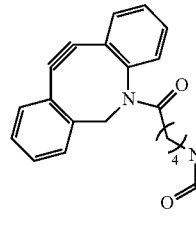 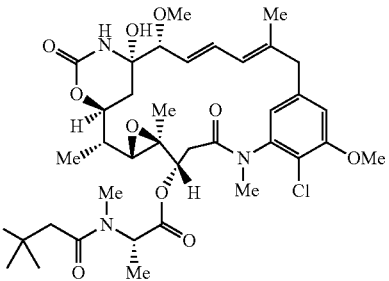
I31
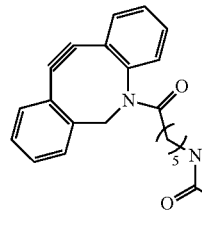 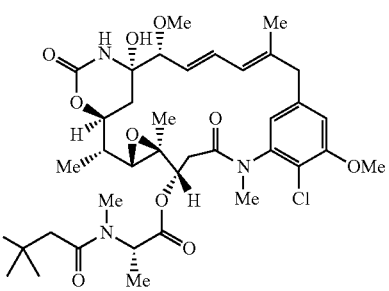
I32
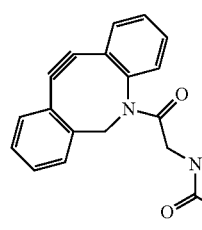 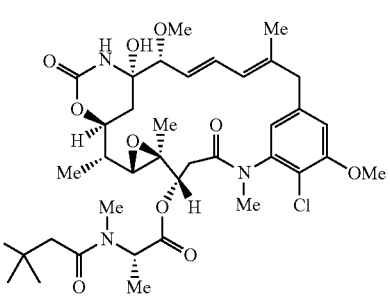
I33

-continued
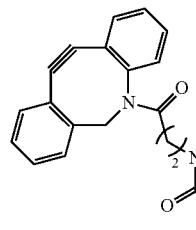 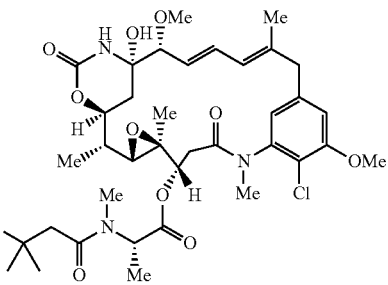
I34
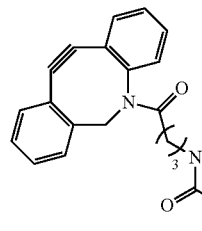 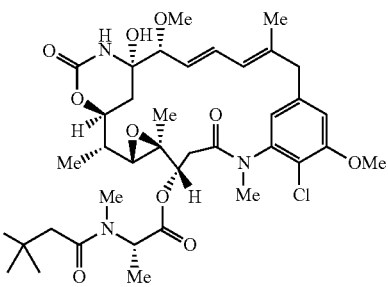
I35
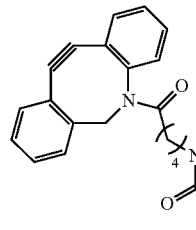 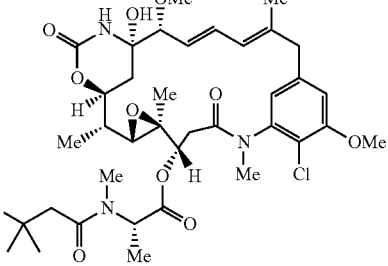
I36
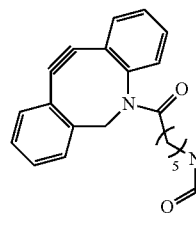 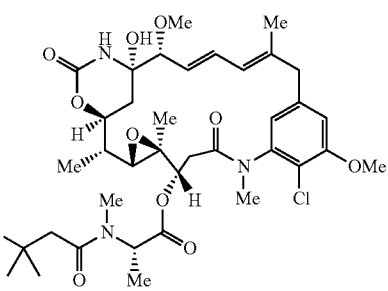
I37
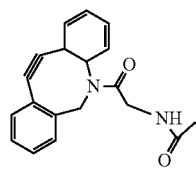 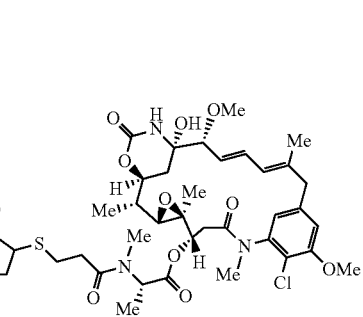
I38

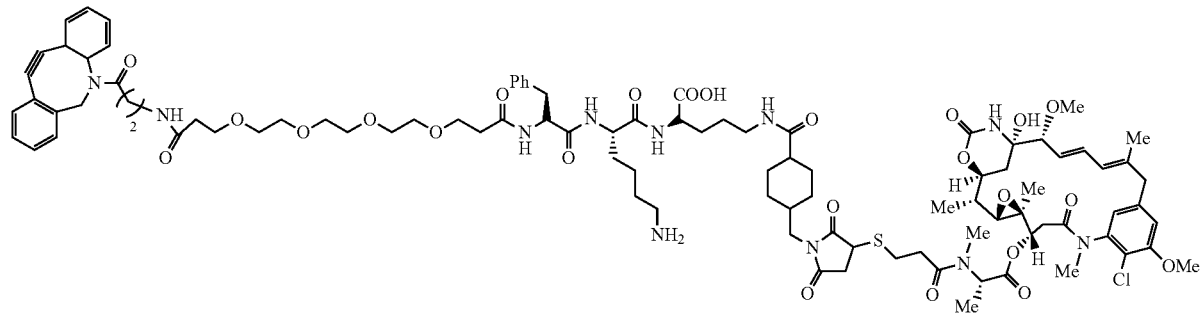
I39
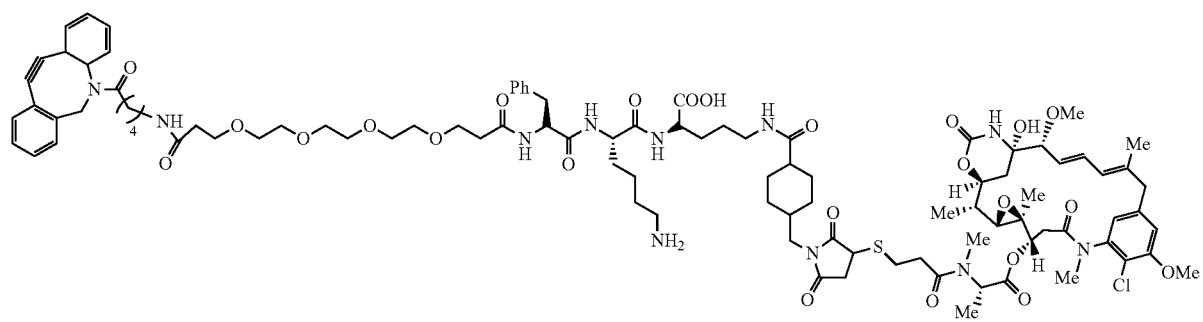
I40
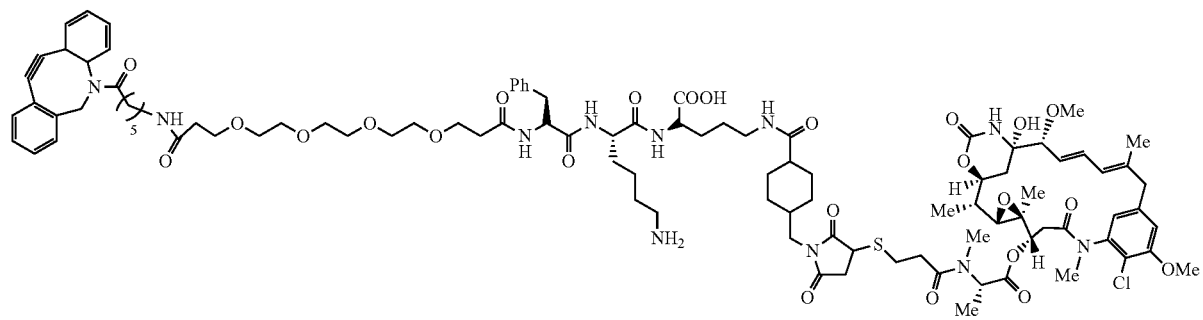
I41
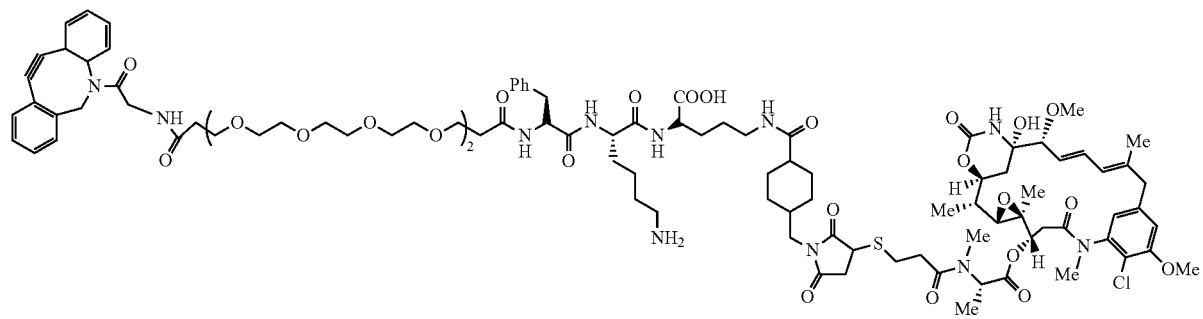
I42

-continued
I43
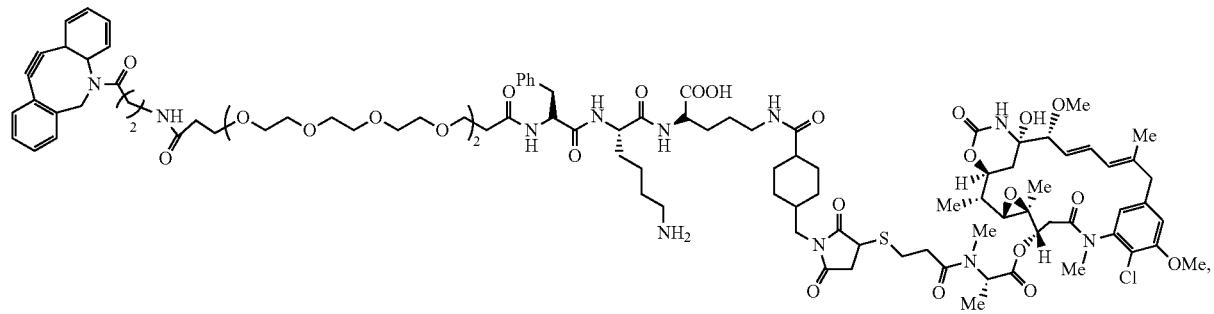
I44
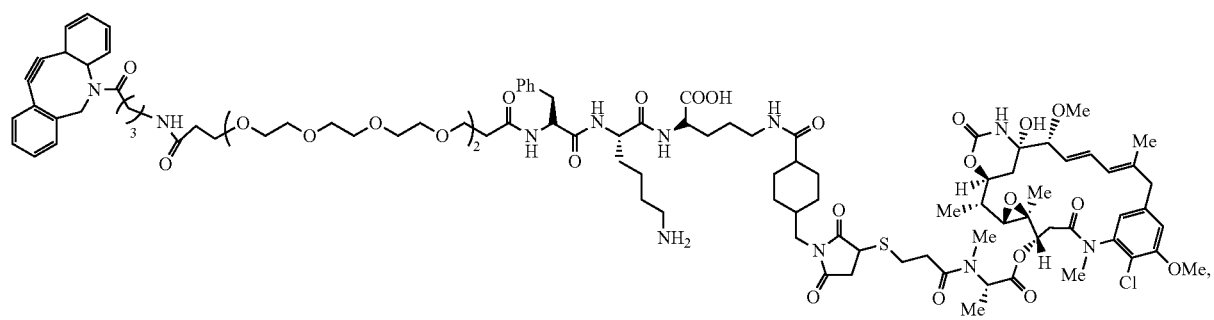
I45
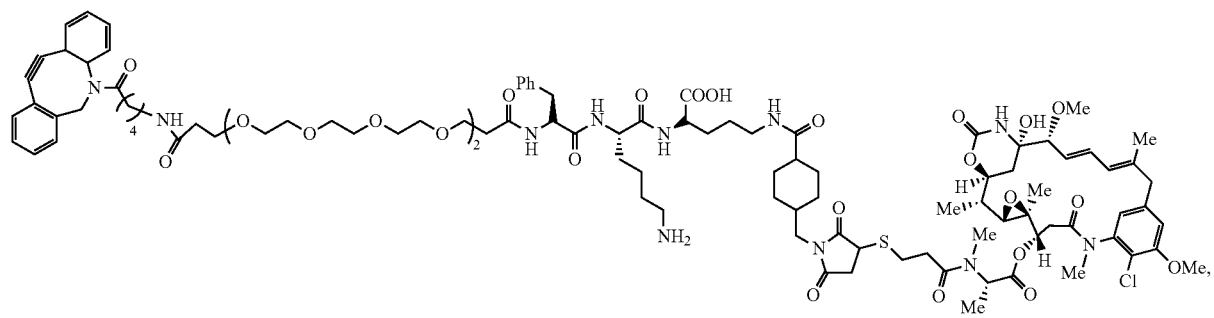
I46
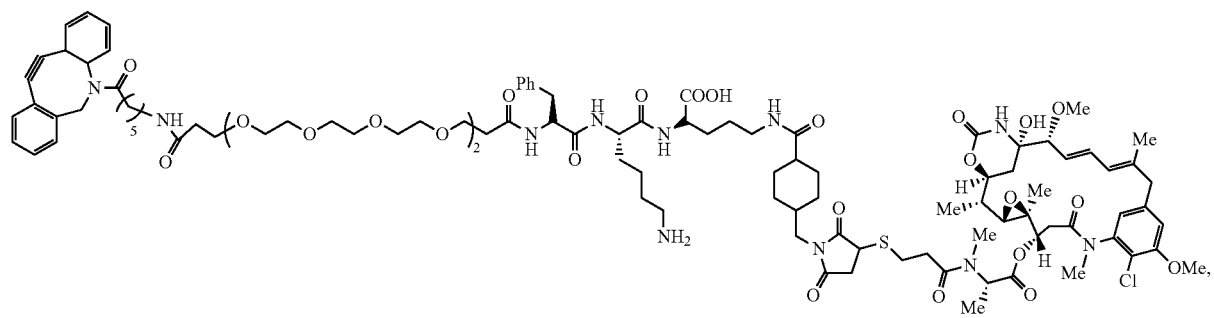

I47
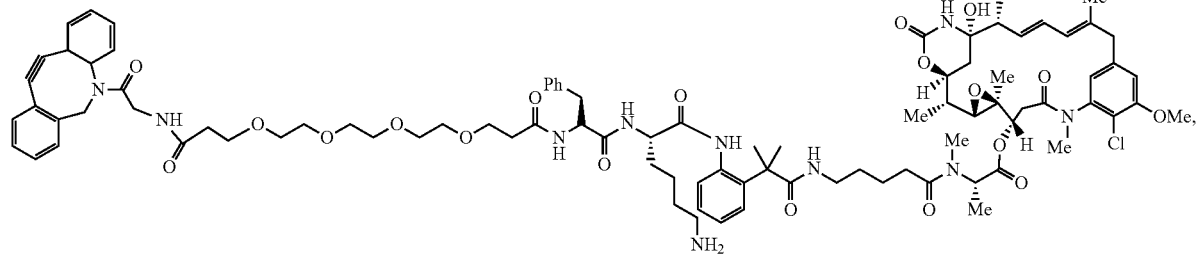
I48
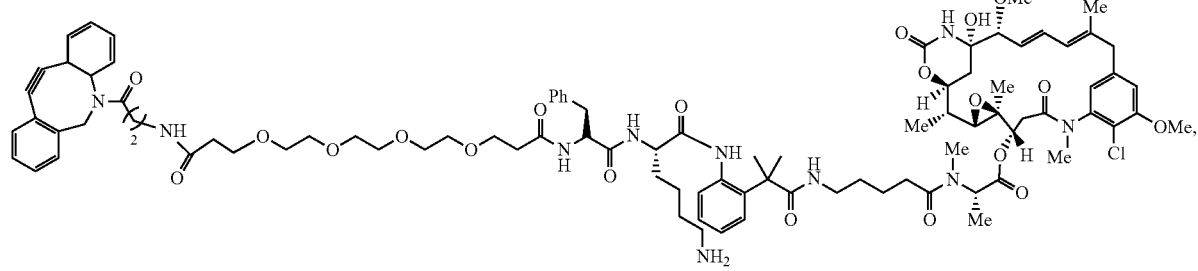
I49
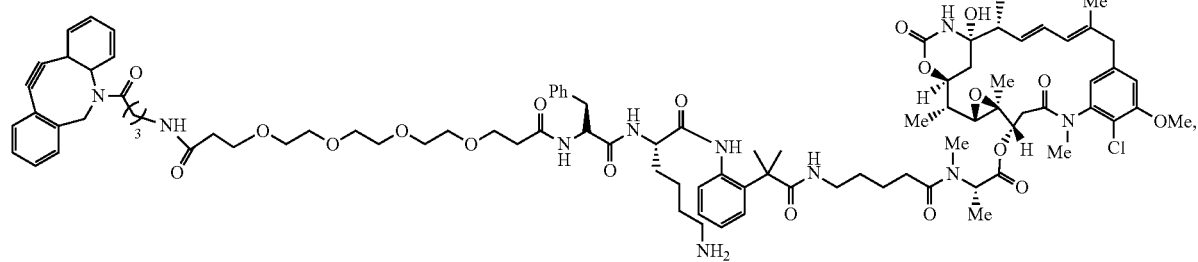
I50
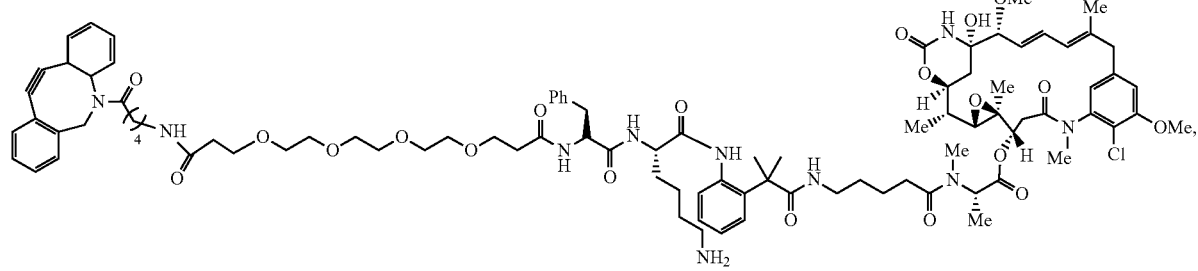
I51
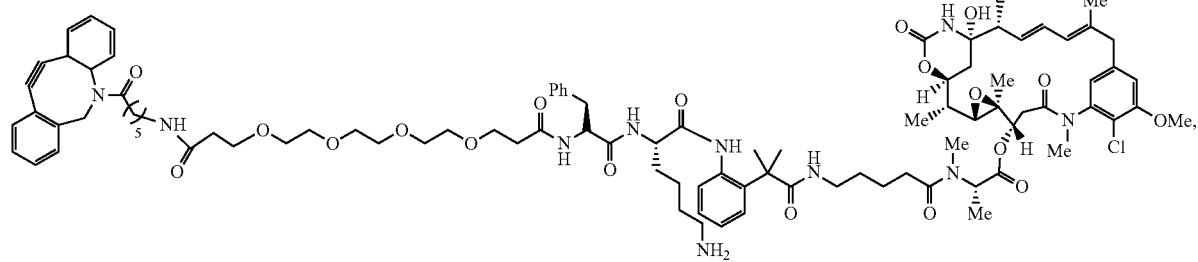

I52
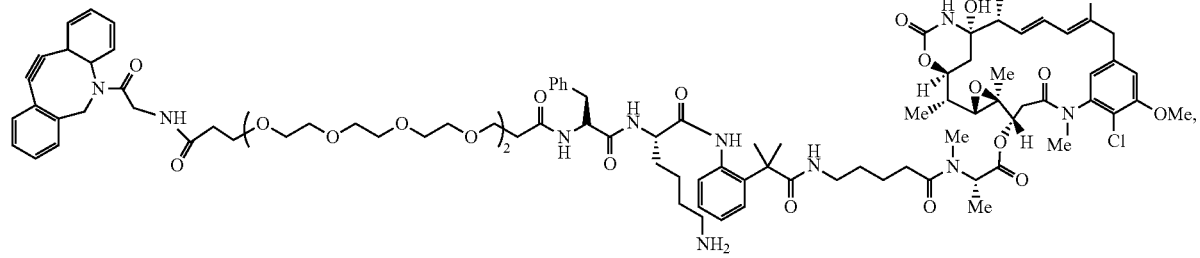
I53
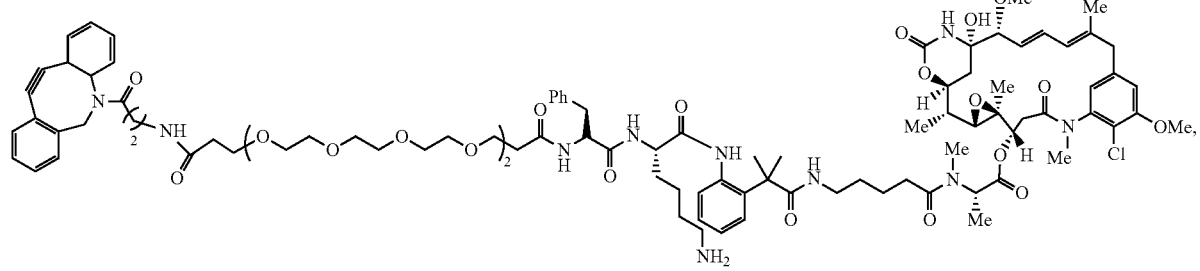
I54
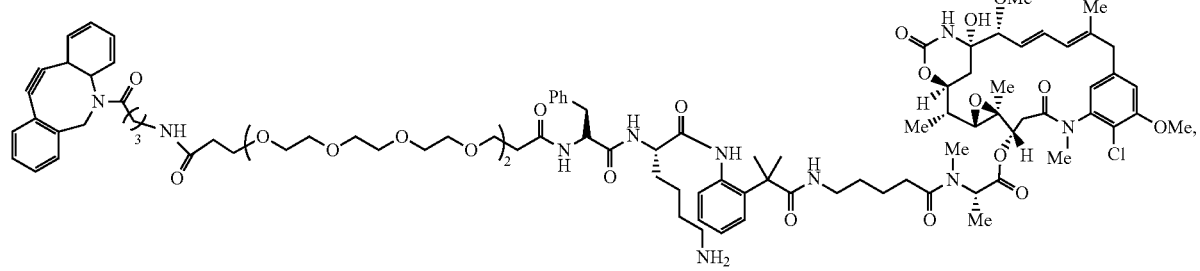
I55
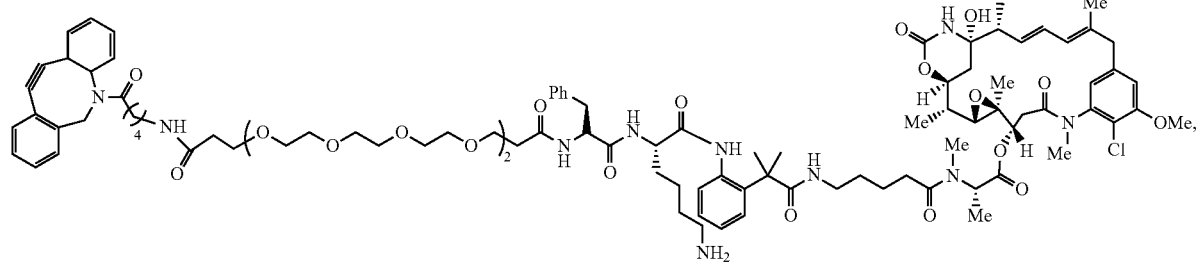
I56
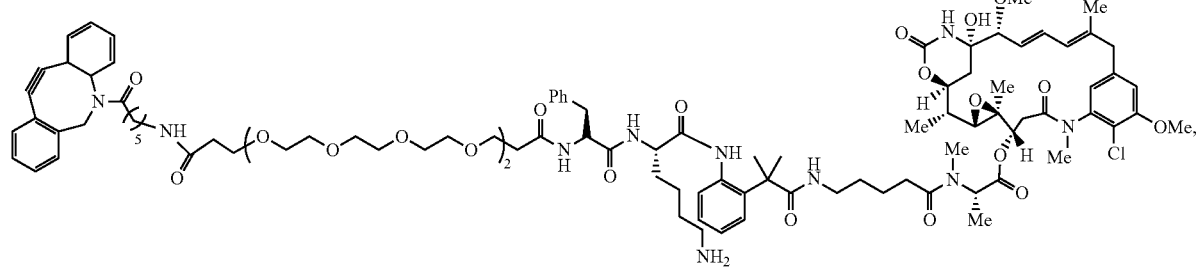

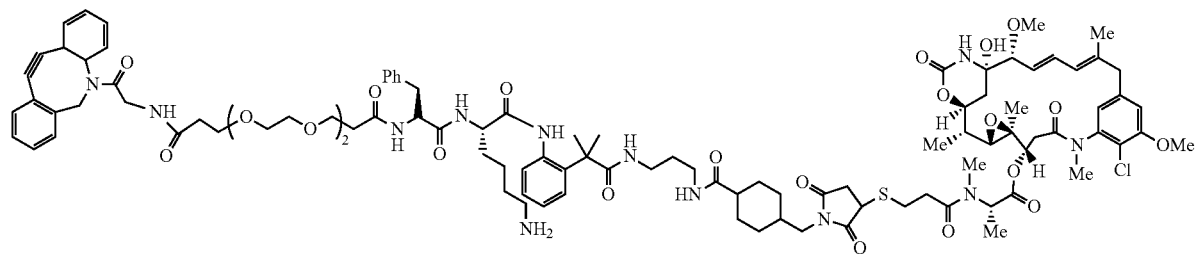
I57
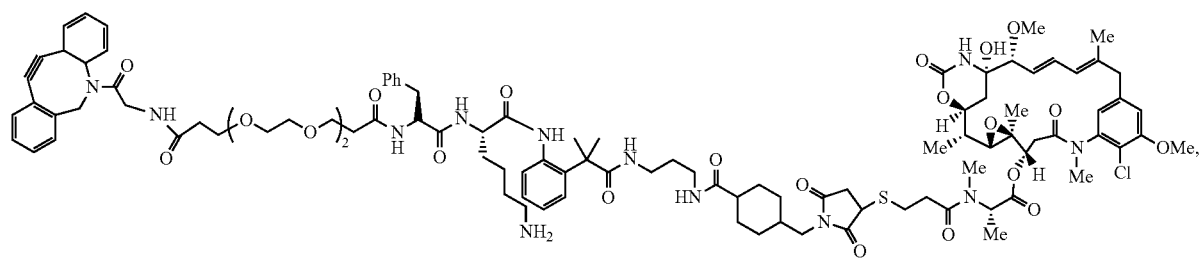
I58
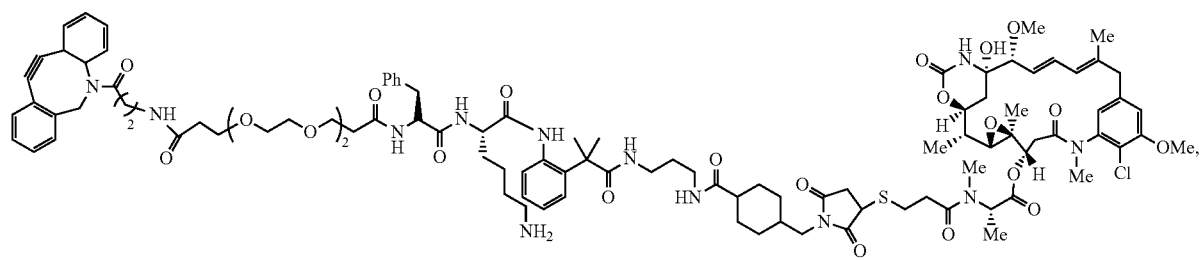
I59
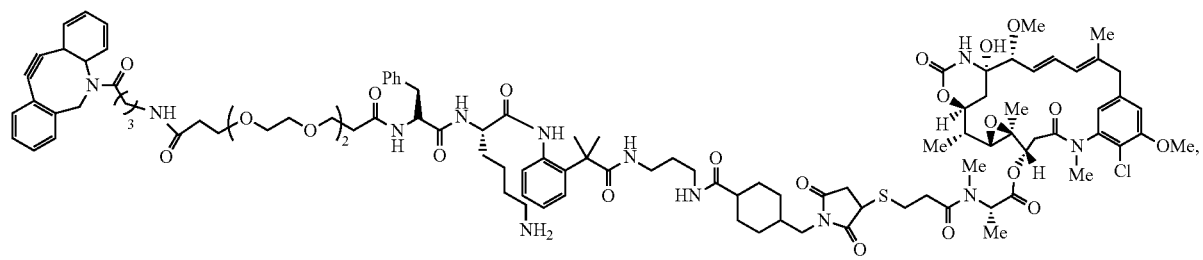
I60
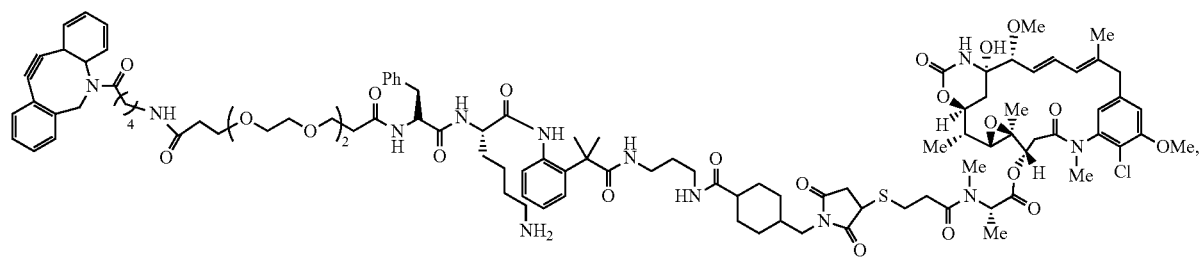
I61

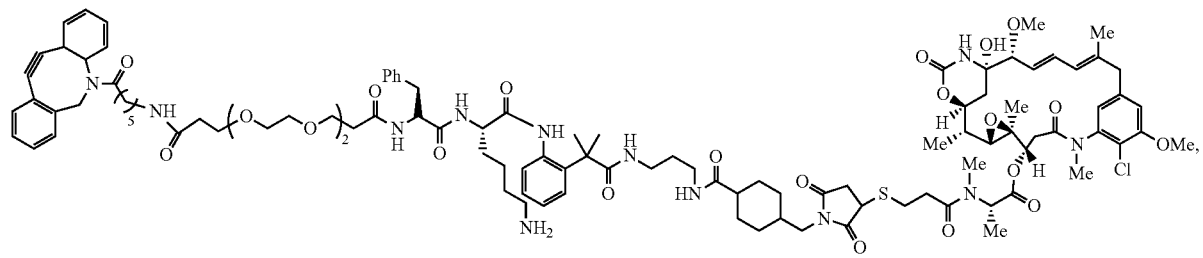
I62
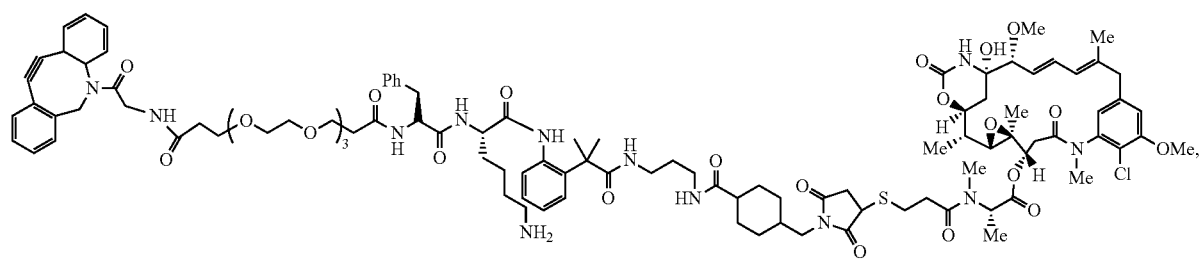
I63
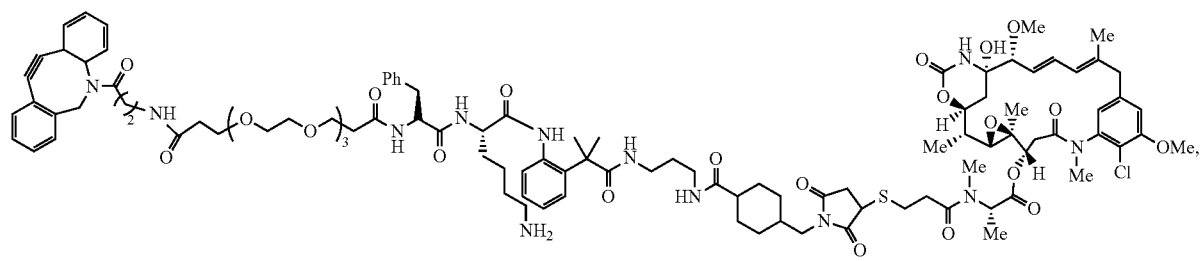
I64
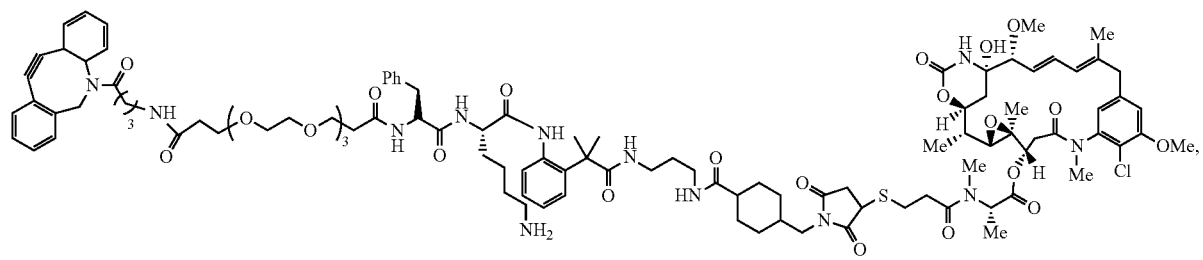
I65
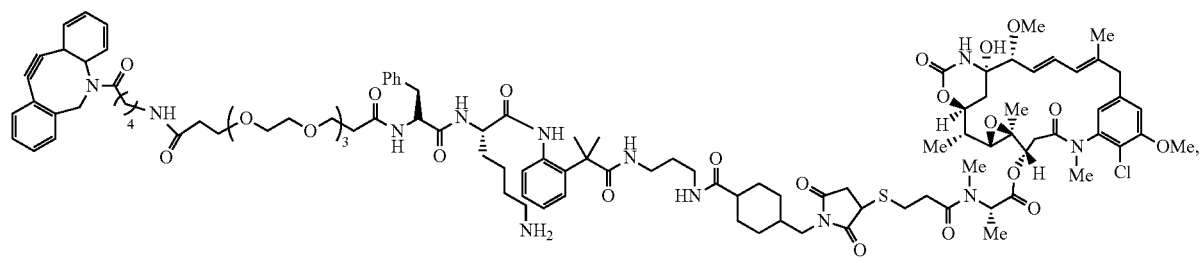
I66

-continued
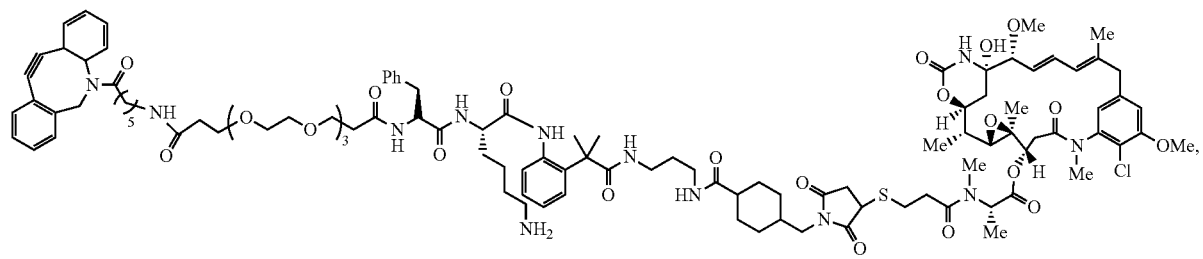
I67
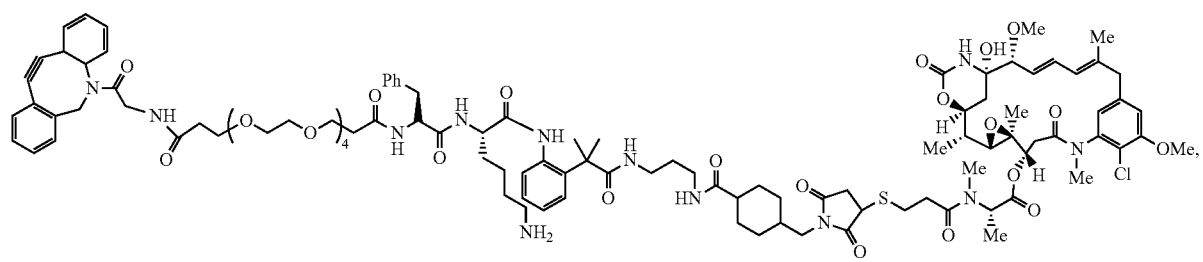
I68
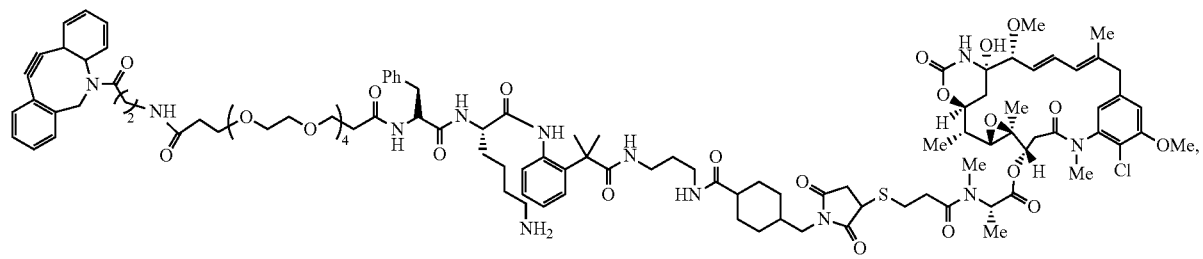
I69
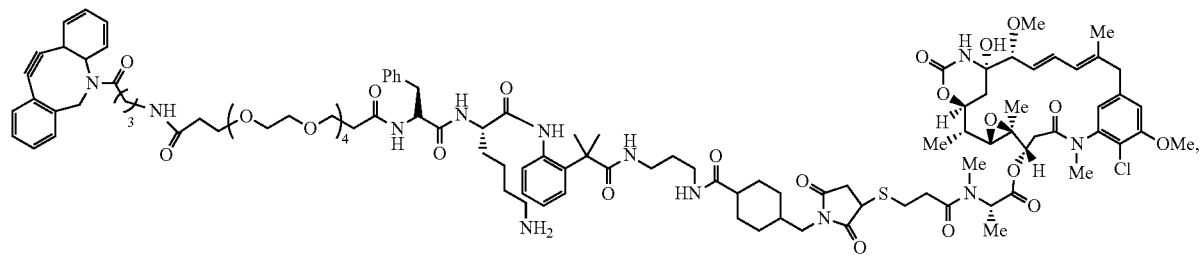
I70
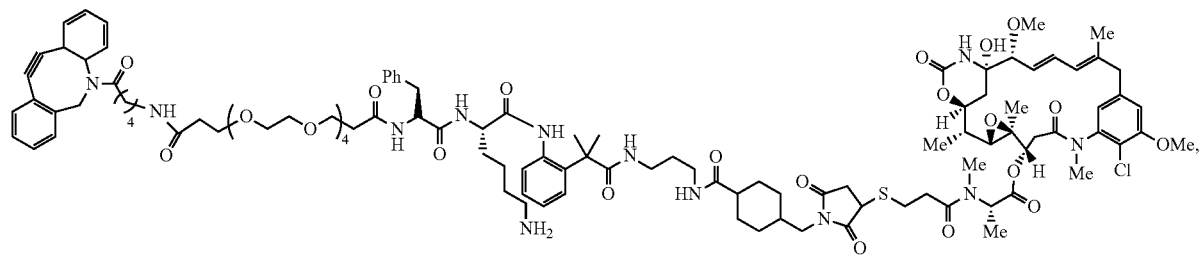
I71

-continued
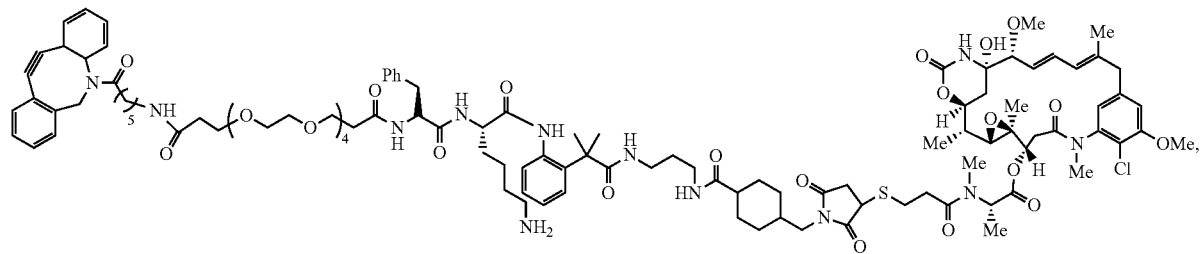
I72
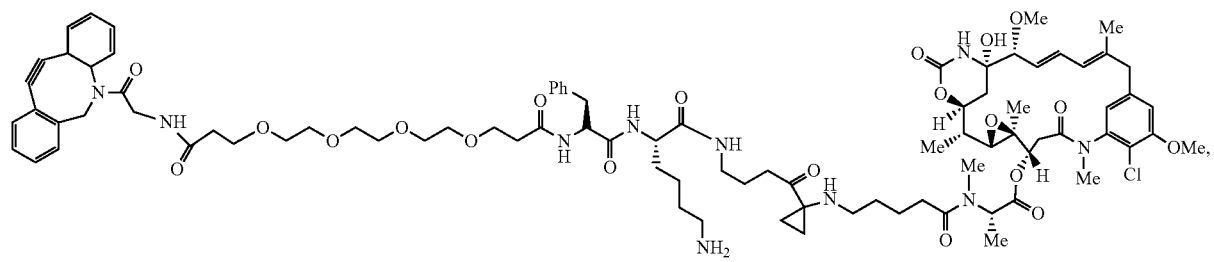
I73
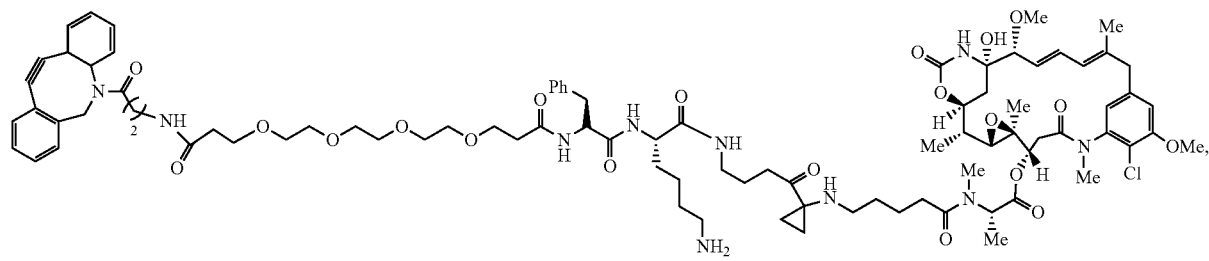
I74
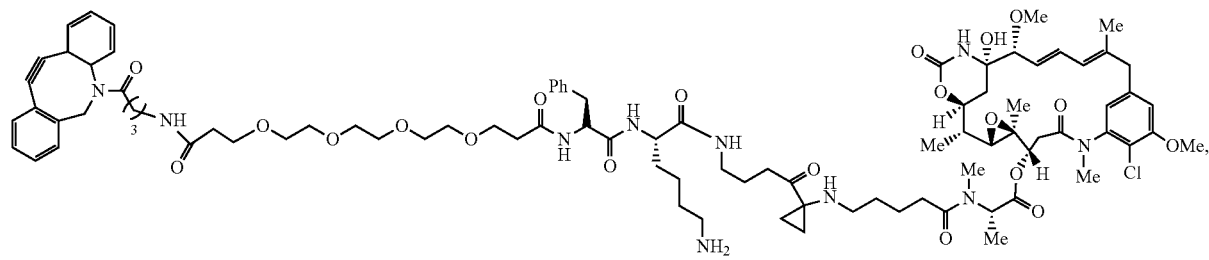
I75
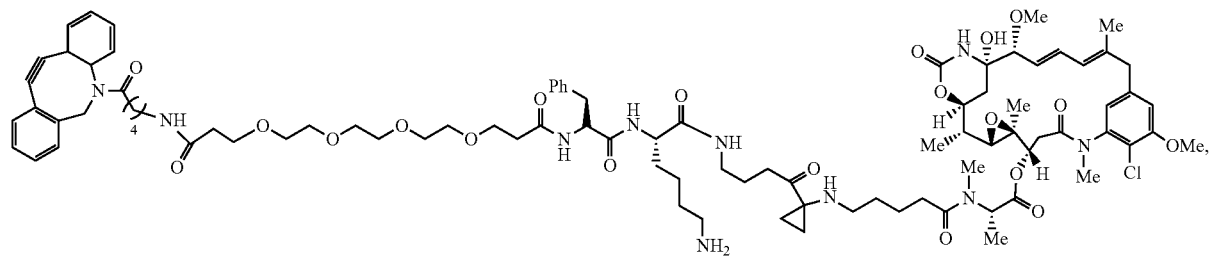
I76

-continued
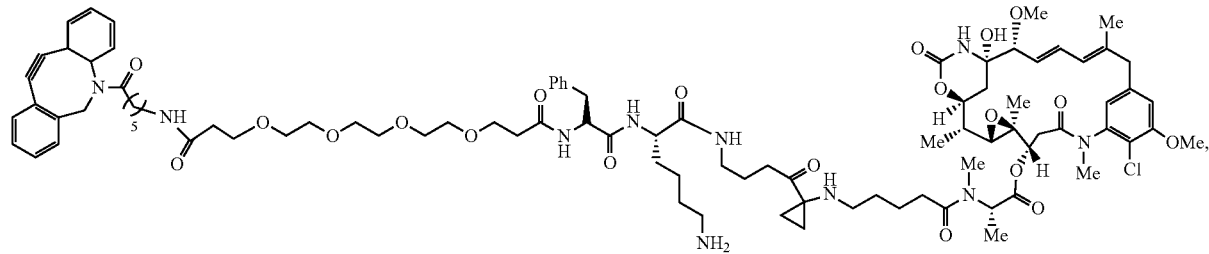
I77
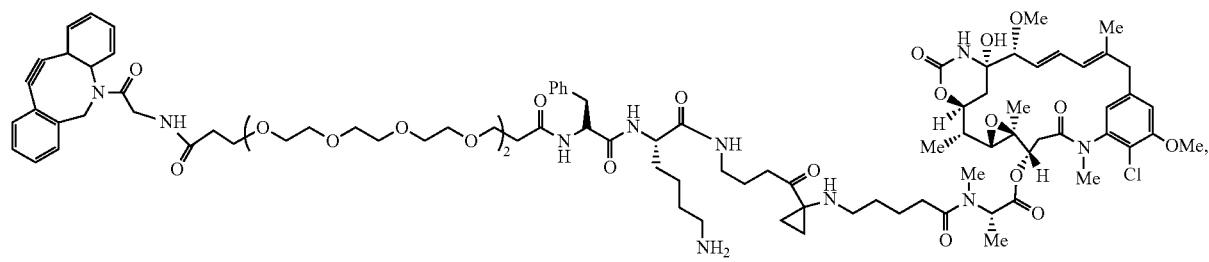
I78
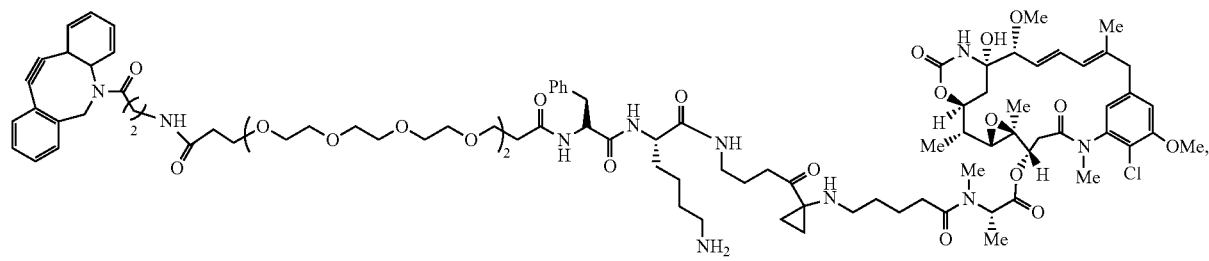
I79
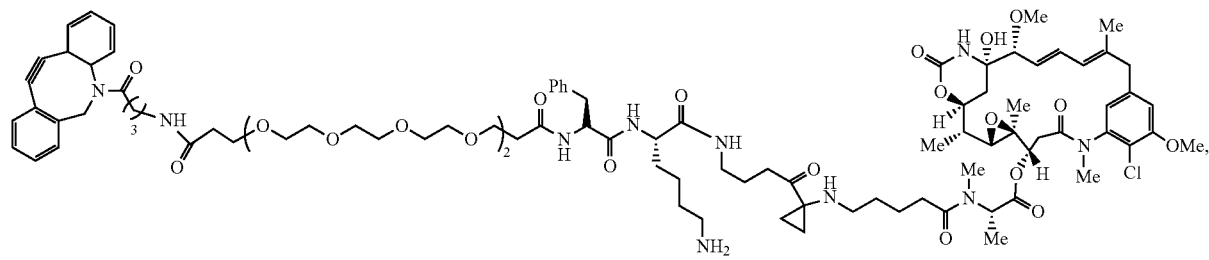
I80
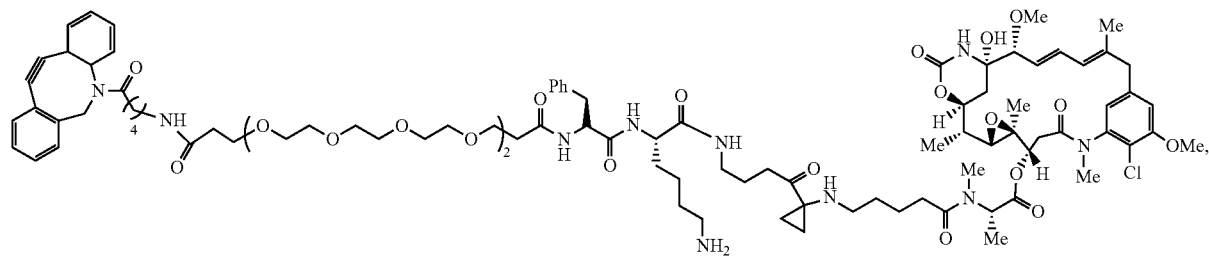
I81

-continued
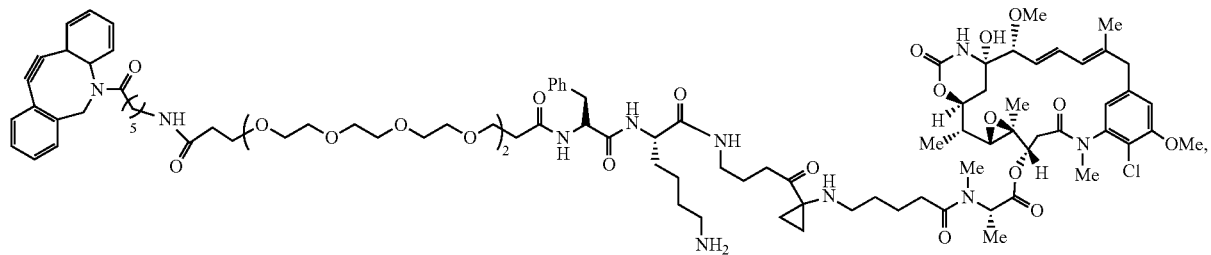
I82
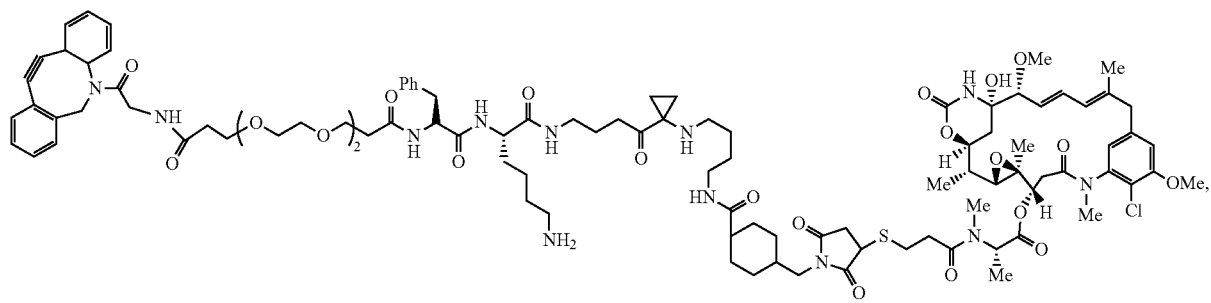
I83
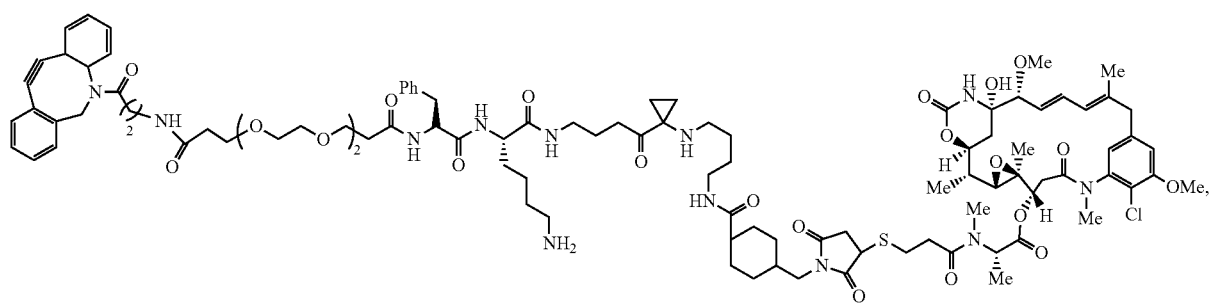
I84
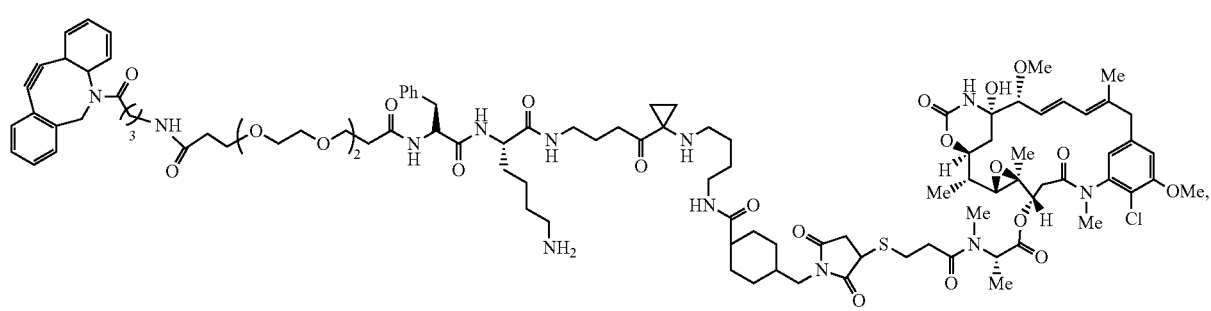
I85
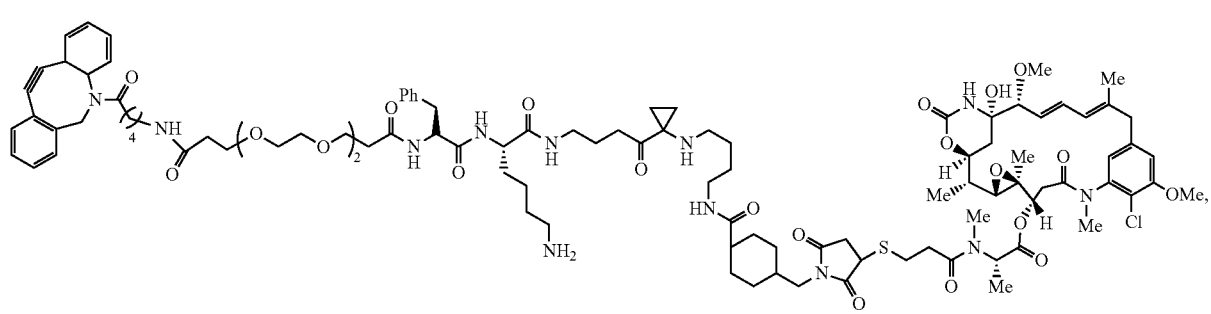
I86

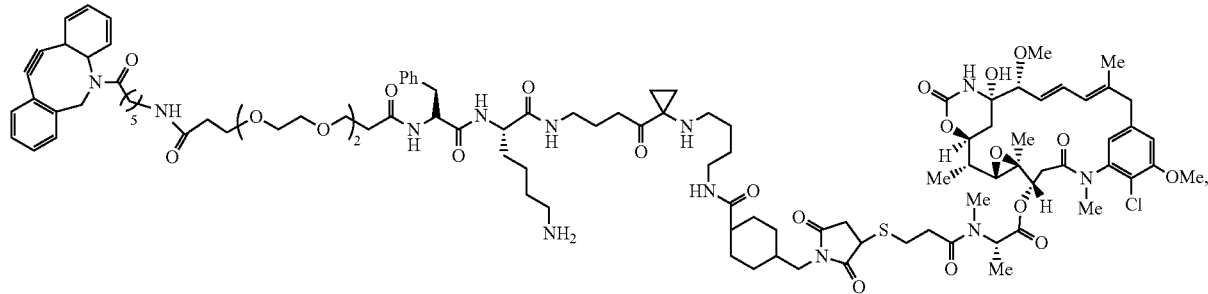
I87
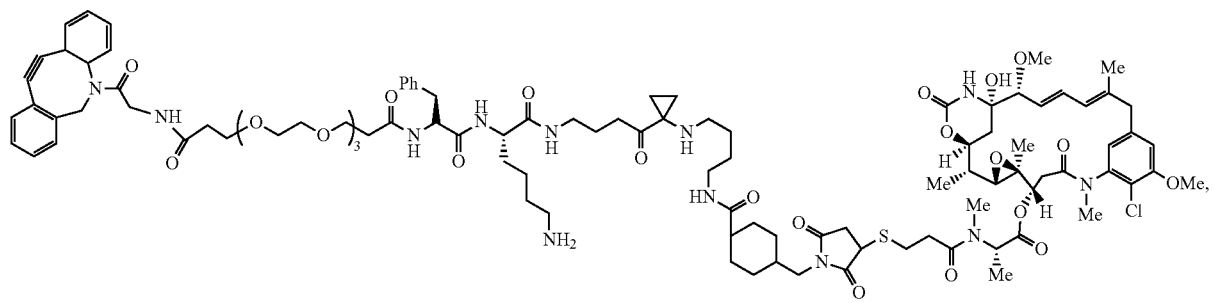
I88
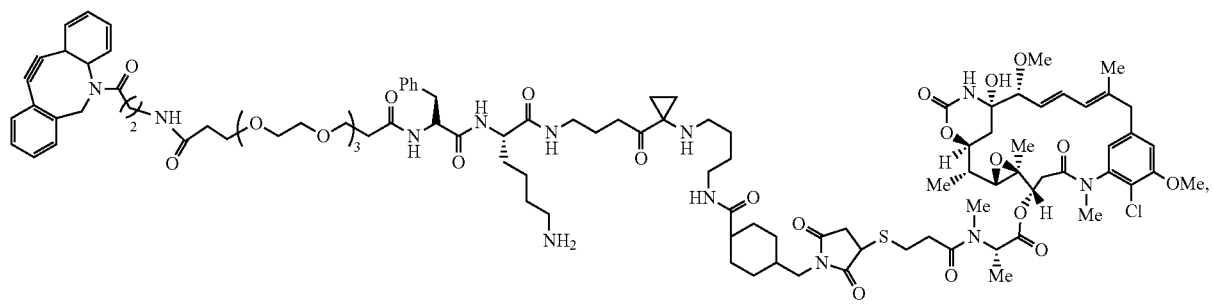
I89
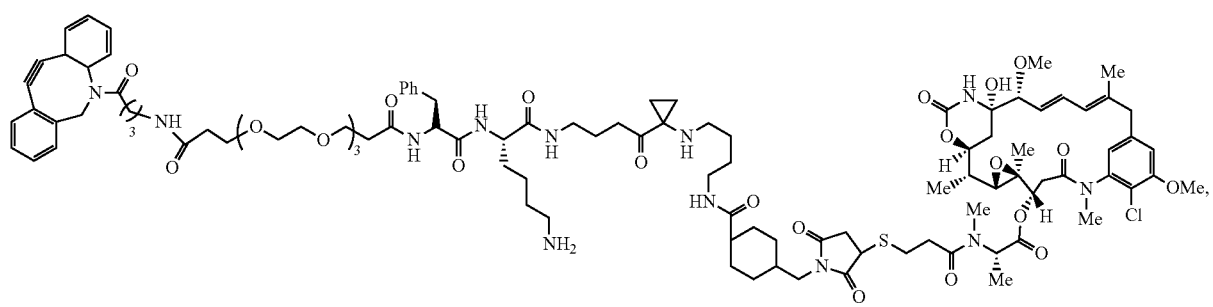
I90
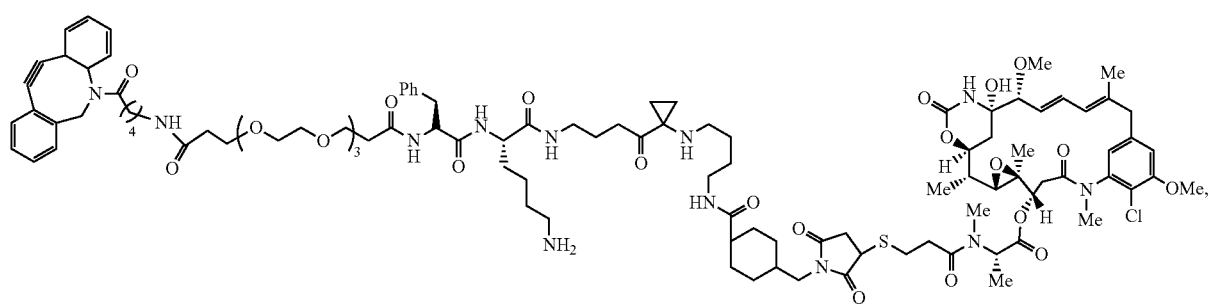
I91

-continued
I92
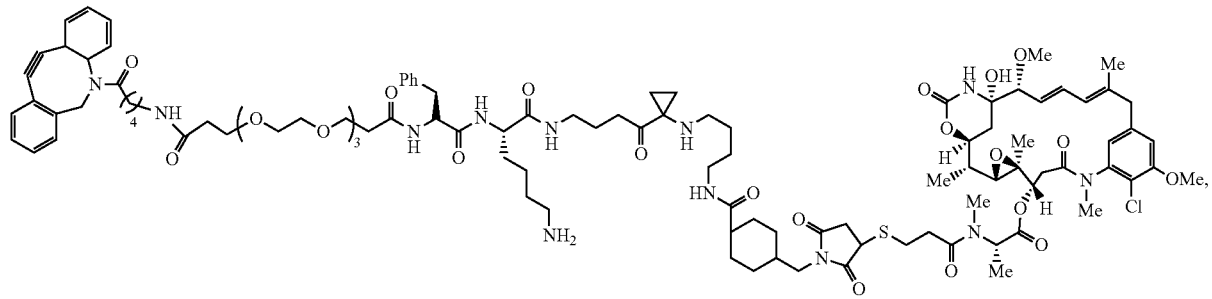
I93
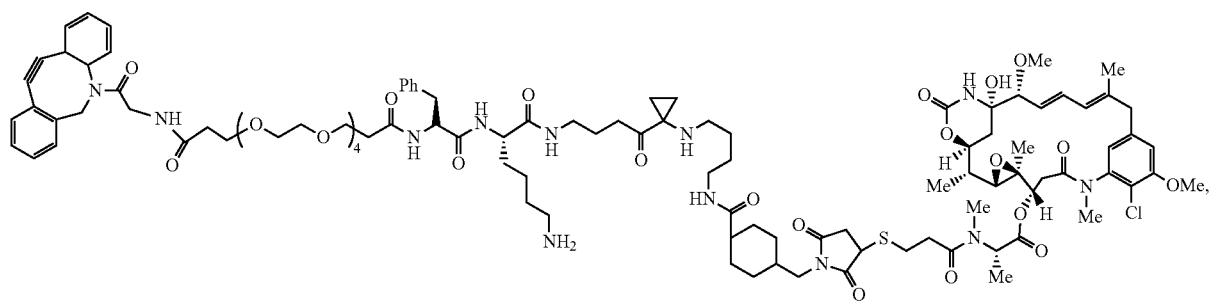
I94
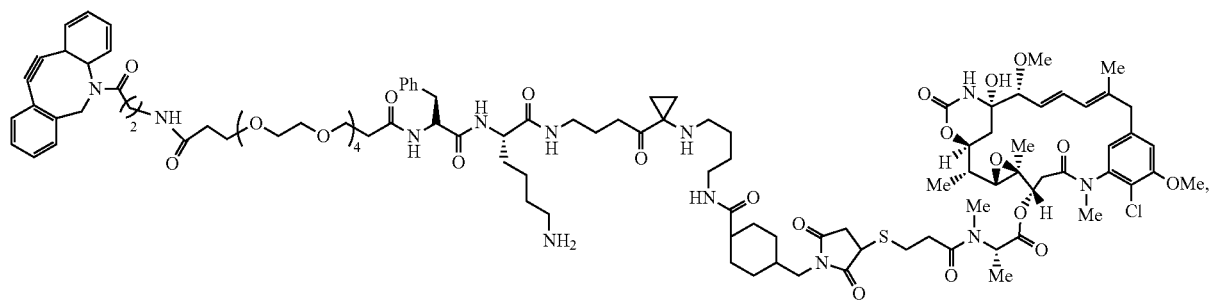
I95
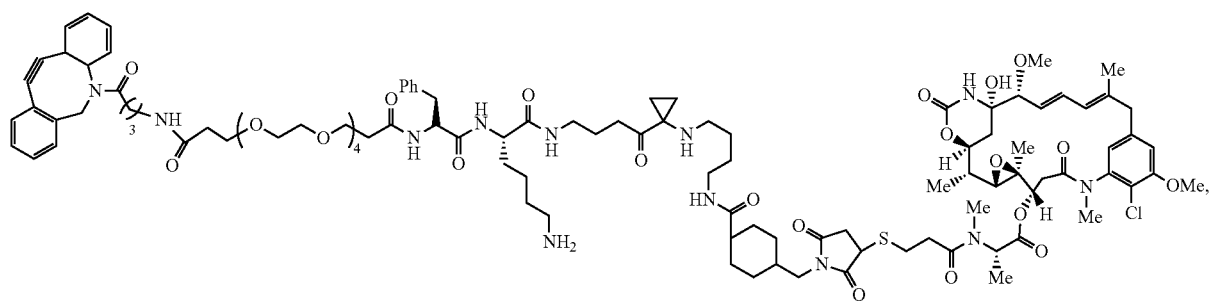
I96
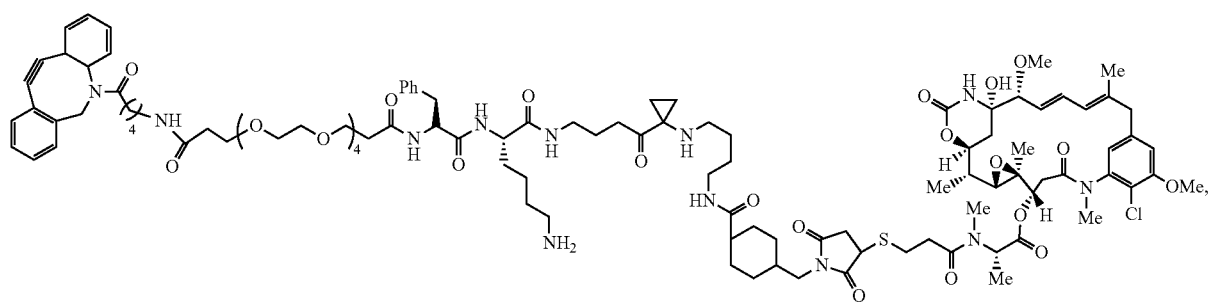

I97
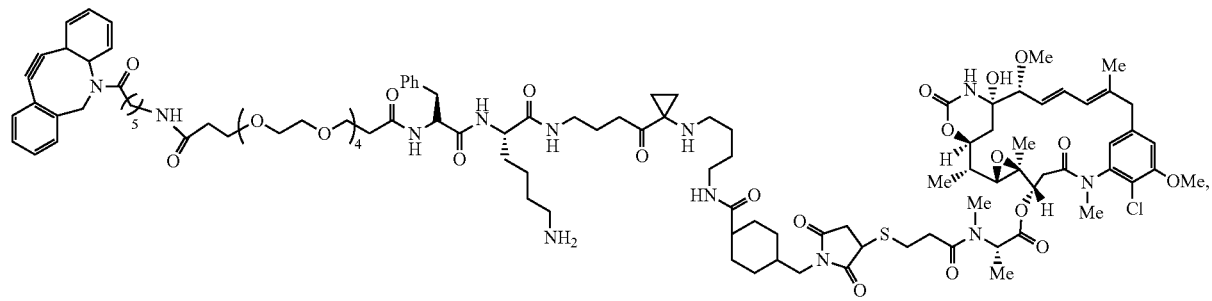
I98
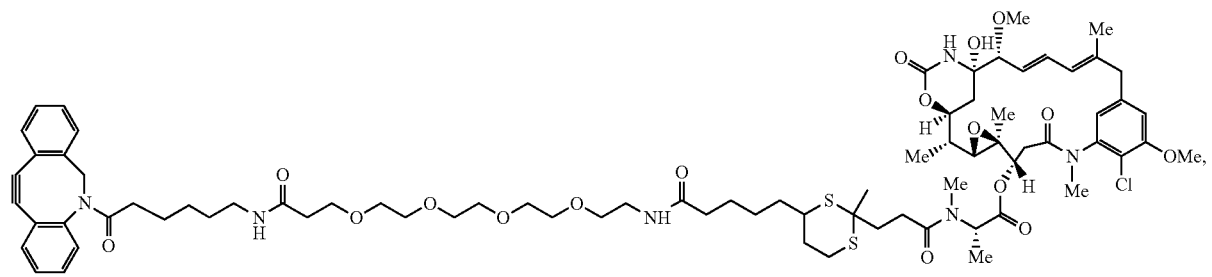
I99
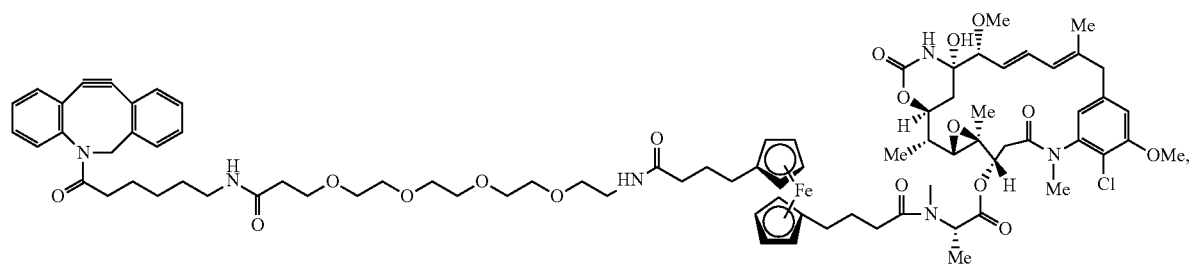
I100
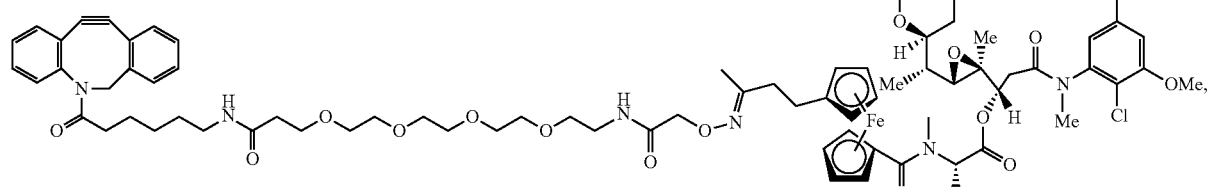
I101
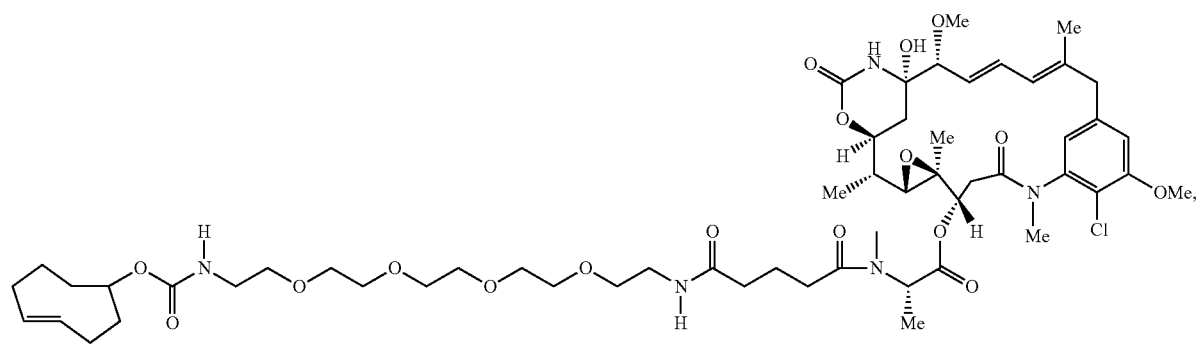

-continued
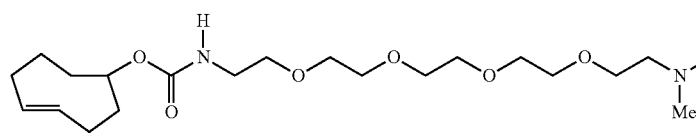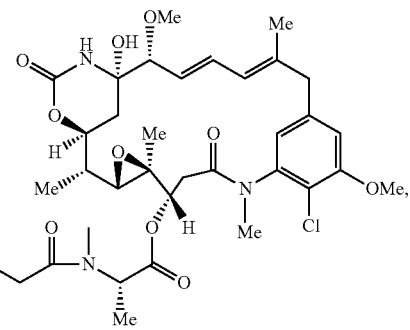
I102
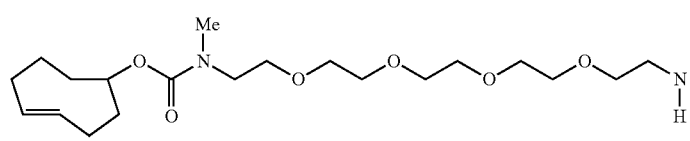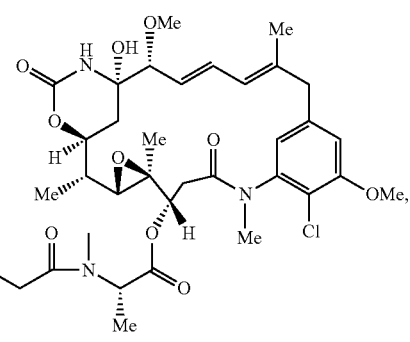
I103
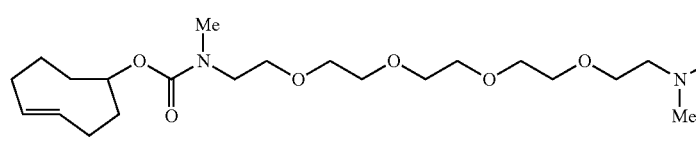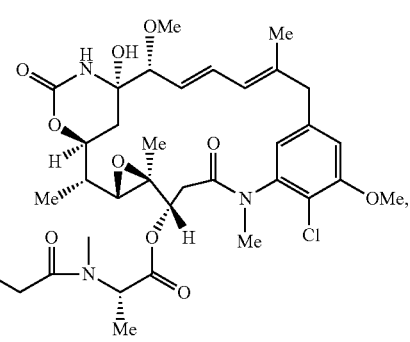
I104
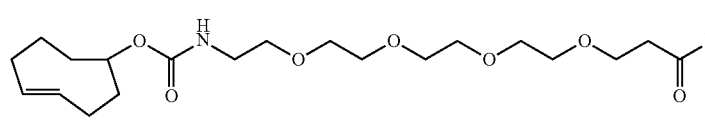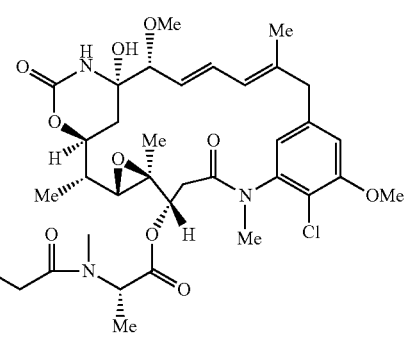
I105

Formula II

The present invention provides compounds of Formula II as follows:

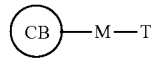

Formula II

Wherein CB is a cell-binding agent; M is a non-natural amino acid; and T is an azide group or a tetrazine group.

In certain embodiments, M has the following structure:

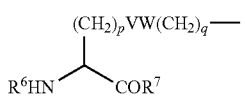

Formula IV wherein:

p and q are each independently an integer from 0-10;

$R^6$ is H, amino acid, polypeptide, or amino terminus modification group, or a bond;

$R^7$ is OH, amino acid, polypeptide, or carboxy terminus modification group, or a bond;

V is an alkyl, aryl, carbocycle, heterocycle, or absent; and,

W is O, N, S, or absent; provided that when $R^6$ is a bond, the non-natural amino acid is connected to the cell-binding agent via $R^6$, and when $R^7$ is a bond, the non-natural amino acid is connected to the cell-binding agent via $R^7$.

In some embodiments, p and q are each independently an integer from 0-8. In some embodiments, p and q are each independently an integer from 0-6. In some embodiments, p and q are each independently an integer from 0-4. In some embodiment, p and q are each independently an integer from 0-2.

In non-limiting exemplary embodiments, M may exhibit the following structure formulae:

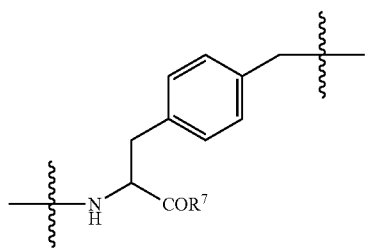

V

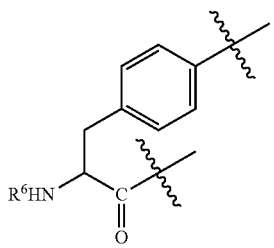

VI

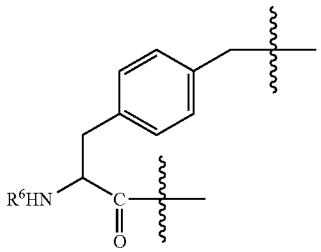

VII

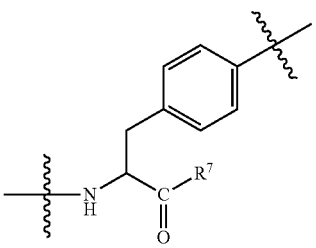

VIII

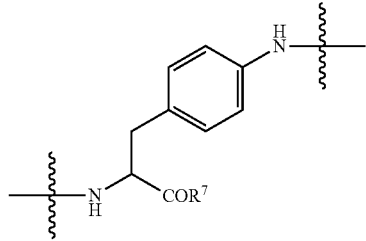

IX

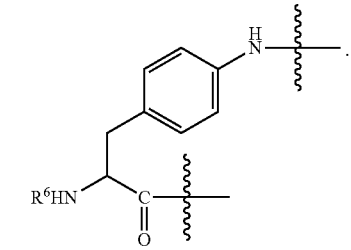

X

Non-Natural Amino Acids (M) (Moiety and Point (T) of Linker (E) Attachment)

Figure 8:
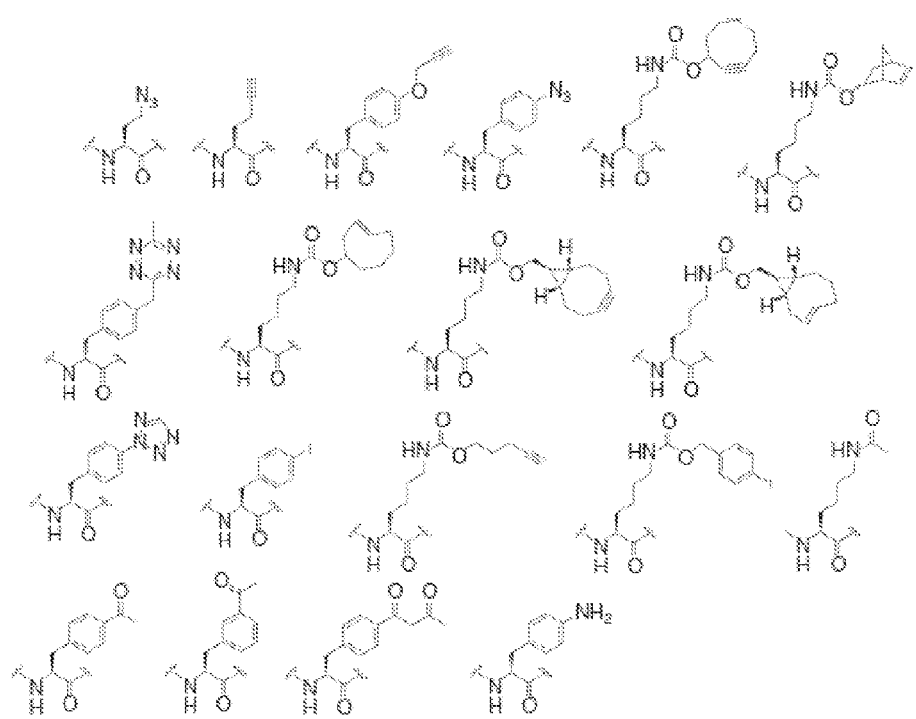
FIG. 8 shows example NNAA for employment in the present invention.
Figure 9A:
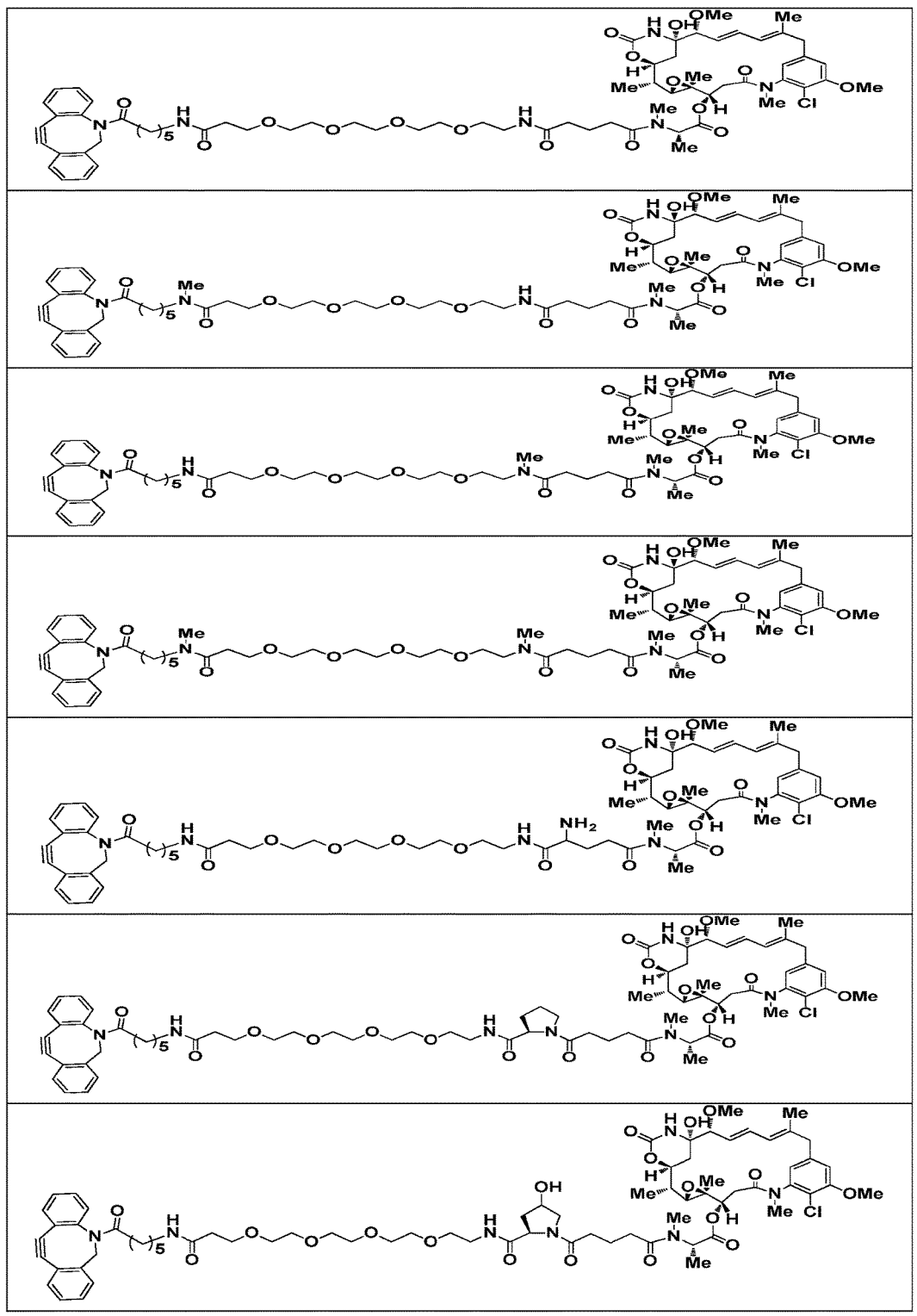
FIGS. 9A-C illustrate several example compounds of the present invention.
Figure 9B:
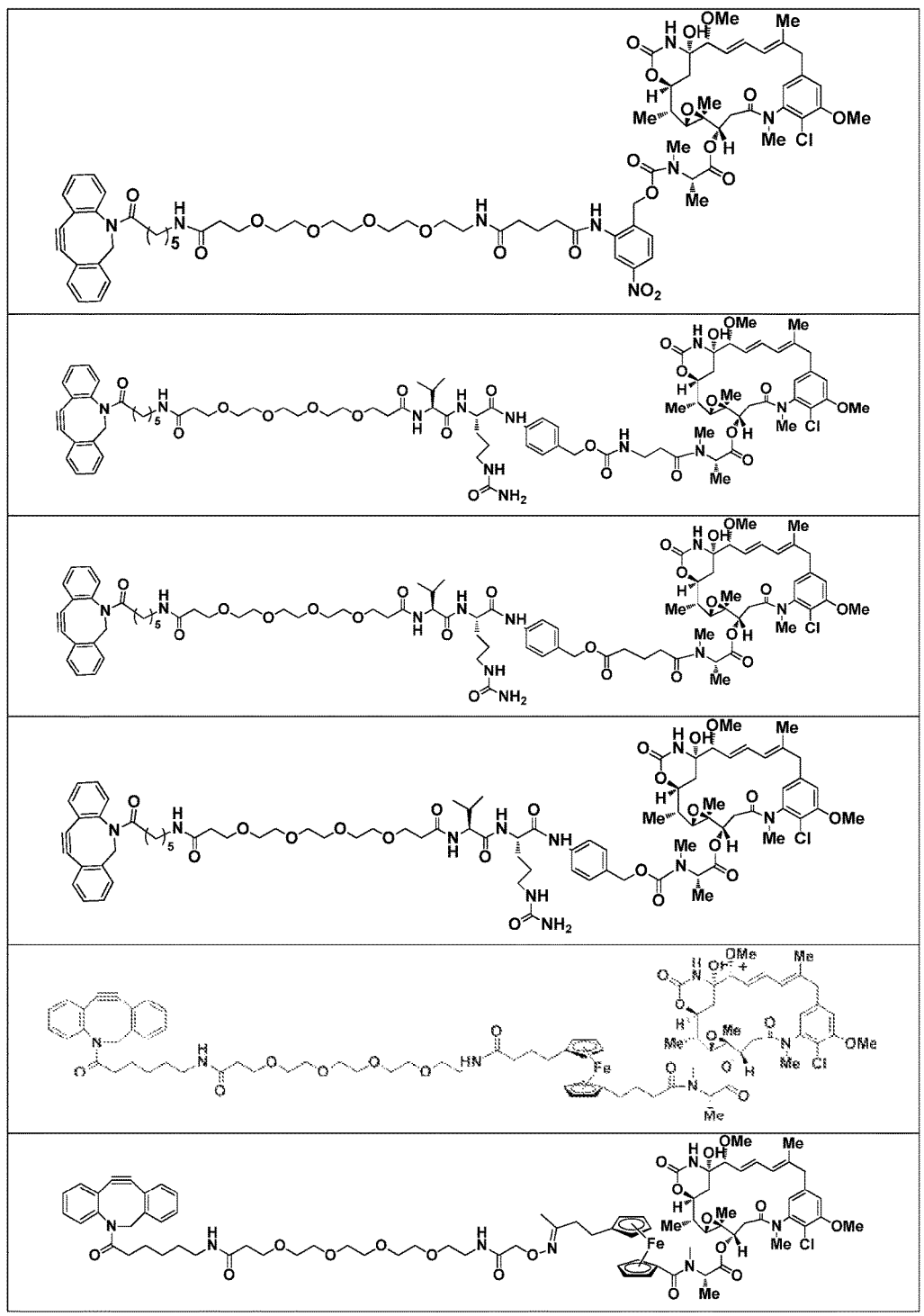
Figure 9C:
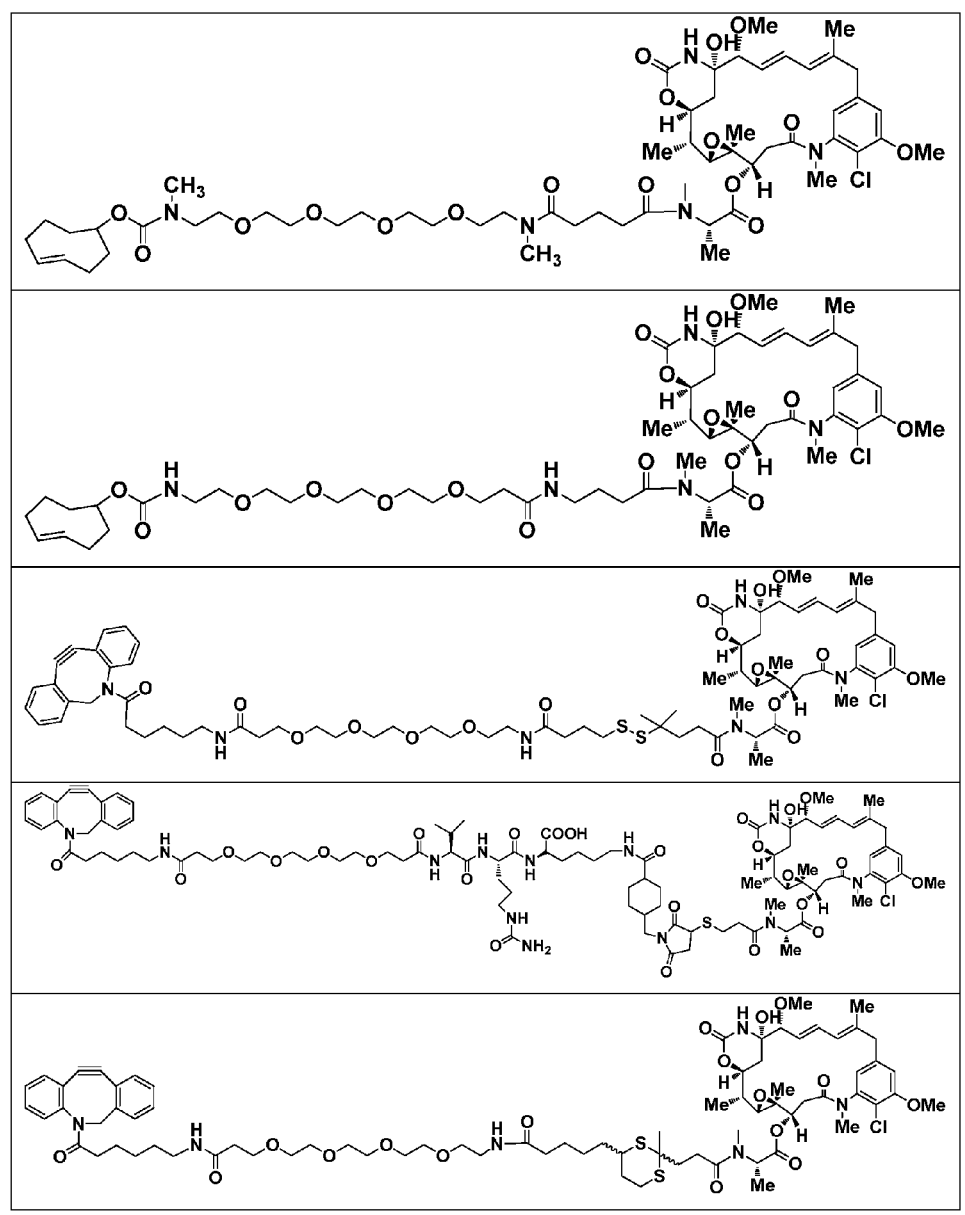
Figure 10:
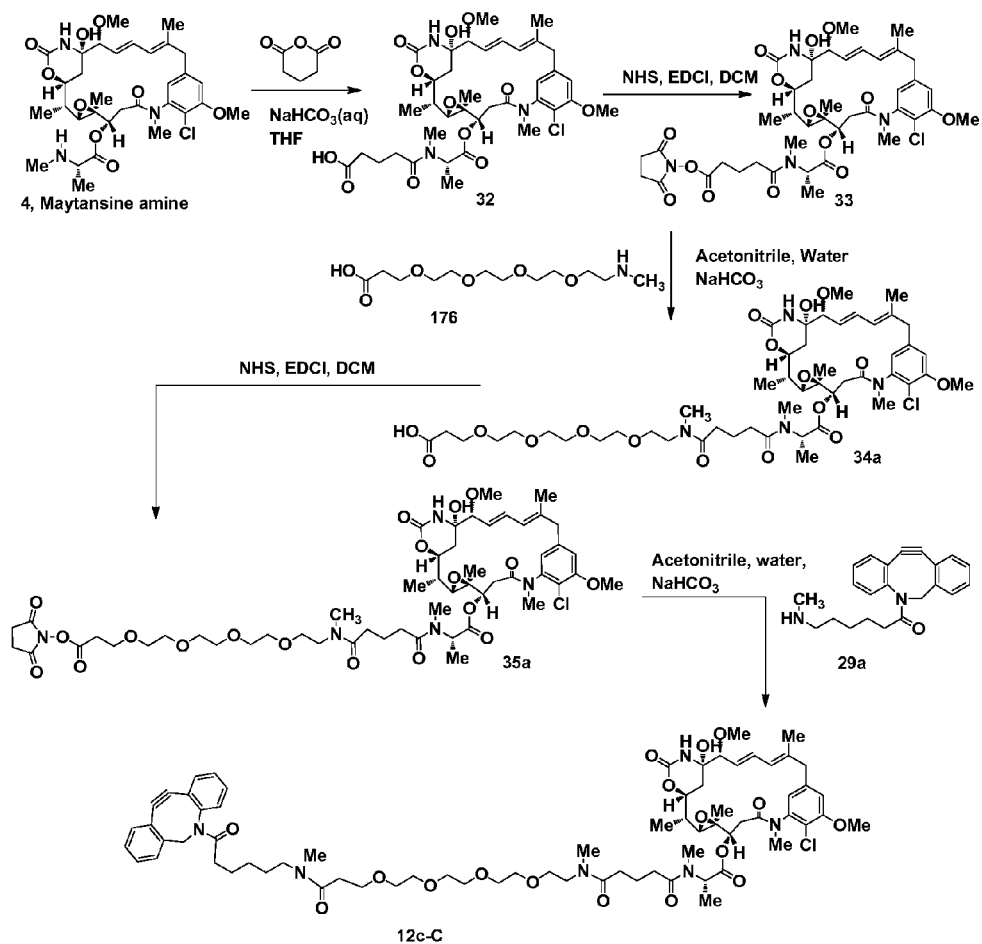
FIG. 10 illustrates an example synthetic scheme for a compound of the present invention.
Figure 11:
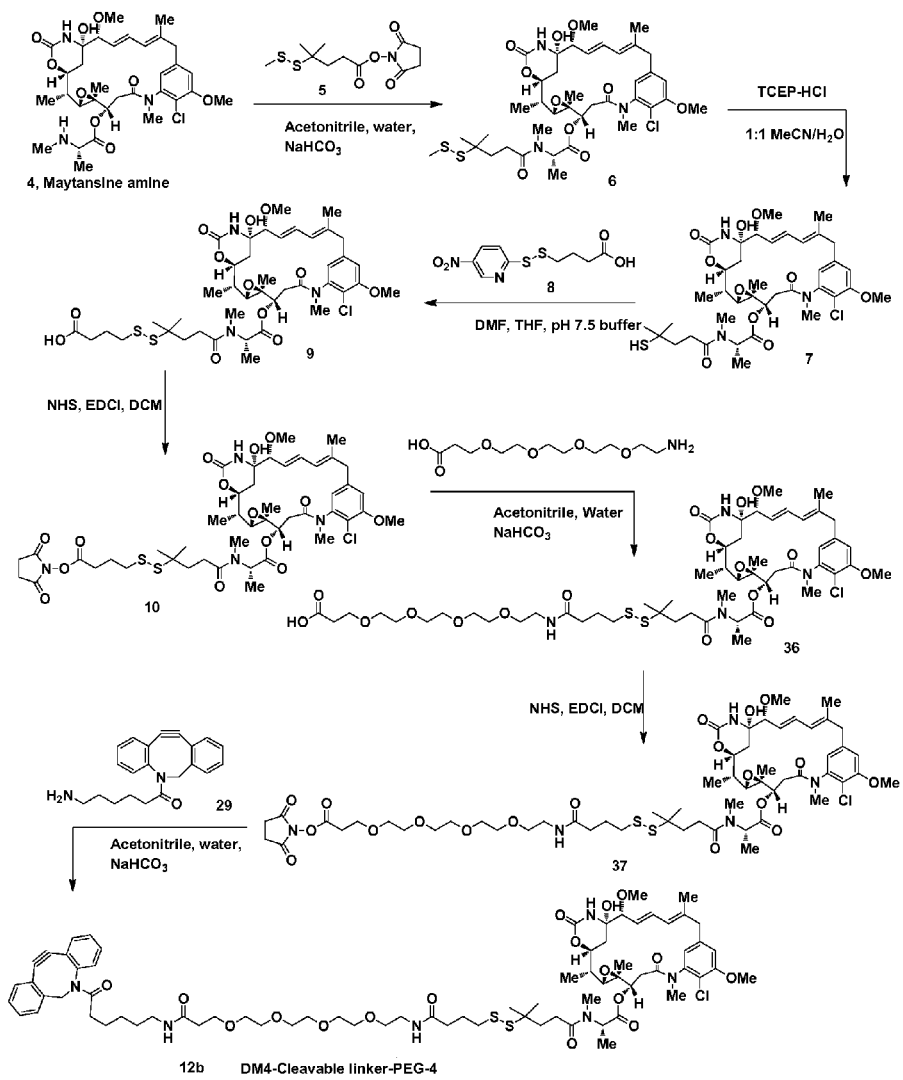
FIG. 11 illustrates an example synthetic scheme for a compound of the present invention
Figure 12:
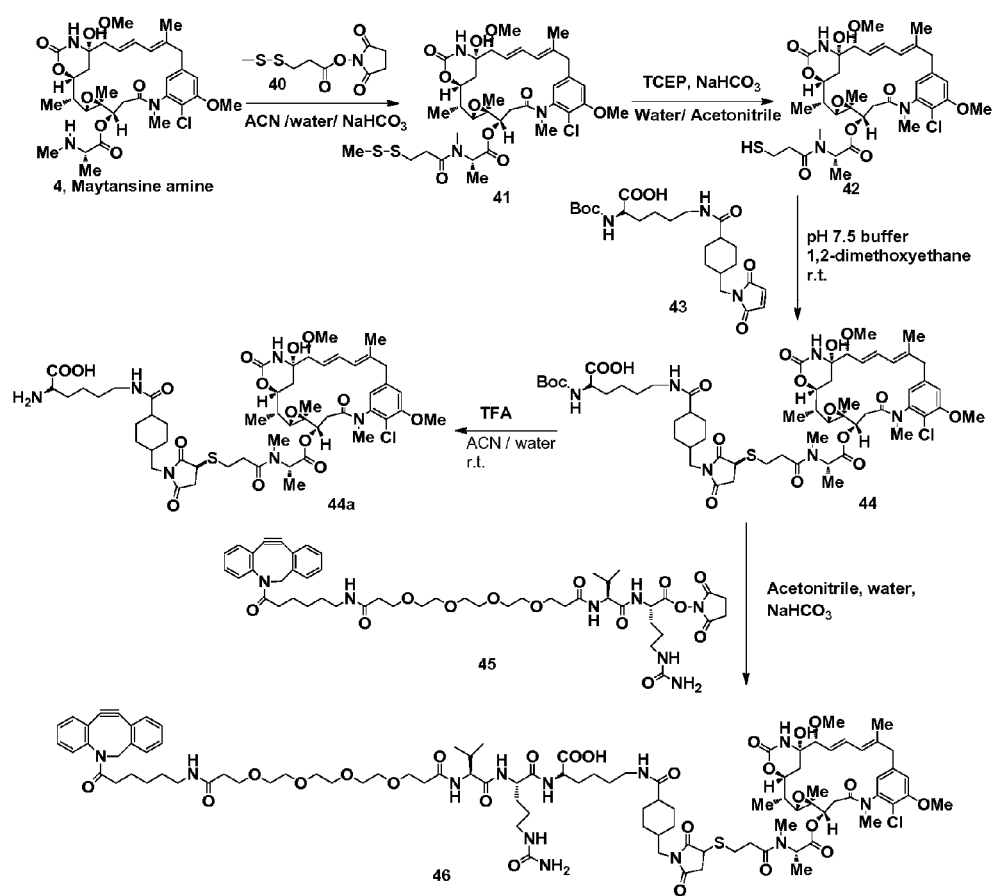
FIG. 12 illustrates an example synthetic scheme for a compound of the present invention.
Figure 13:
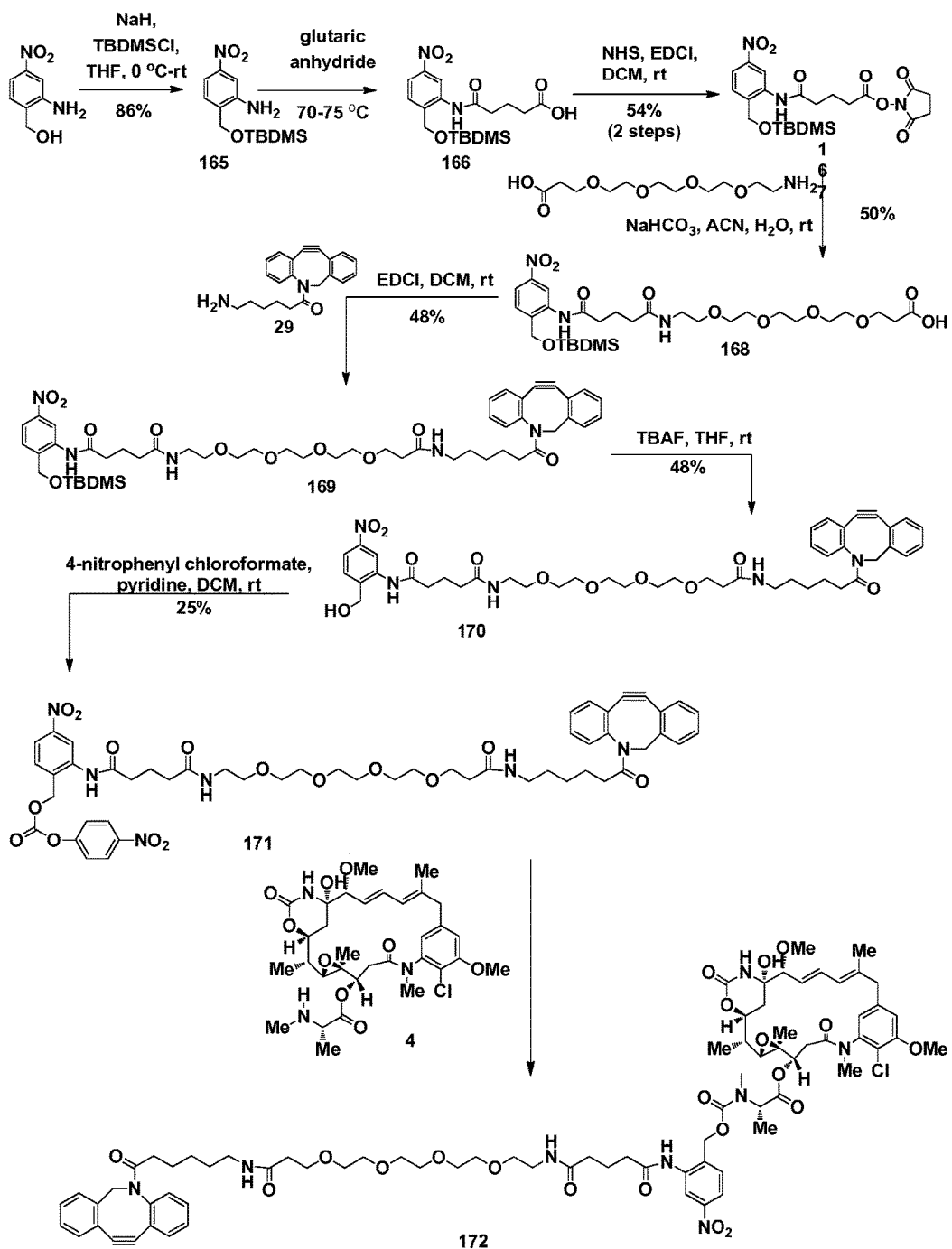
FIG. 13 illustrates an example synthetic scheme for a compound of the present invention.
Figure 14:
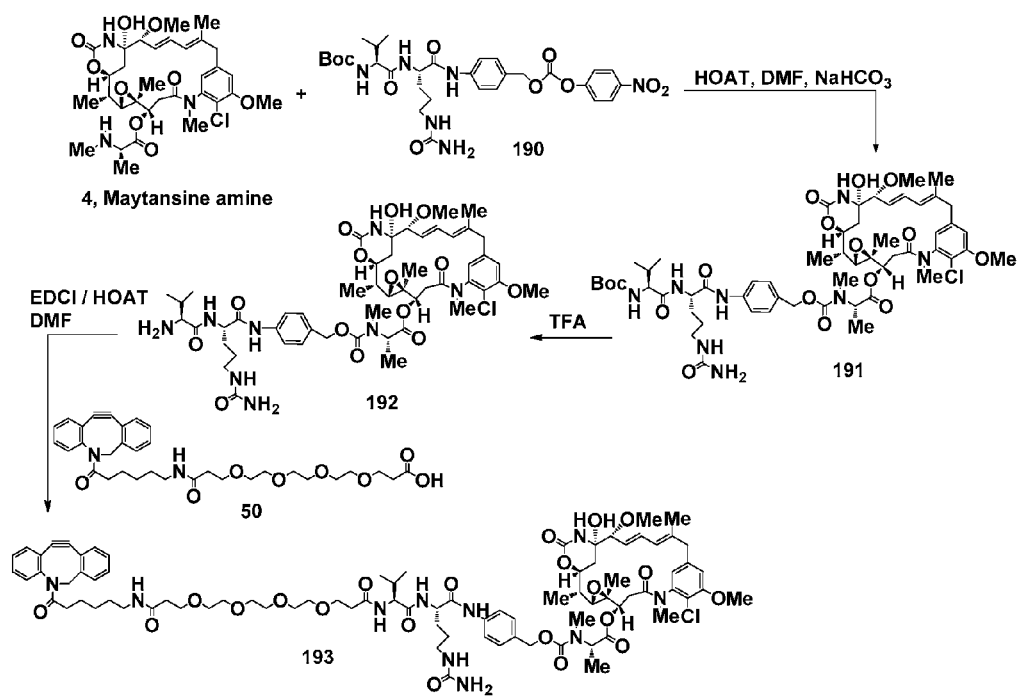
FIG. 14 illustrates an example synthetic scheme for a compound of the present invention.
Figure 15:
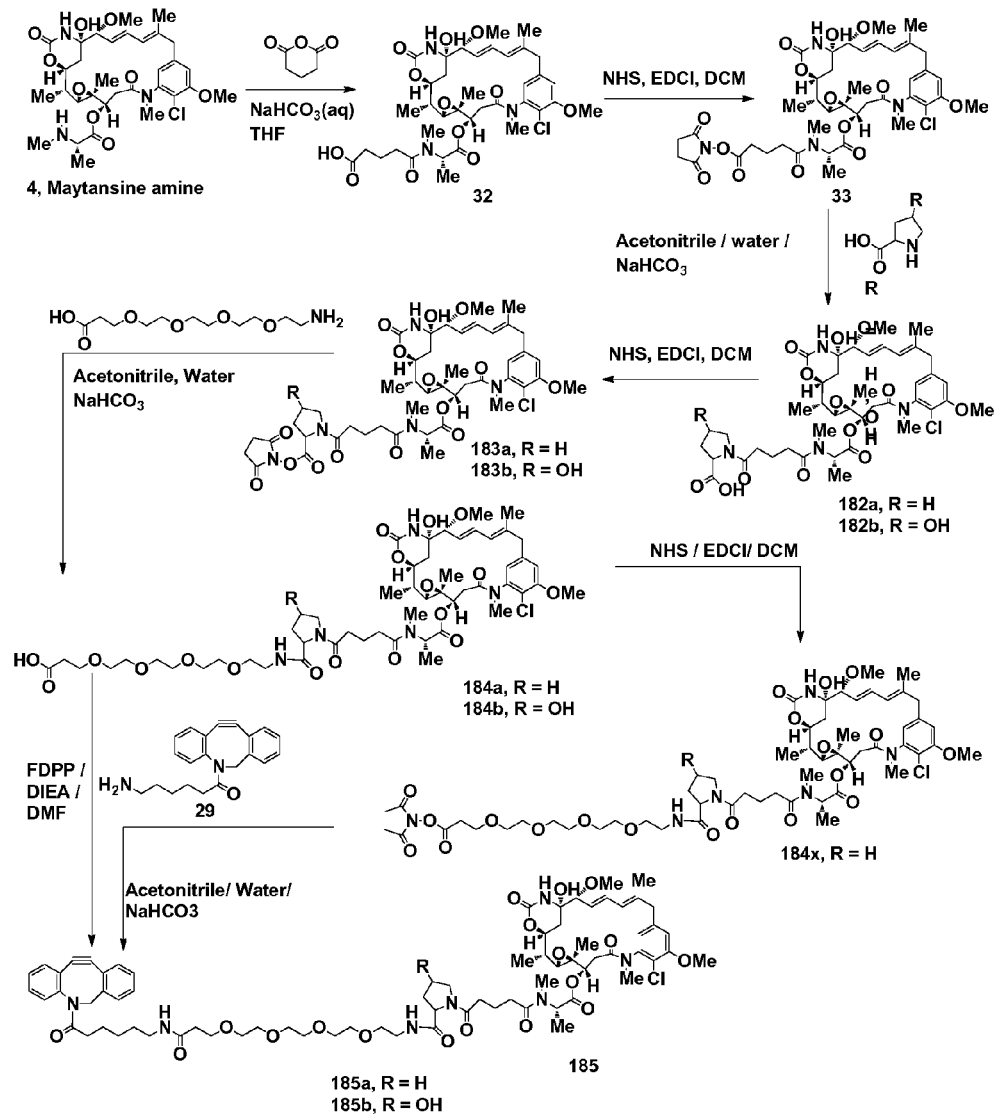
FIG. 15 illustrates an example synthetic scheme for a compound of the present invention.
Figure 16:
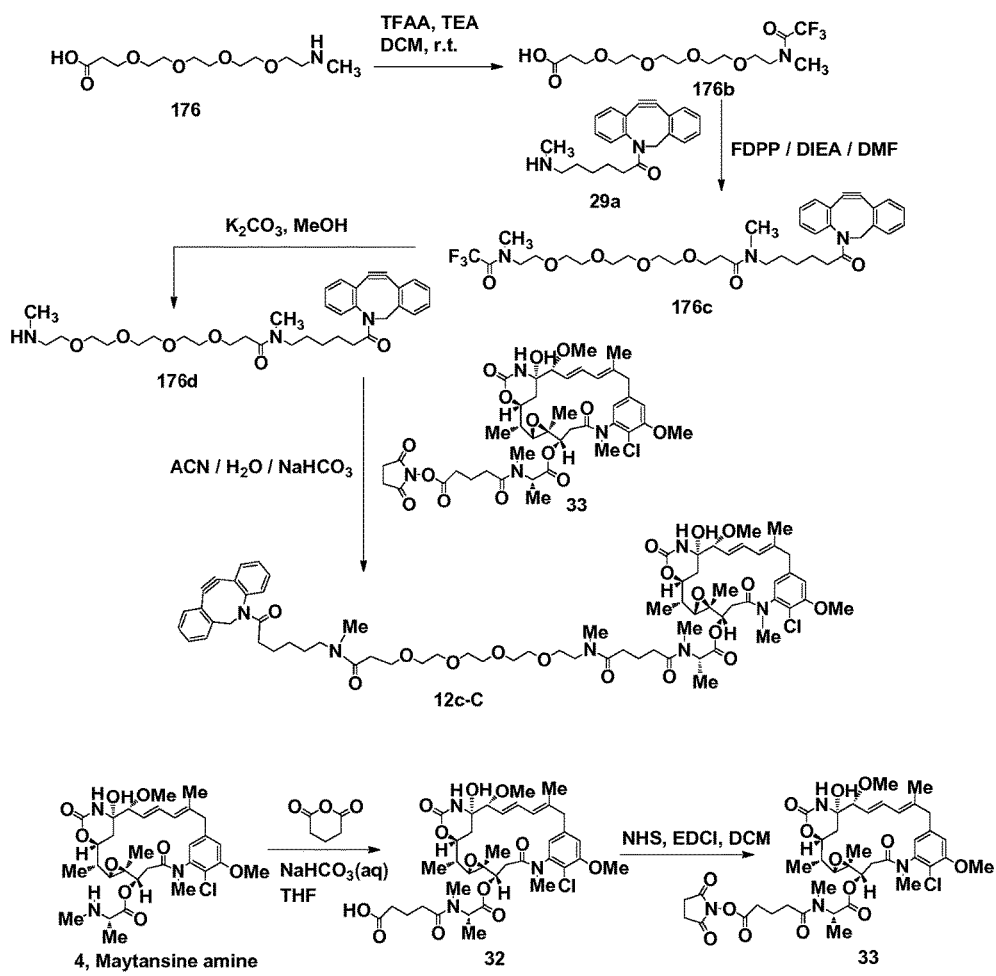
FIG. 16 illustrates an example synthetic scheme for a compound of the present invention.
Figure 17:
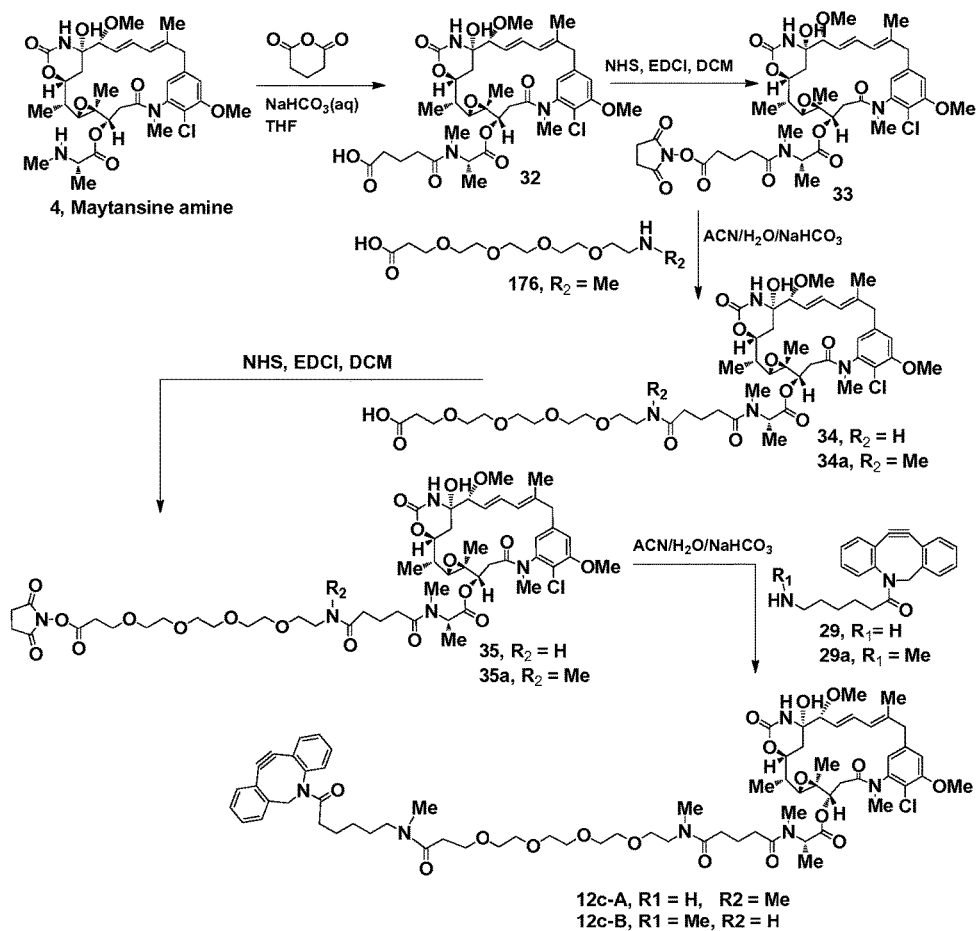
FIG. 17 illustrates an example synthetic scheme for a compound of the present invention.
Figure 18:
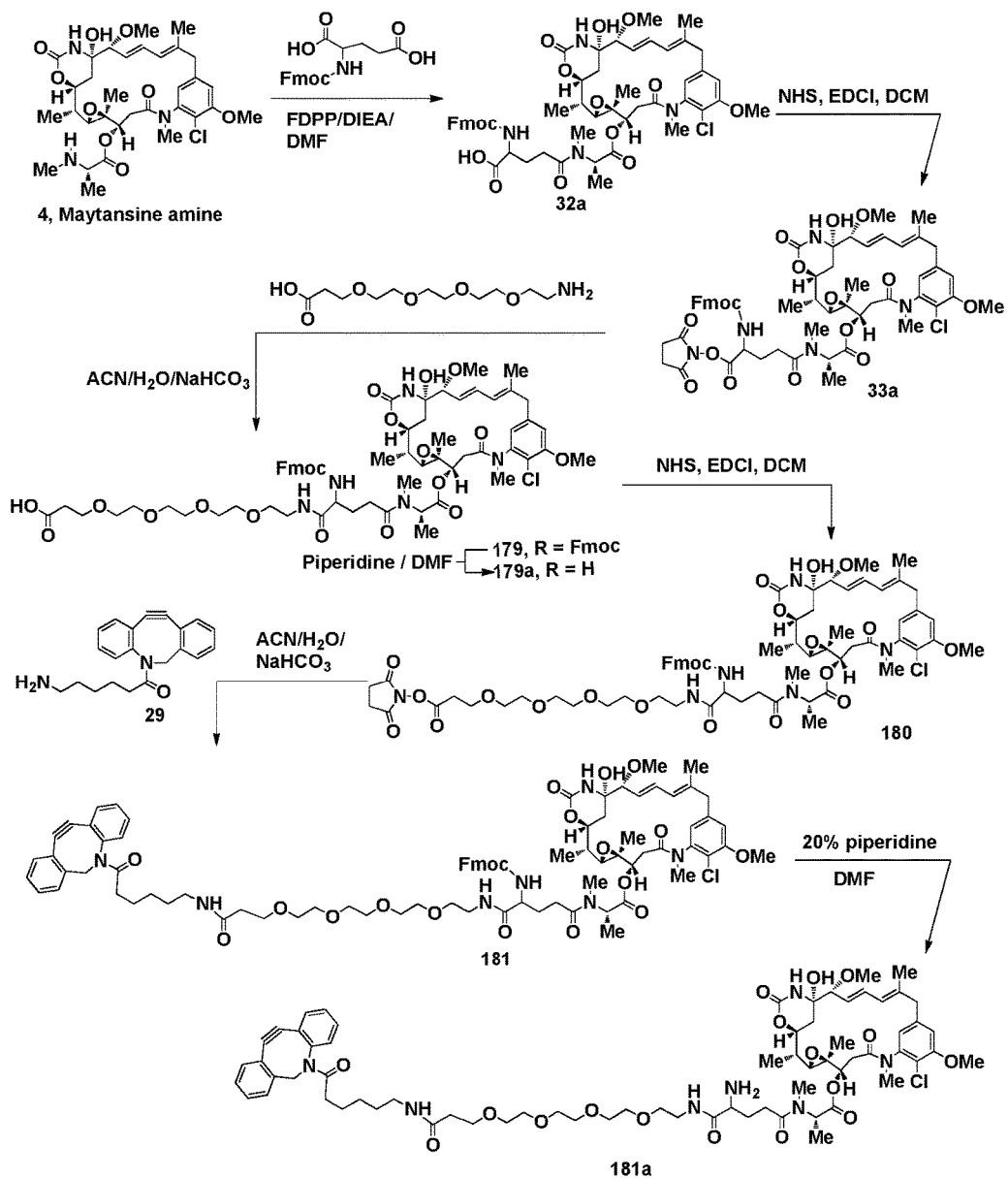
FIG. 18 illustrates an example synthetic scheme for a compound of the present invention.
Figure 19:
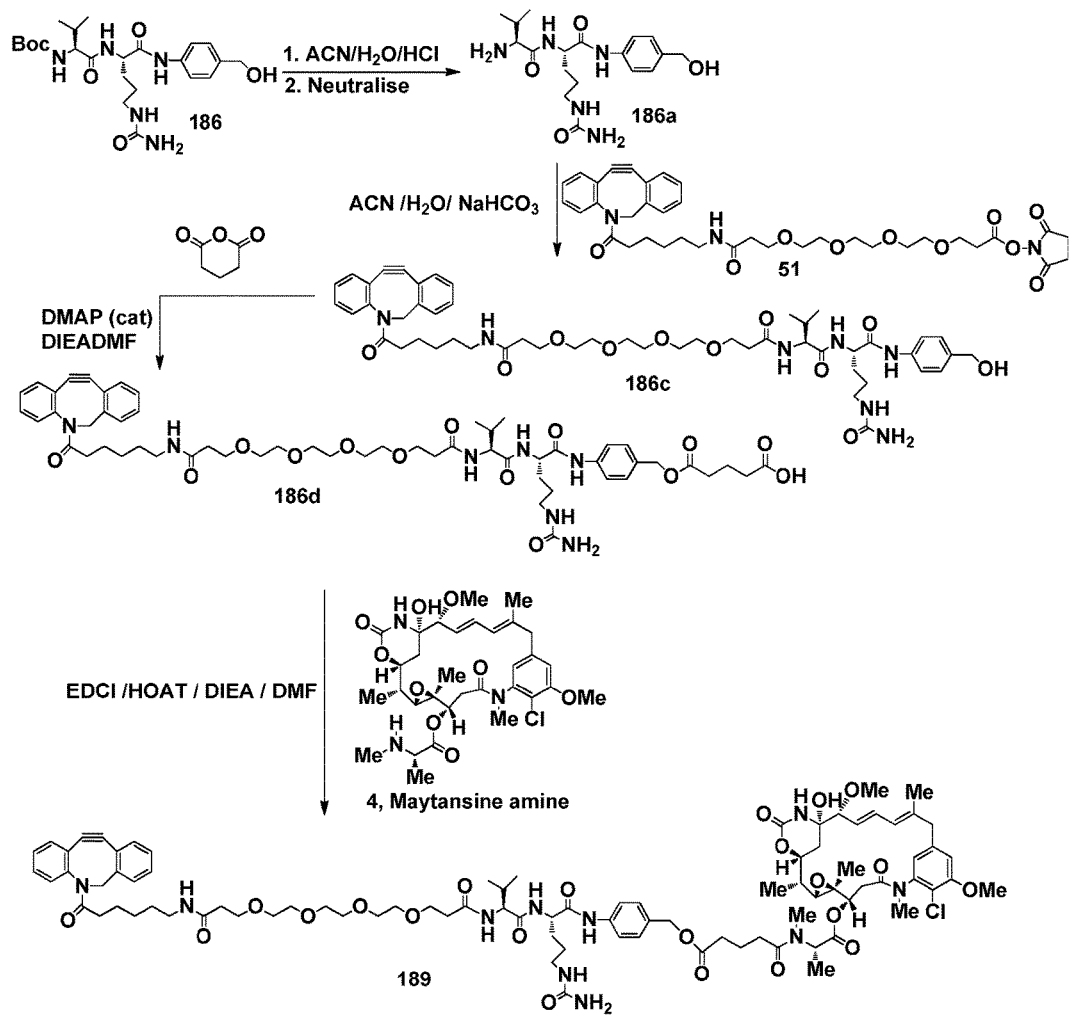
FIG. 19 illustrates an example synthetic scheme for a compound of the present invention.
Figure 20:
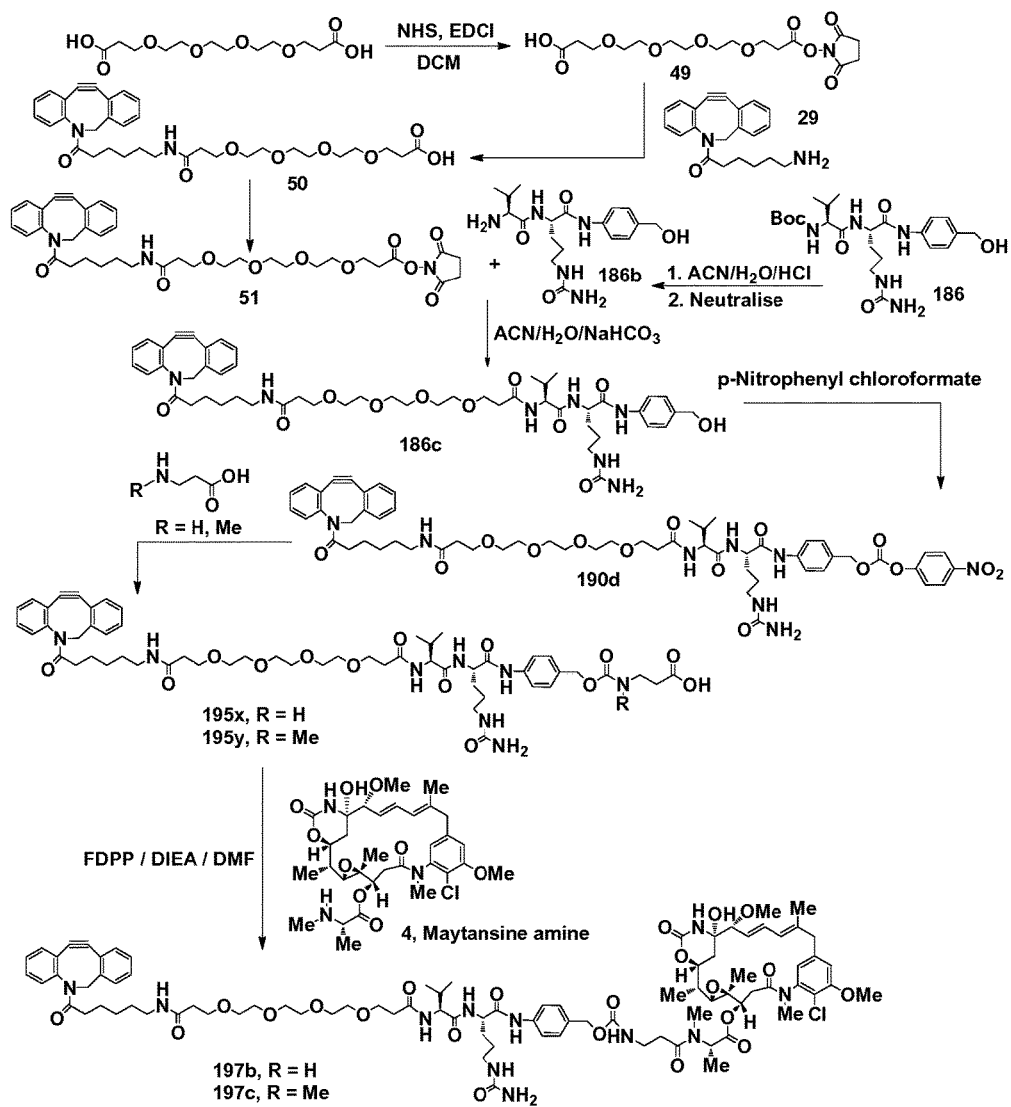
FIG. 20 illustrates an example synthetic scheme for a compound of the present invention.
Figure 21:
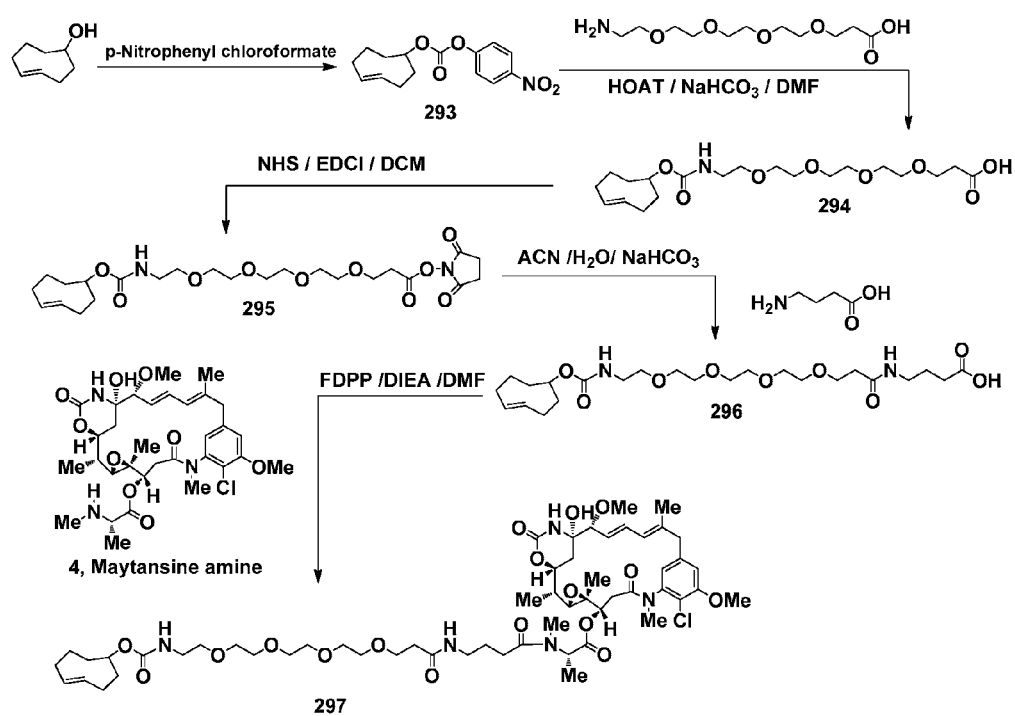
FIG. 21 illustrates an example synthetic scheme for a compound of the present invention.
Figure 22:
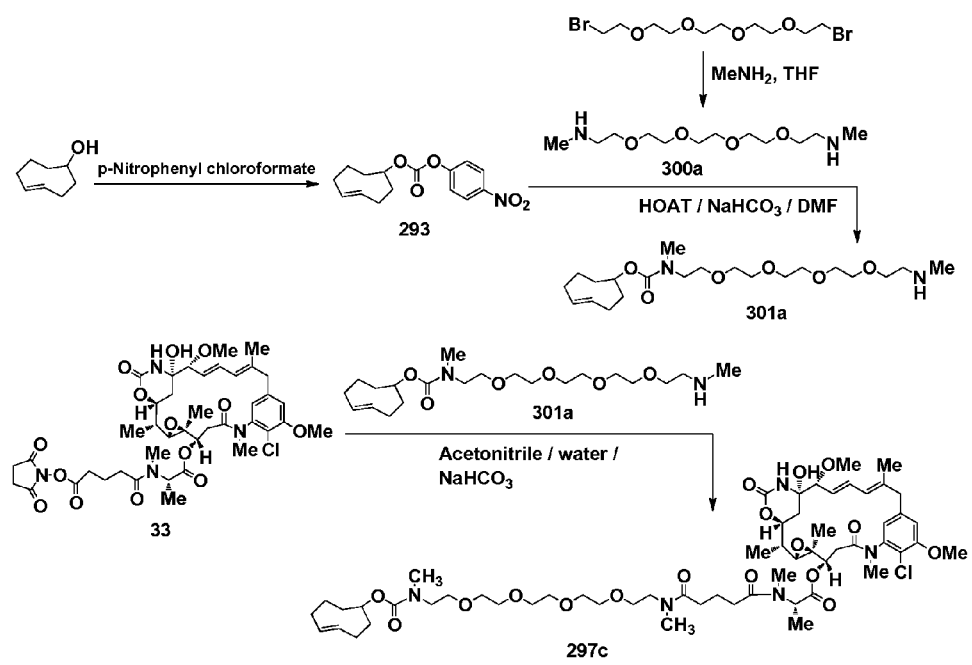
FIG. 22 illustrates an example synthetic scheme for a compound of the present invention.
Figure 23:
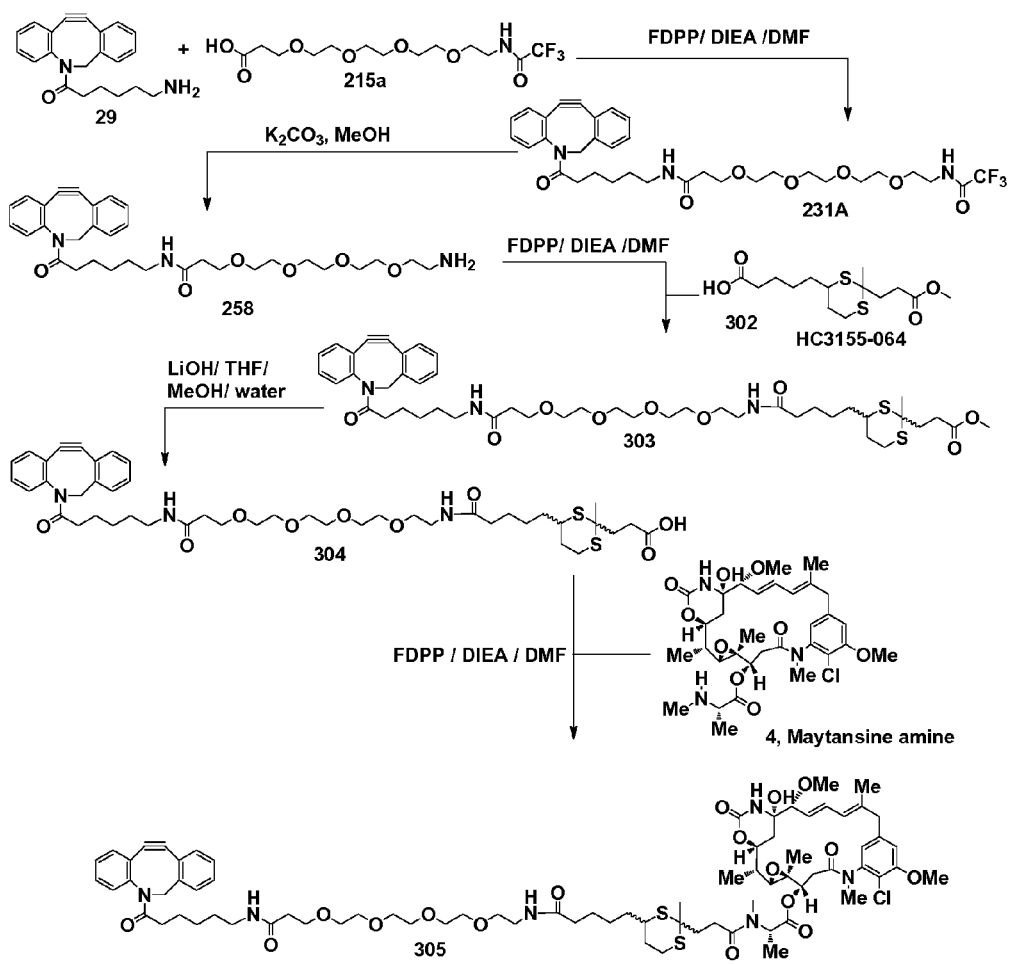
FIG. 23 illustrates an example synthetic scheme for a compound of the present invention.
Figure 24:
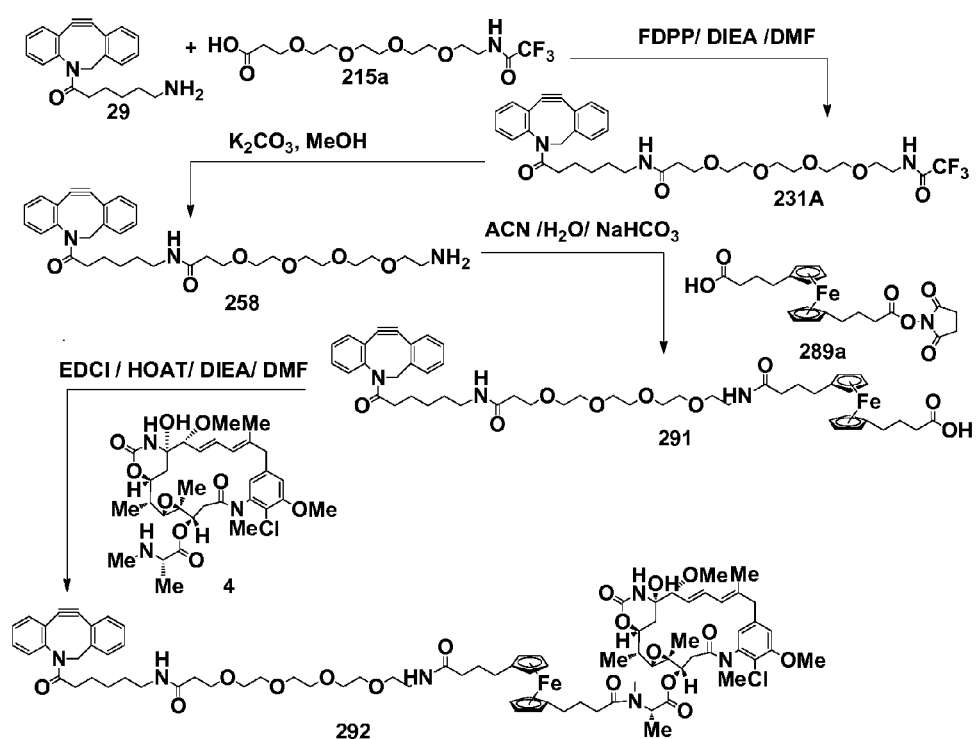
FIG. 24 illustrates an example synthetic scheme for a compound of the present invention.
Figure 25:
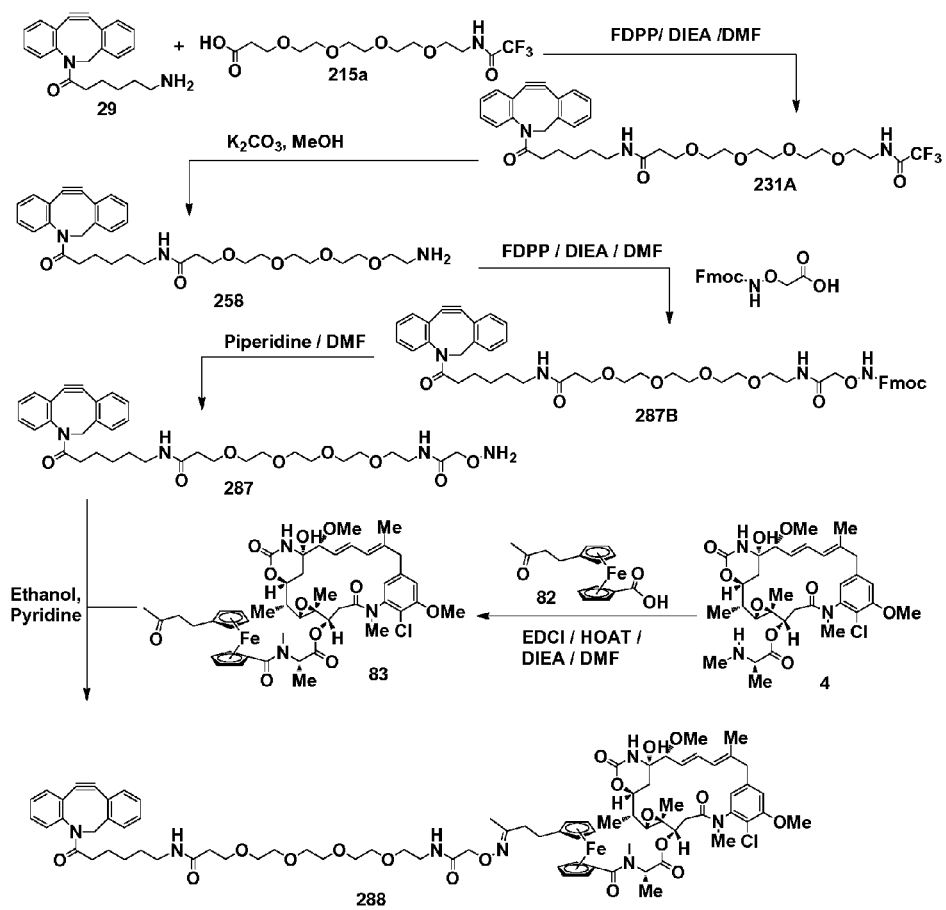
FIG. 25 illustrates an example synthetic scheme for a compound of the present invention.

NNAAs (M) bear a side chain (T) that is any substituent diverse from side clains exhibited by any of the twenty natural amino acids. Because NNAAs typically differ from natural amino acids only in the structure of the side chain, NNAAs form amide bonds with other amino acids, including but not limited to natural amino acids, in the same manner they exist in naturally occurring polypeptides. A side chain of a non-natural amino acid optionally comprises an alkyl-, aryl-, acyl-, keto-, azide-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, tetrazine, or the like, or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety. Various non-natural amino acids and their synthesis are provided in U.S. Pat. No. 7,632,924, US 20140046030, US 20140066598, and US 20140051836, the entire disclosures of which are herein incorporated by reference. FIG. 8 shows example NNAA for employment in the present invention. Spicer, C D, et al., Nature Communications, 5:4740 (2014).

In some embodiments, the non-naturally encoded amino acids include side chain functional groups that react efficiently and selectively with functional groups not found in the 20 common amino acids (including but not limited to, azide, ketone, aldehyde and aminooxy groups) to form stable conjugates. For example, a cell-binding agent that includes a non-naturally encoded amino acid containing an azide functional group can be reacted with a compound containing an alkyne moiety to form a stable conjugate resulting from the selective reaction of the azide and the alkyne functional groups to form a Huisgen [3+2] cycloaddition product.

Exemplary azide-containing or tetrazine-containing non-natural amino acids for incorporating to the cell-binding agent can be represented as follows:

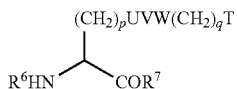

Formula XI wherein p and q are each 0-10; $R^6$ is H, amino acid, polypeptide, or amino terminus modification group; $R^7$ is OH, amino acid, polypeptide, or carboxy terminus modification group; U is a carbonyl, amino-carbonyl-amino, carbamoyl, amino-carbonyloxy, or absent; V is an alkyl, aryl, carbocycle, heterocycle, or absent; W is O, N, S, or absent; and T is an azide group or a tetrazine group.

In some embodiments, V is an aryl and W is absent. In some embodiments, $R^6$ is H and $R^7$ is OH. In some embodiments, U is a carbonyl, amino-carbonyl-amino, carbamoyl, or amino-carbonyloxy; V is a heterocycle or absent; W is absent; and T is an azide group. The present invention expressly contemplate all isomers, including but not limited to tautomers and stereoisomers (R and S), as an individual isomer or as a mixture, and all salt forms of a non-natural amino acid.

Exemplary azide-containing non-natural amino acids include, but are not limited to, the following:

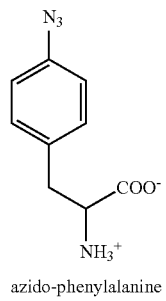

azido-phenylalanine

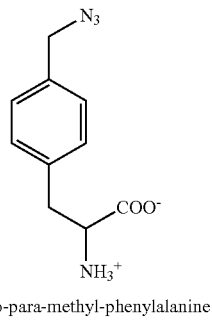

azido-para-methyl-phenylalanine

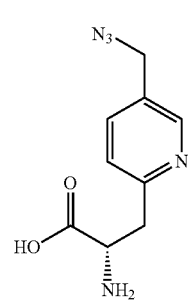

M1

M2

M3

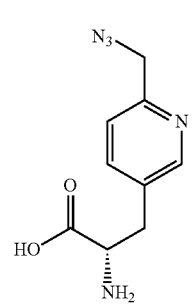

M4

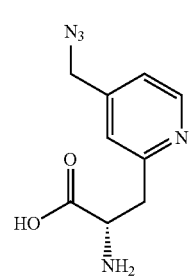

M5

M6
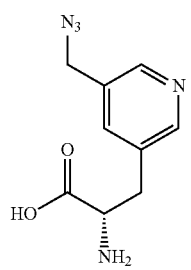
M7
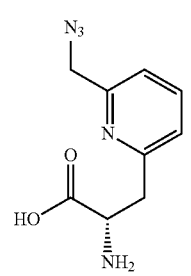
M8
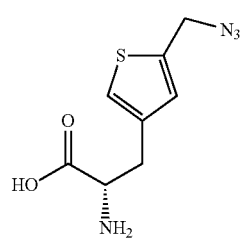
M9
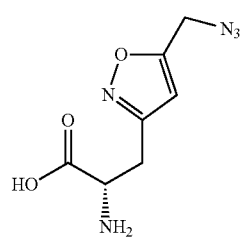
M10
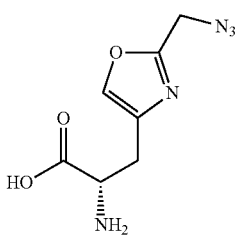
M11
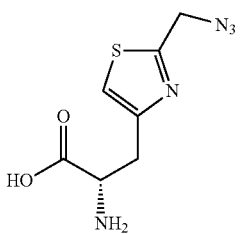
M12
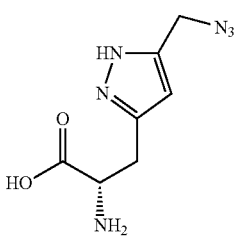
M13
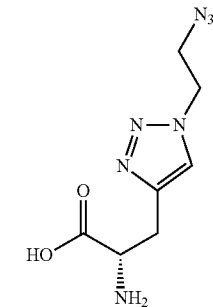
M14
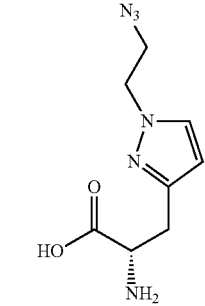
M15
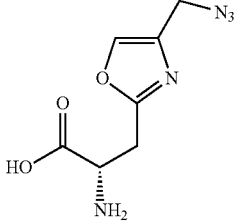
M16
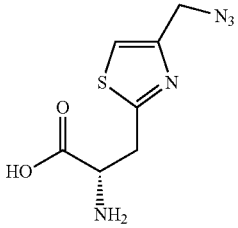
M17
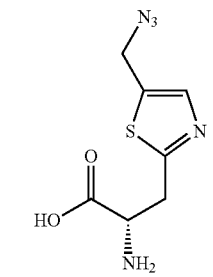

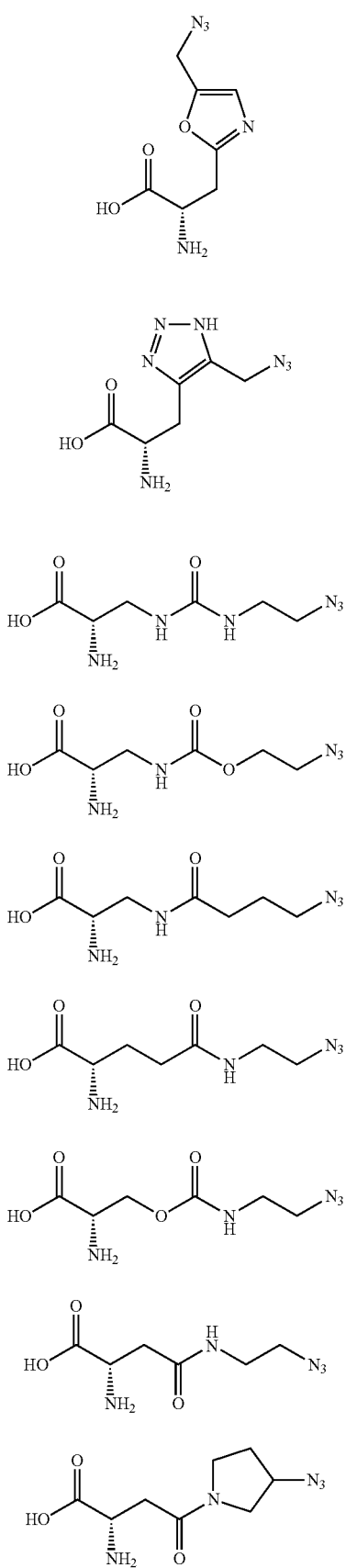
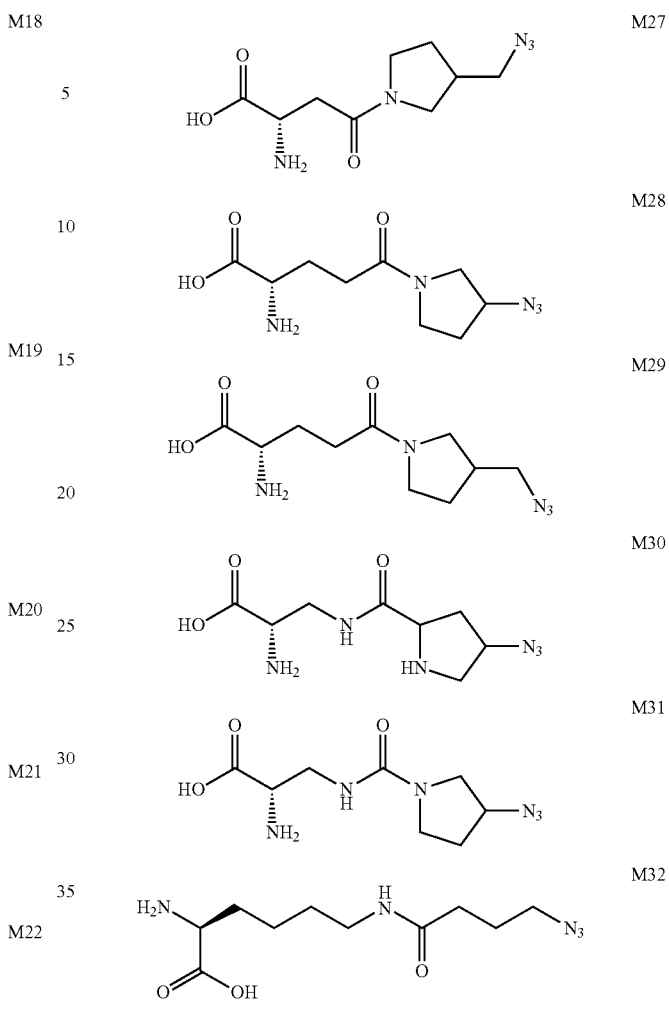

The terms "azido" and "azide" are used interchangeably in the present invention and both refer to an —N₃ group. Many azide-containing amino acids are available from commercial sources. For example, 4-azidophenylalanine can be obtained from Chem-Impex International, Inc. (Wood Dale, Ill.). (S)-5-Azido-2-(Fmoc-amino)pentanoic acid, (S)-(−)-2-azido-6-(Boc-amino)hexanoic acid (dicyclohexylammonium) salt, (S)-2-azido-3-(4-tert-butoxyphenyl)propionic acid cyclohexylammonium salt, (S)-2 azido-3-(3-indolyl) propionic acid cyclohexylammonium salt, (S)-2-azido-3-methylbutyric acid cyclohexylammonium salt, (S)-2-azido-4-(methylthio)butanoic acid cyclohexylammonium salt, (S)-2-azido-3-phenylpropionic acid (dicyclohexylammonium) salt, and (S)-2-azido-propionic acid cyclohexylammonium salt are commercially available from Sigma-Aldrich. For those azide-containing amino acids that are not commercially available, the azide group can be prepared relatively readily using standard methods known to those of skill in the art, including, for example, displacement of a suitable leaving group (including but not limited to, halide, mesylate, tosylate) or via opening of a suitably protected lactone. See, e.g., Advanced Organic Chemistry by March (Third Edition, 1985, Wiley and Sons, New York).

Exemplary tetrazine-containing non-natural amino acids include, but are not limited to, the following:

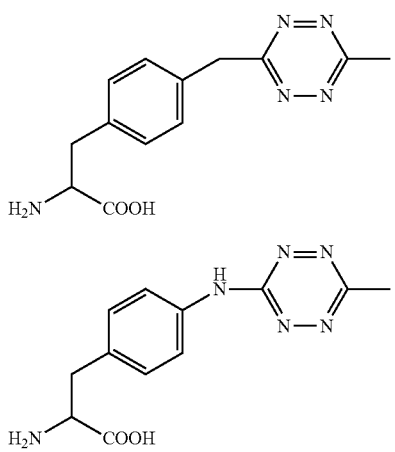

M33

M34

Tetrazine-containing NNAAs can be readily incorporated integral to peptides and polypeptides of cell-binding agents using procedures known in the literature.

Azide-substituted and tetrazine-substituted non-natural amino acids can be incorporated site-selectively into proteins using methods described. Hallam, T., et al. (SUTRO), Future Med Chem. 2014 July; 6(11):1309-24 and Bioconjug Chem. 2014 Feb. 19; 25(2):351-61; L. Wang, et al., (2001), Science 292:498-500; J. W. Chin, et al., Science 301:964-7 (2003)); J. W. Chin et al., (2002), Journal of the American Chemical Society 124:9026-9027; J. W. Chin, & P. G. Schultz, (2002), Chem Bio Chem 11:1135-1137; J. W. Chin, et al., (2002), PNAS 99:11020-11024, L. Wang, & P. G. Schultz, (2002), Chem. Comm., 1-10.

Biomolecule Synthesis and NNAAs

Antibodies comprising site specific NNAAs may be produced, for example, in an in vitro prokaryotic cell-free system. In vitro site-specific insertion of azido-phenylalanine or azido-para-methyl-phenylalanine, for example, into a growing synthetic peptide by means of an orthogonal tRNA synthetase/tRNA pair is accomplished wherein the charged tRNA recognizes a nonsense codon.

Scalable cell-free protein synthesis systems are known in the art for the site specific insertion of NNAAs and for the full production of antibodies including disulfide bonds. Swartz, J R., et al., *Simplifying and Streamlining Escherichia Coli-Based Cell-Free Protein Synthesis*. Biotechnol Prog. 28(2):413 (2012) PMID: 22275217; Swartz, J R., et al., *Cell-free Production of Antibody Fragment Bioconjugates for Ex Vivo Detection of Tumor Cells*. Biochem Biophys Res Commun. 390(3):971(2009) PMID: 19852937; Swartz, J R., et al., *An Integrated Cell-Free Metabolic Platform for Protein Production and Synthetic Biology*. Mol Syst Biol. 4:220 (2008). See, e.g., Swartz, et al., methods of in vitro protein synthesis U.S. Pat. No. 7,338,789 and related cases. U.S. Pat. No. 8,715,958. See, also U.S. Pat. Nos. 7,332,571, 7,385,028, 7,696,312, 7,928,163, and 8,008,428. Schultz, P G, et al., *Development of Improved tRNAs for In Vitro Biosynthesis of Proteins Containing Unnatural Amino Acids*. Chem Biol. 3(12):1033 (1996); Schultz, P G, et al., *A General Method for Site-Specific Incorporation of Unnatural Amino Acids into Proteins*. Science 244(4901):182 (1989); Dieter Söll, et al., *When Protein Engineering Confronts the tRNA World*. PNAS US 94(19):10007 (1997). Voloshin, et al., 8778631 *Method for Introducing Non-Native Amino Acids into Preselected Positions of a Polypeptide Using a Cell-Free Synthesis System*. Site specific in vivo incorporation of unnatural amino acids: See, e.g., U.S. Pat. Nos. 7,045,337; 8,173,392; 8,114,648; 8,030,074; 7,915,025; 7,638,300; 7,368,275; 8,173,364; 8,183,012; 7,713,721; 7,354,761; 7,083,970; 8,012,739; 7,083,970; 7,432,092; 8,114,629; 8,071,344; 7,910,345; 7,524,647; 7,608,423.

Active Release Products

Biomolecule conjugates of the present invention are intended for the administration to mammals, for example, for the treatment of disease conditions. The biomolecule conjugates comprise a biomolecule wherein at least one non-natural amino acid (NNAA) is integral to the structure of the biomolecule and wherein the NNAA is a point of attachment of a linker to which a payload, particularly a cytotoxic agent, is attached. Biomolecule conjugates of the present invention generally release active compounds comprising a payload cytotoxic agent following administration.

Accordingly another aspect of the current invention is a release product corresponding to each Formula I compound described herein comprising the payload. A further aspect of the invention is a release product corresponding to each of the Formula I compounds described herein comprising the linker and the payload.

One embodiment of an active release compound (corresponding to the employment of NNAA azido-para-methyl-phenylalanine (M2) and Formula I (compound I4) of the present invention generally comprises the non-naturally occurring amino acid, the linker, and the payload as follows:

AR4
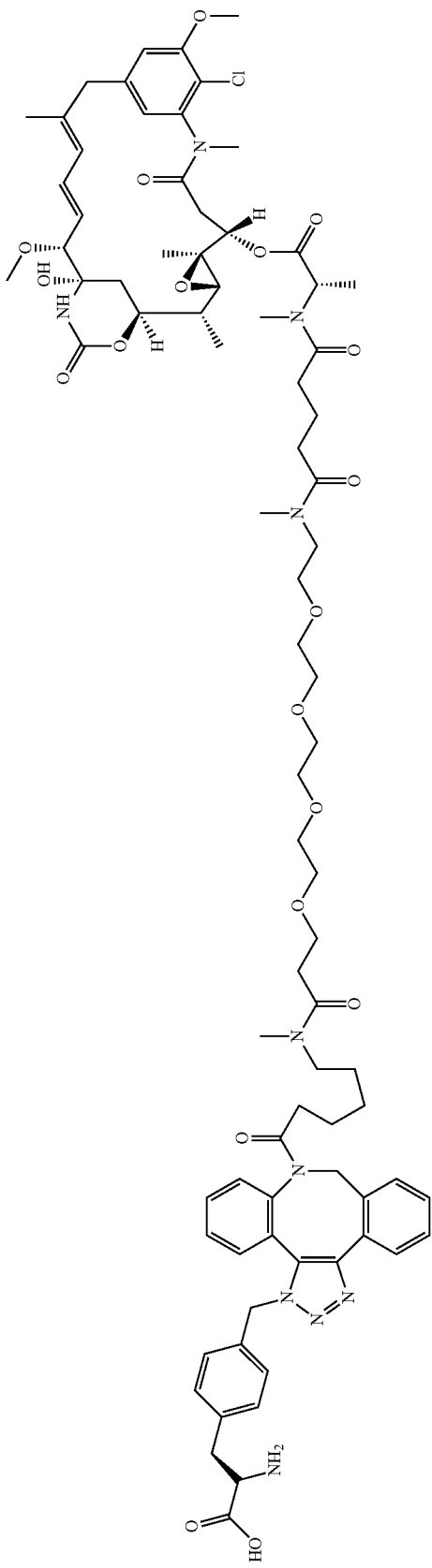

This active release product, for example, exists in regioisomeric form. Since I4 exists as two regio-isomers, the catabolite also exists as two regio-isomers. As is now appreciated by those of skill in the art, in view of this disclosure, analogous active release products fundamentally comprising the non-natural amino acid, the linker and payload, are generated upon/after administration of biomolecule conjugates described herein. Accordingly, another aspect of the present invention—an example of which is AR4—is a release product, corresponding to each of the Formula I compounds described herein, comprising a non-natural amino acid described herein, the linker and the payload.

Production of Biomolecule Conjugates

Formula III Conjugates by Means of 1,3-Dipolar Cycloaddition Reactions

Cycloaddition reaction between compounds of Formula I containing a strained alkyne and compounds of Formula II containing at least one azide-substituted non-natural amino acid is a selective and biocompatible approach (azide+triple bond [3+2] cycloadditon (or "click" reaction)) to the production of Formula III conjugates.

The Formula I dotted line (A) represents a strained alkyne. The Formula II (T) is an azide group on the NNAA (M). Other groups and substituents are defined supra.

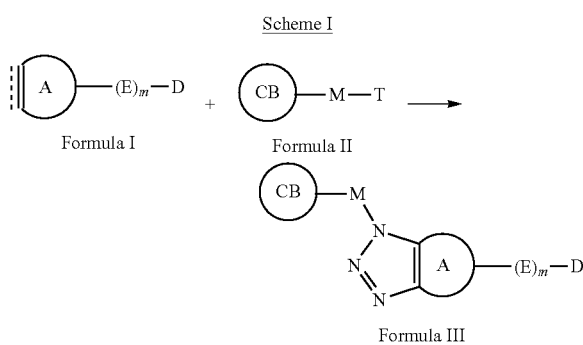

Scheme I

Figure 6A:
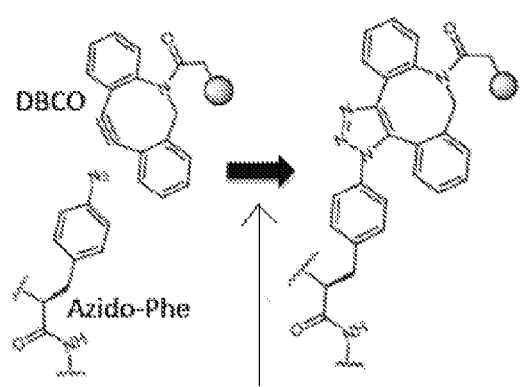
FIG. 6A illustrates a 1,3-dipolar cycloaddition reaction

Azide and strained alkyne functional groups are largely inert towards biological molecules in an aqueous environment allows the use of the azide-alkyne cycloaddition reactions described herein for the coupling of cytotoxic agents (D), for example, to cell-binding agents (CB) as illustrated in Scheme I. See, e.g., FIG. 6A.

The resulting triazoles have similarities to the ubiquitous amide moiety found in nature, but unlike amides, are not susceptible to hydrolytic or enzymatically catalyzed cleavage. Additionally, triazoles are nearly impossible to oxidize or reduce under physiological conditions. The cycloaddition reactions employed in assembling conjugates of the present invention, also known as "click" chemistry, is the reaction between a 1,3-dipol, e.g. an azide, and a dipolarophile, e.g., a substituted alkyne, to form a five-membered ring. The increased reactivity resulting from the strained alkyne allows the cycloaddition reaction between compounds of Formula I and compounds of Formula II to proceed smoothly at room temperature without the use of copper or other catalysts. Procedures for the copper-free cycloaddition reaction are well known in the field of chemistry. See, e.g. Lutz, Angew Chem Int Ed Engl. 2008, 47(12), 2182-4; Bertozzi et al., Angew. Chem. Int. Ed. 2009, 48, 6974; Bertozzi et al., J. Am. Chem. Soc. 2010, 132, 3688; Jewett, et al., Chem Soc Rev. 2010, 39(4), 1272-9, Schultz et al., Org. Lett. 2010, 12 (10), 2398-401, the entirety of which are herein incorporated by reference. Reaction conditions for general copper-free cycloaddition on simple substrates are well known in the art (e.g. room temperature in acetonitrile). See, e.g., FIG. 6A.

Methods of producing biomolecules which comprises at least one azide-substituted NNAA preferably a plurality of each, e.g., 2-50, 2-25, 2-15, 2-10, or 2-5 of each is within the scope of the invention described herein. As a corollary methods of producing biomolecules, e.g., antibody species, having at least one azide+triple bond [3+2] cycloadditon conjugated payload species is within the scope of the invention described herein. Biomolecules, e.g., antibody species, having a plurality, e.g., 2-100, 2-50, 2-25, 2-10, or 2-5, of azide+triple bond (3+2) cycloadditon conjugated payload species is within the scope of the invention described herein.

Formula III' Conjugates by Means of 4+2 Cycloaddition Reactions

Figure 6B:
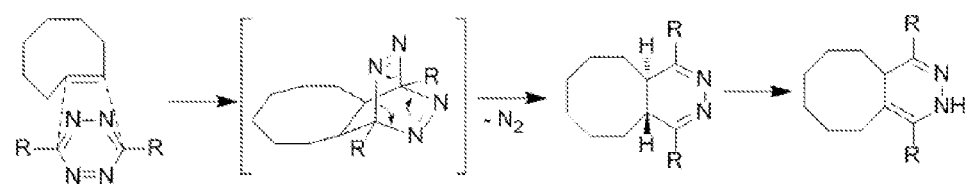
FIG. 6B illustrates a strained alkene and a tetrazine 4+2 cycloaddtion reaction.
Figure 7:
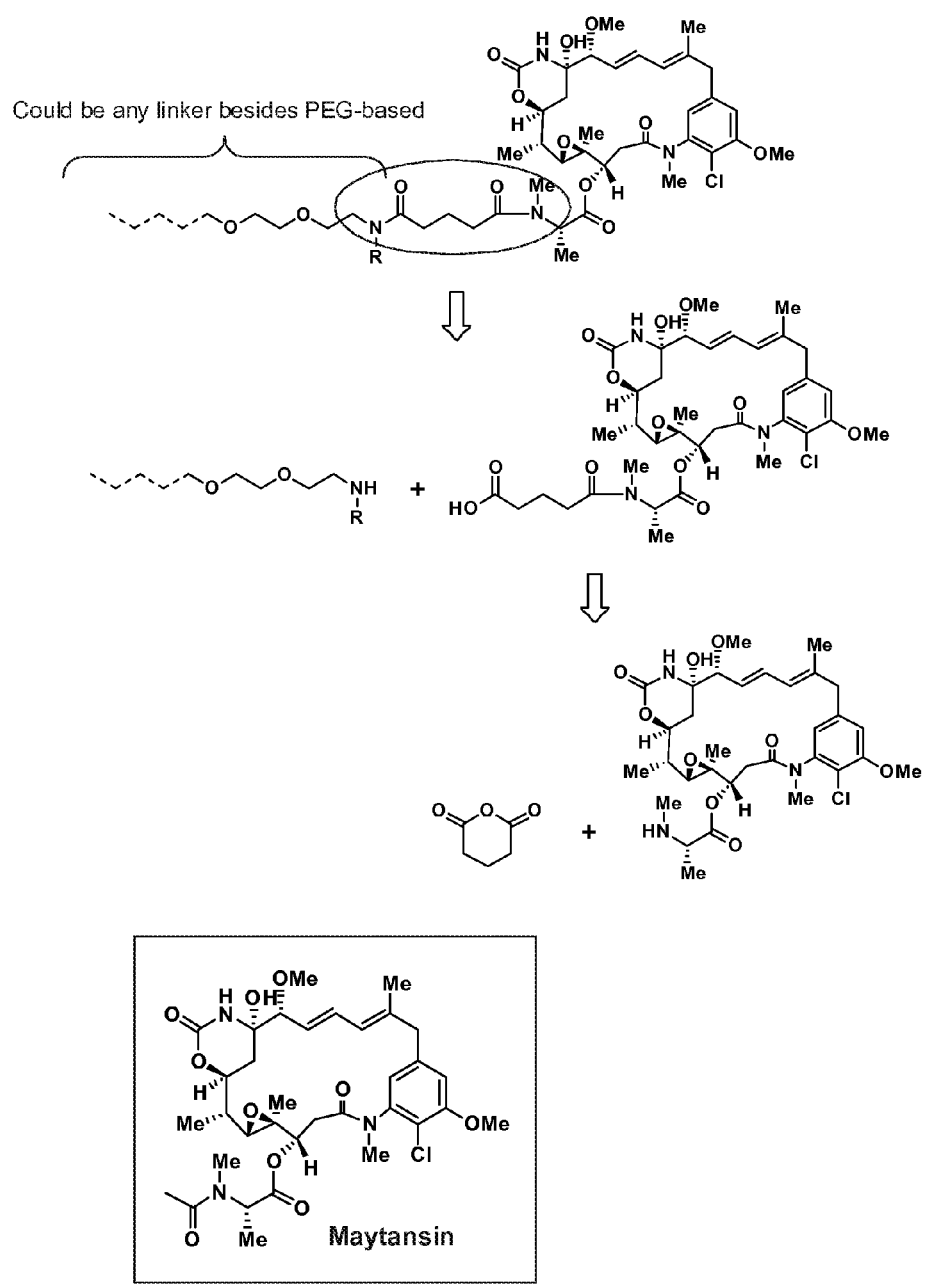
FIG. 7 schematic illustrates amide bonds used to attach cytotoxic agents.

As an alternative chemistry to the azide+triple bond [3+2] cycloadditon (or "click" reaction), the reaction of a strained trans-double bond (strained alkene) with a tetrazine moiety results in a [4+2] cycloaddition with subsequent expulsion of $N_2$ to generate a cyclic diazene. See, e.g., FIG. 6B.

Similar to the reaction between an alkyne and a azide, a strained alkene and a tetrazine undergoes a [4+2] cycloadtion under mild conditions to provide conjugates of Formula III' as shown in Scheme II. Formula I (A) dotted line is absent, i.e., strained alkene (rather than strained alkyne), and Formula II (T) is a tetrazine group on the NNAA (M).

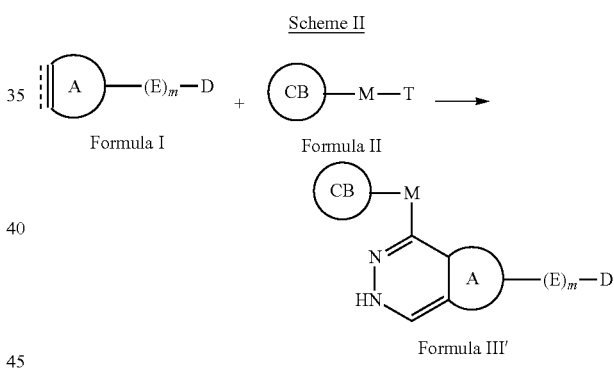

Scheme II

Reaction conditions and procedures to effect the combination of strained alkenes and tetrazine moieties as discussed and illustrated herein are well known in the art. Reactions of strained alkenes and tetrazine moieties in this manner are described, for example, by Wang, et al., Nature Chem. (2014) 6, 393-403; Kim, et al., Curr. Opin. Chem. Biol. (2013) 17(3), 412-9; Sečkutė, et al., Curr Opin Chem Biol. (2013) 17(5), 761-7; Lang, et al., Nature Chem. (2012) 4, 298-304; Seitchik, et al., J. Am. Chem. Soc. (2012) 134(6), 2898-2901; Taylor, et al., J. Am. Chem. Soc. (2011) 133, 9646; Devaraj, et al., Bioconjugate Chem. (2008) 19, 2297; Devaraj, et al., Acc. Chem. Res. (2011) 44, 816; Taylor, et al., J. Am. Chem. Soc. (2011) 133, 9646; Blackman, et al., J. Am. Chem. Soc. (2008) 130, 13518, all of which are herein incorporated by reference.

Methods of producing biomolecules which comprises at least one tetrazine-substituted NNAA preferably a plurality of each, e.g., 2-50, 2-25, 2-15, 2-10, or 2-5 of each is within the scope of the invention described herein. As a corollary methods of producing biomolecules, e.g., antibody species, having at least one strained alkene tetrazine moiety [4+2]

cycloaddition conjugated payload species is within the scope of the invention described herein. Biomolecules, e.g., antibody species, having a plurality, e.g., 2-100, 2-50, 2-25, 2-10, or 2-5, of strained alkene tetrazine moiety [4+2] cycloaddition conjugated payload species is within the scope of the invention described herein.

Separate Payload (D) Species can be Conjugated to the Same Biomolecule by First Generating a Biomolecule, e.g., Antibody Species, with Two Non-Natural Amino Acids, One for [4+2] Incorporation of Linker/Payload, and the Other Amino Acid for [3+2] Incorporation of a Different Linker and/or Payload.

Accordingly, separate Payload (D) species can be conjugated to the same biomolecule as otherwise described herein (CB) by means of incorporating different NNAAs (M) into the same biomolecule (CB) (Formula II), e.g., (1) azide-substituted NNAA (M-T) and (2) tetrazine substituted NNAA (M-T). According to the methods described herein, i.e., Formula III conjugates by means of 1,3-dipolar cycloaddition reactions and Formula III' conjugates by means of [4+2] cycloaddition reactions can be performed on the same biomolecule (CB). Single biomolecules, e.g., a single antibody species, which comprises at least one azide-substituted NNAA and at least one tetrazine substituted NNAA, each of which NNAA are described herein, is within the scope of the invention. As a corollary, single biomolecules, e.g., a single antibody species, having two distinct conjugated payload species (D) and/or linkers ((E)$_m$) is within the scope of the invention described herein. Methods of producing such biomolecules which comprises at least one azide-substituted NNAA and at least one tetrazine substituted NNAA, preferably a plurality of each, e.g., 2-50, 2-25, 2-15, 2-10, or 2-5 of each is, according to this disclosure, within the scope of the invention. Methods of producing single biomolecules having two distinct conjugated payload species (D) and/or linkers ((E)$_m$) is further within the scope of the invention described herein.

Branched Linkers

Attaching 2 or so linkers per antibody as otherwise described herein, each linker has a branch point such that two payloads, for example, can be attached.

small molecule agent. Monomethylvaline compounds. See, e.g., U.S. Pat. Nos. 7,994,135; 7,964,567; 7,964,566; 7,745,394; 7,498,298.

Maytansinoids, for example, inhibit microtubule formation and are highly toxic to mammalian cells. In a preferred embodiment of the invention, the payload is a cytotoxic agent which is a maytansinoid, including maytansinol, maytansinol analogs, ansamitocin and ansamitocin analogs.

Maytansinoids

Maytansinoids are highly cytotoxic drugs. Maytansine was first isolated by Kupchan, et al. from the east African shrub *Maytenus serrata* and shown to be 100- to 1000-fold more cytotoxic than conventional cancer chemotherapeutic agents like methotrexate, daunorubicin, and vincristine (U.S. Pat. No. 3,896,111). Subsequently, it was discovered that certain microbes also produce maytansinoids, such as maytansinol and C-3 esters of maytansinol (U.S. Pat. No. 4,151,042). Synthetic C-3 esters of maytansinol and analogues of maytansinol have also been reported (Kupchan, et al., 21 J. Med. Chem. 31-37 (1978); Higashide, et al., 270 Nature 721-722 (1977); Kawai, et al., 32 Chem. Pharm. Bull. 3441-3451 (1984)). Examples of analogues of maytansinol from which C-3 esters have been prepared include maytansinol with modifications on the aromatic ring (e.g. des-chloro) or at the C-9, C-14 (e.g. hydroxylated methyl group), C-15, C-18, C-20 and C-4,5. A number of immunoconjugates incorporating maytansinoids have been reported, including U.S. Pat. Nos. 8,685,920, 8,624,003, 8,613,930, 8,603,483, 8,563,509, 8,337,856, 8,236,319, 6,333,410, 6,441,163, and US 20140023665, the entire disclosures of which are herein incorporated by reference.

Maytansinoids suitable for use in the present invention are well known in the art. Examples of suitable maytansinol analogs include those having modified aromatic rings and/or modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, 6,333,410, and US 20140023665, the entire disclosures of which are herein incorporated by reference.

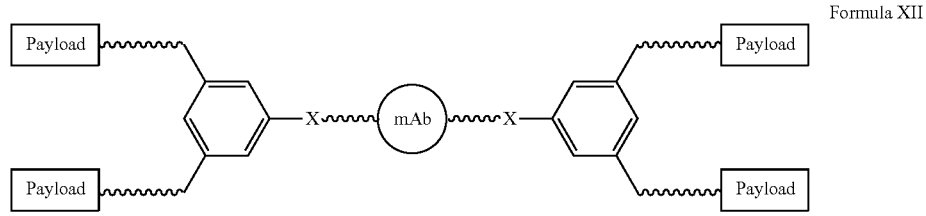

Formula XII

Many permutations of this type of approach exists as can be appreciated by those of ordinary skill.

Payload, Cytotoxic Agents, and Maytansinoids

"Cytotoxic agent" as used herein refers to any compound that results in the static growth, decreased viability or induction of death for certain cell types. Suitable payload cytotoxic agents include, for example, maytansinoids and maytansinoid analogs, taxoids, CC-1065 and analogs, dolastatin and analogs, zelesin and analogs, pyrrolobenzodiazepine dimers and analogs; natural product cytotoxins and synthetic analogs including crytophycins, amatoxins, tubulysins, as well as any other potent natural or non-natural Examples of suitable maytansinol analogs having a modified aromatic ring include: (1) C-19-des-chloro (U.S. Pat. No. 4,256,746) (prepared by LAH reduction of ansamytocin P2); (2) C-20-hydroxy (or C-20-demethyl)+/−C-19-des-chloro (U.S. Pat. Nos. 4,361,650 and 4,307,016) (prepared by demethylation using *Streptomyces* or *Actinomyces* or dechlorination using LAH); and, (3) C-20-demethoxy, C-20-acyloxy (—OCOR), +/−des-chloro (U.S. Pat. No. 4,294, 757) (prepared by acylation using acyl chlorides).

Specific examples of suitable maytansinol analogues having modifications of other positions include:

(1) C-9-SH (U.S. Pat. No. 4,424,219) (prepared by the reaction of maytansinol with $H_2S$ or $P_2S_5$);

(2) C-14-alkoxymethyl(demethoxy/CH$_2$OR) (U.S. Pat. No. 4,331,598);
(3) C-14-hydroxymethyl or acyloxymethyl (CH$_2$OH or CH$_2$OAc) (U.S. Pat. No. 4,450,254) (prepared from *Nocardia*);
(4) C-15-hydroxy/acyloxy (U.S. Pat. No. 4,364,866) (prepared by the conversion of maytansinol by *Streptomyces*);
(5) C-15-methoxy (U.S. Pat. Nos. 4,313,946 and 4,315,929) (isolated from Trewia nudlflora);
(6) C-18-N-demethyl (U.S. Pat. Nos. 4,362,663 and 4,322,348) (prepared by the demethylation of maytansinol by *Streptomyces*); and,
(7) 4,5-deoxy (U.S. Pat. No. 4,371,533) (prepared by the titanium trichloride/LAH reduction of maytansinol).

Furthermore, U.S. Pat. No. 6,333,410, the entire disclosure of which is hereby incorporated by reference, provides an improved process for the preparation and purification of thiol-containing maytansinoids suitable for linking to cell-binding agents.

Examples of maytansinoids also include, but are not limited to, the following:

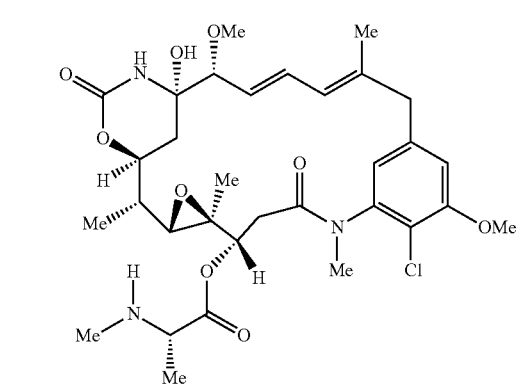
C2

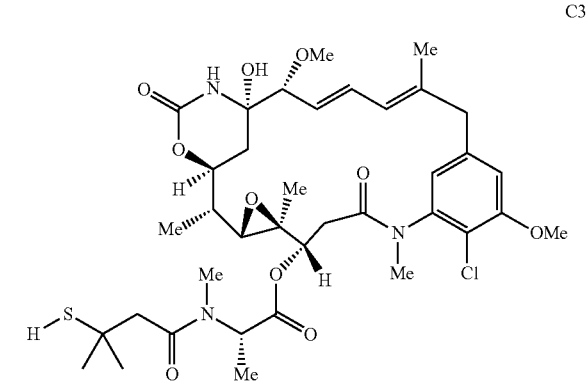
C3

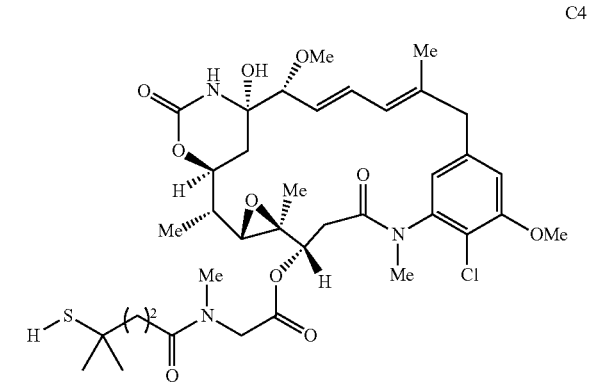
C4

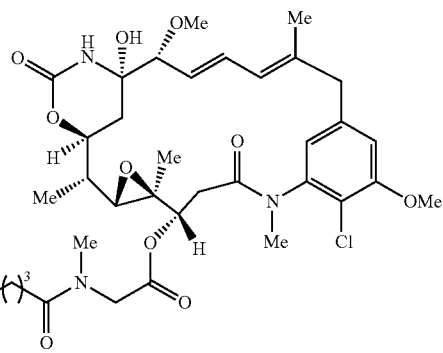
C5

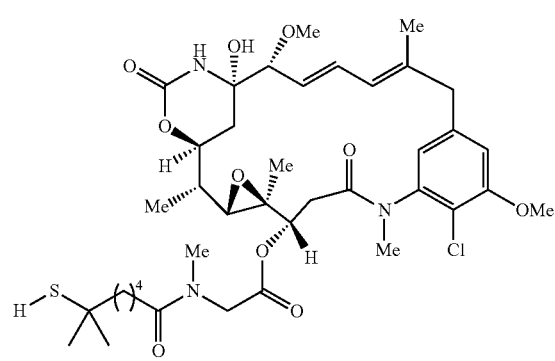
C6

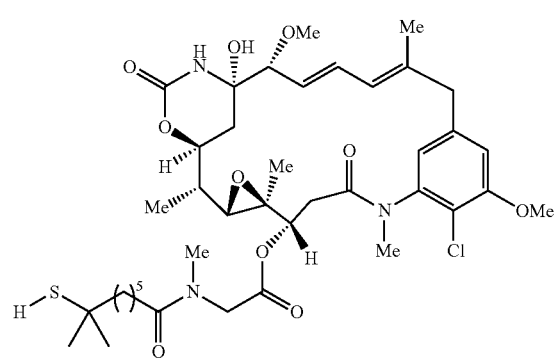
C7

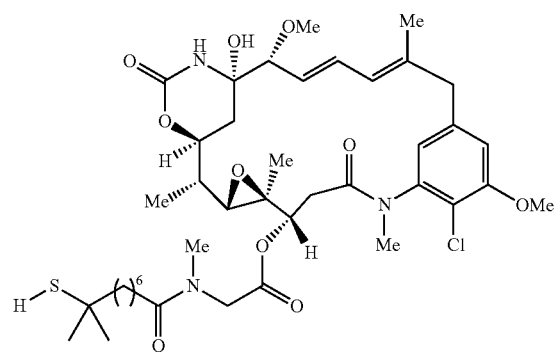
C8

93
-continued
C9
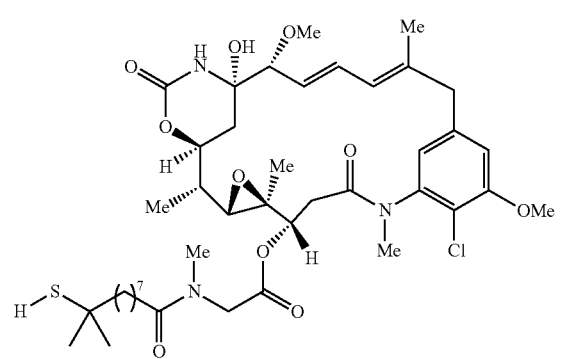
C10
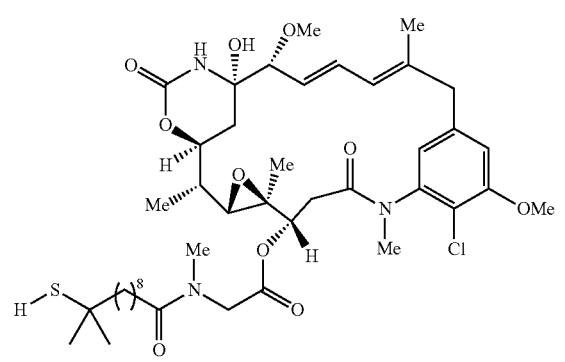
C11
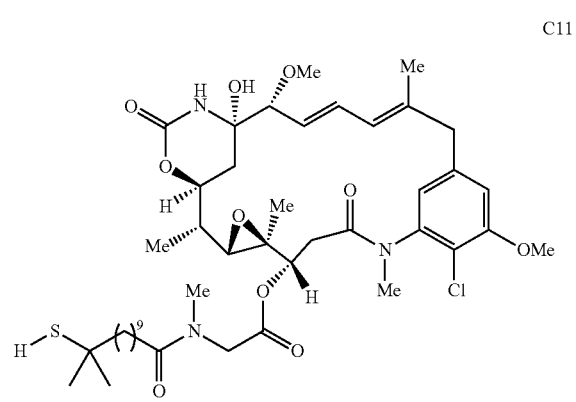
C12
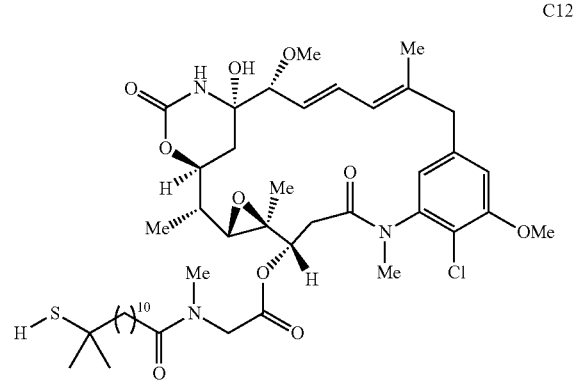
94
-continued
C13
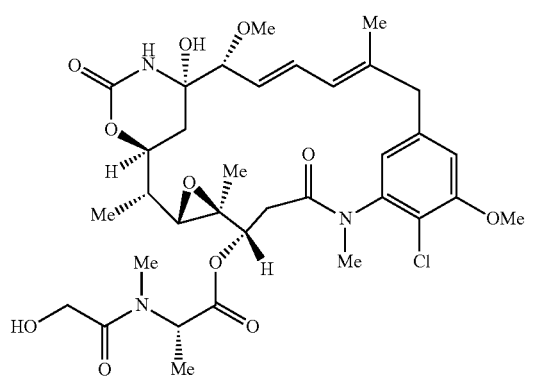
C14
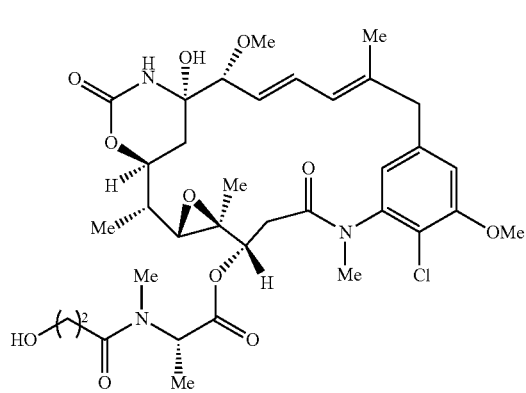
C15
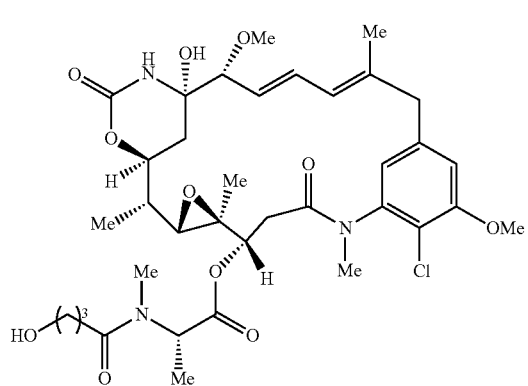
C16
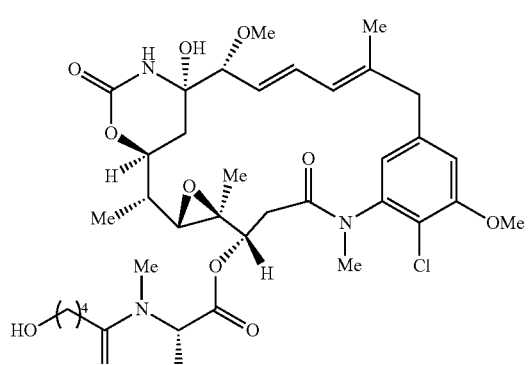

95
-continued
C17
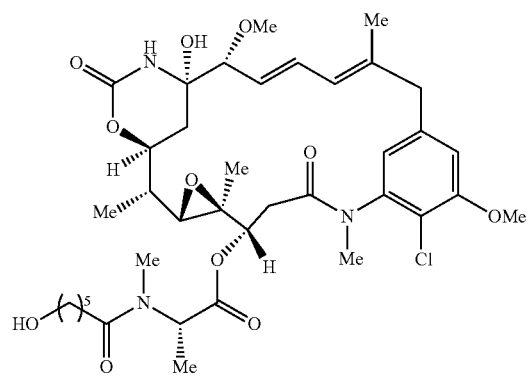
C18
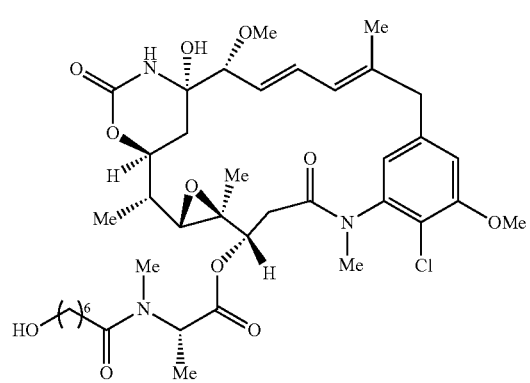
C19
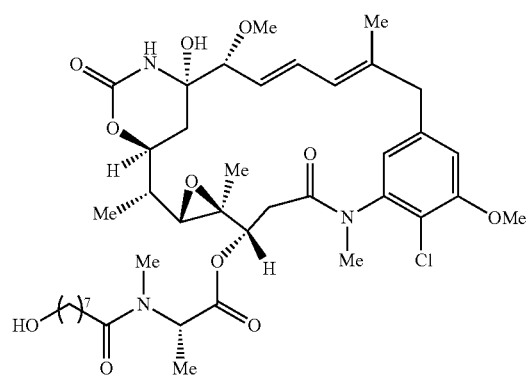
C20
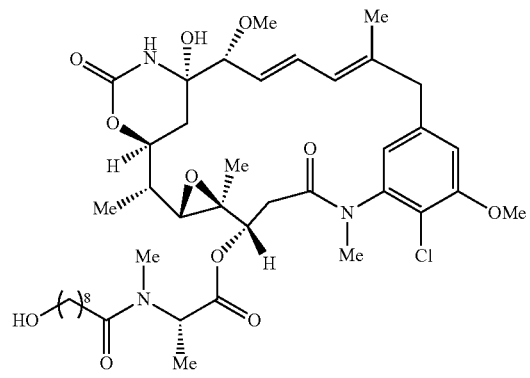
96
-continued
C21
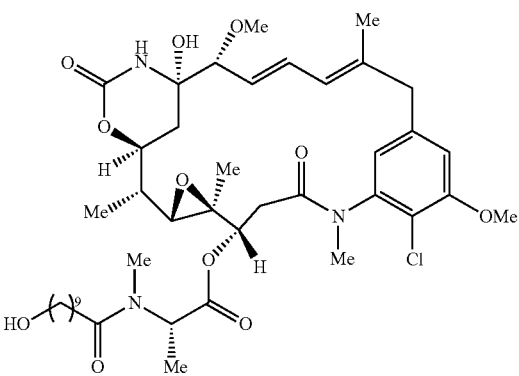
C22
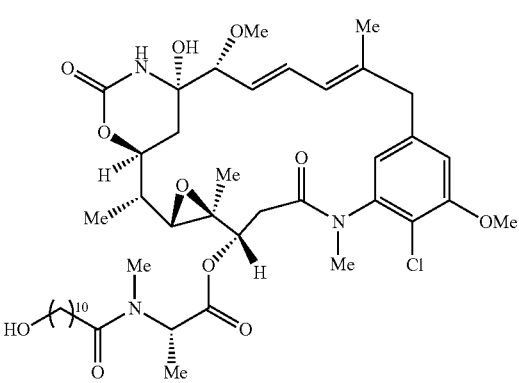
C23
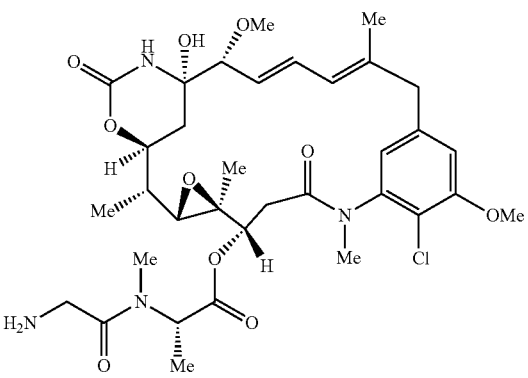
C24
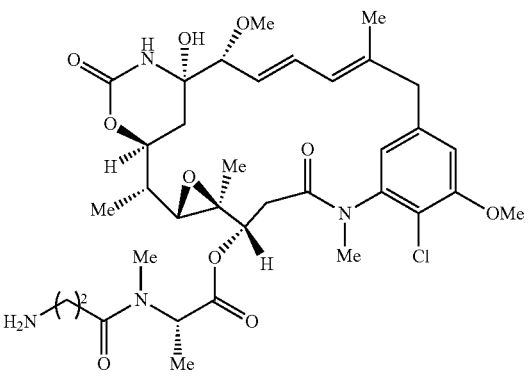

C25
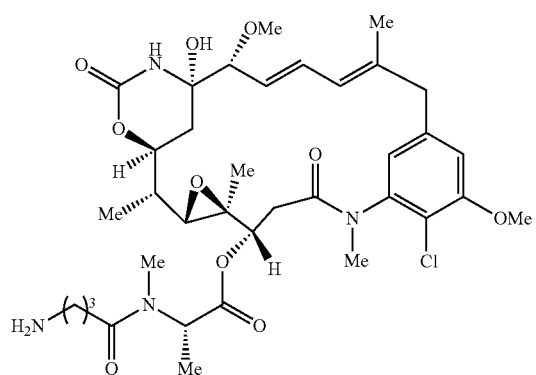
C29
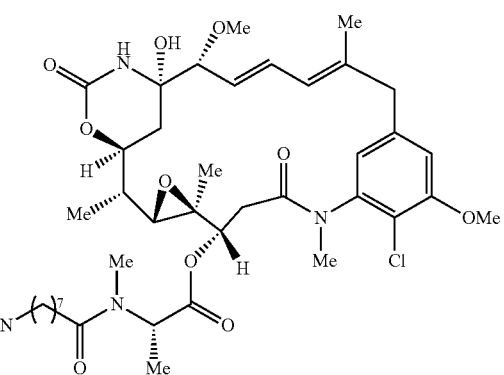
C26
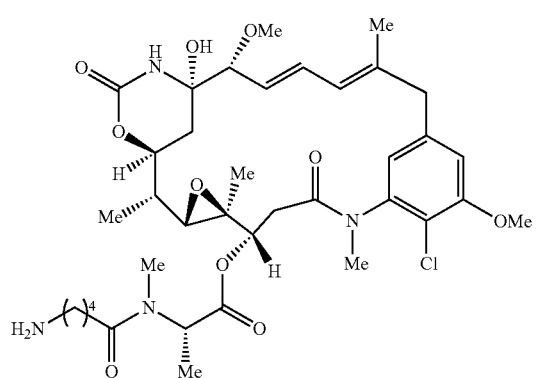
C30
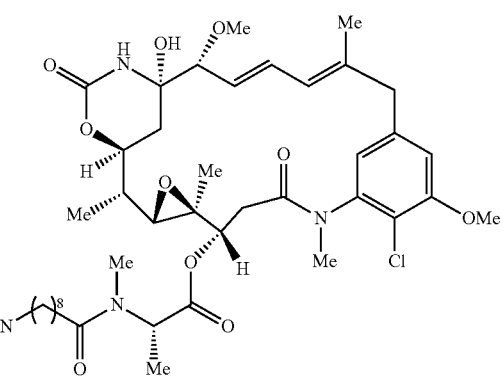
C27
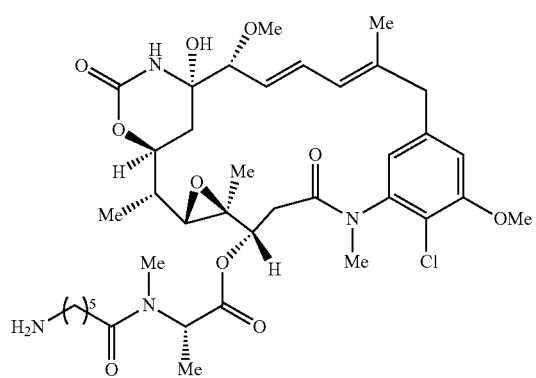
C31
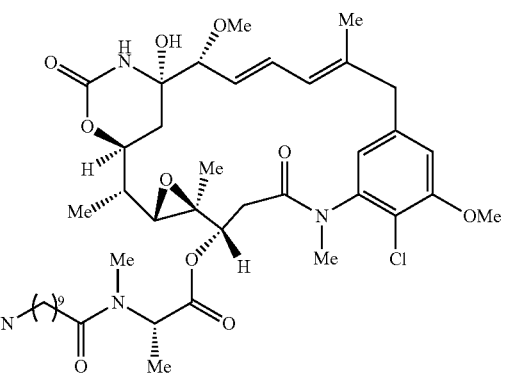
C28
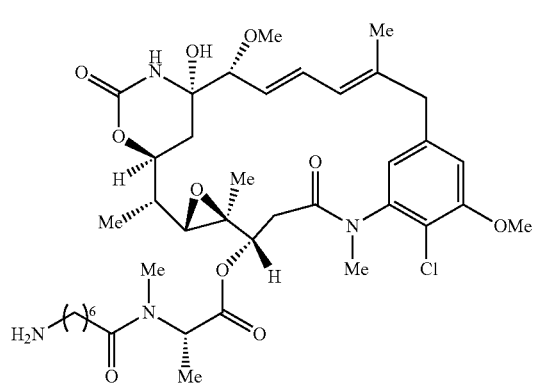
C32
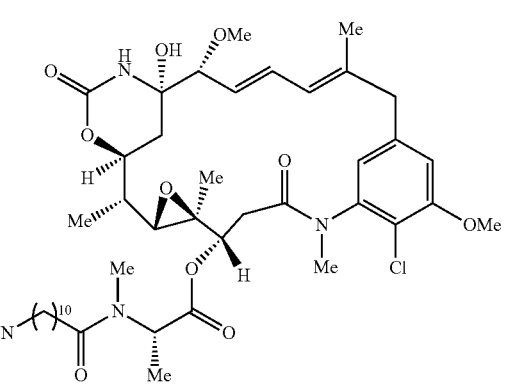

99
-continued
C33
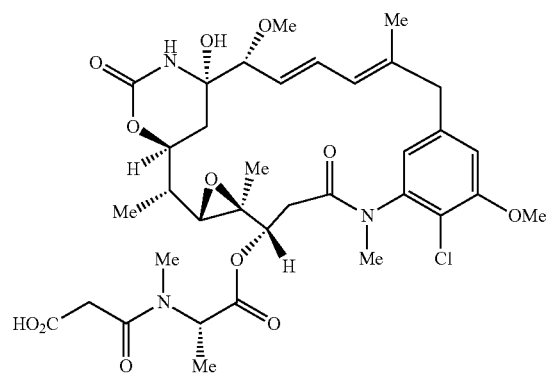
C34
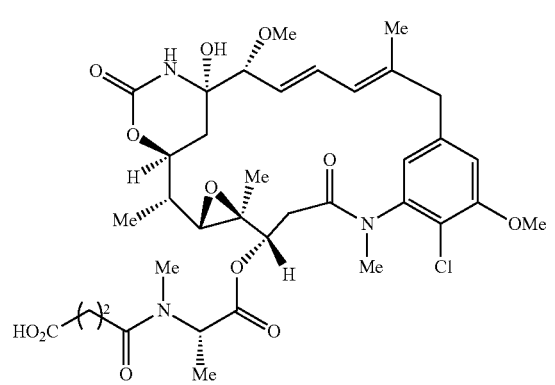
C35
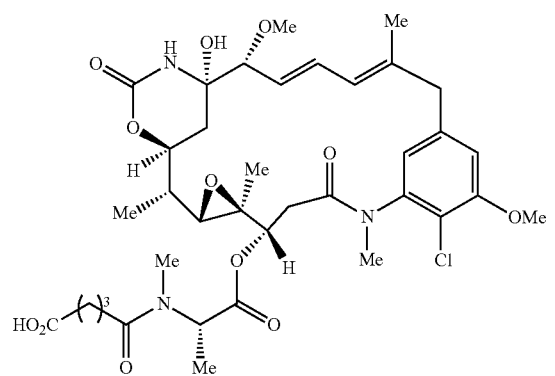
C36
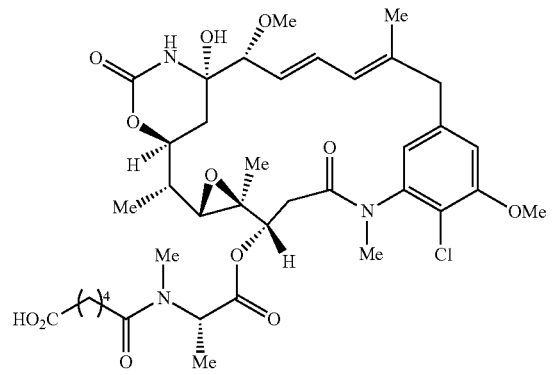
100
-continued
C37
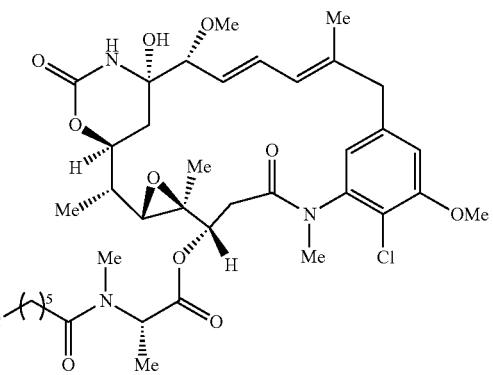
C38
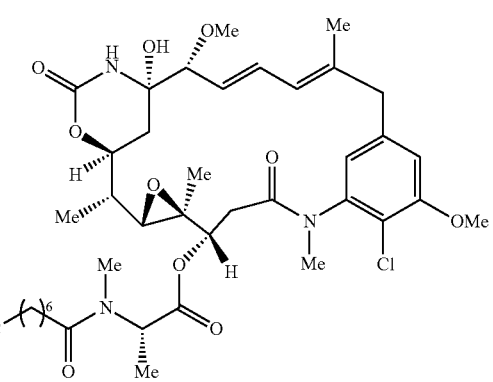
C39
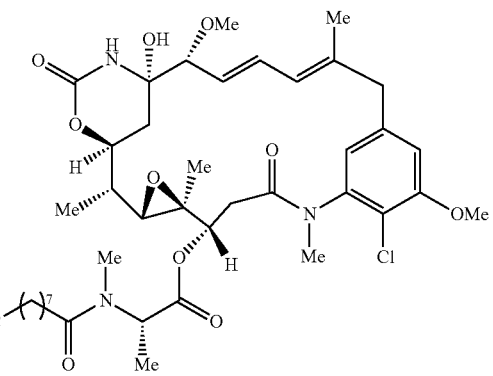
C40
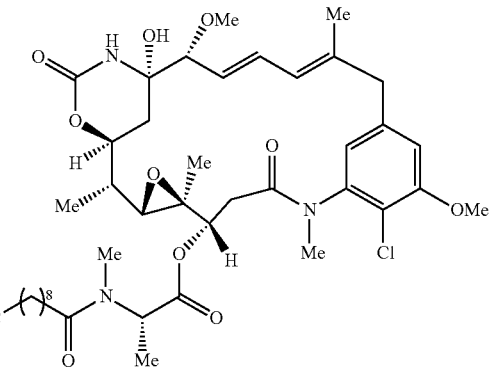

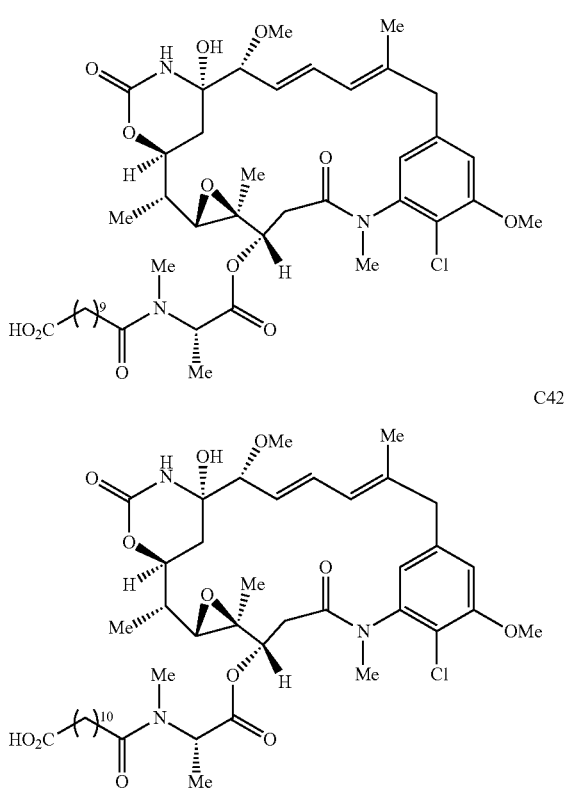

C41

C42

In some of these Maytansinoid embodiments, p is 1-8. In some embodiments, p is 1-6. In some embodiments, p is 1-4. In some embodiments, p is 1-2. In some embodiments, p is 1. Many positions on maytansinol are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable. The C-3 position is preferred.

Cytotoxic agents comprising maytansinoids and their therapeutic use. See, U.S. Pat. Nos. 5,208,020; 5,416,064; 7,276,497; 7,851,432; 7,473,796; 7,601,354; 7,303,749; 8,198,417; 8,163,888; 7,989,598; 8,088,387.

Maytansinoid Attachment Linkage

The C-3 position of maytansinol is preferred. The linking group between linker (E) and a maytansinoid include, but are not limited to, amide, ester, carbamate, carbonate, ether, hydrazone, thioether, and disulfide. In some embodiments, the linking group is an amide. In some embodiments, the linking group is carbamate. In some embodiments, the linking group is an ester. The chemistry resulting in the linking group between the linker and a maytansinoid is generally known in the art. In some embodiments, a maytansinoid can be linked to (E) in a single step. In some embodiments, a maytansinoid can first form a linking group with a fragment of a linker followed by extension of the linker. FIG. 1 and FIG. 2, for example, illustrate non-limiting approaches for linking a maytansinoid to a linker by first forming a amide linking group, followed by extension of the linker.

Biomolecules Including Cell-Binding Agents

The term biomolecule as used herein generally refers to a structure of natural or synthetic origin which exhibits affinity for, or otherwise an ability to bind or interact with, a certain biological target, preferably in vivo. Biomolecules for employment in the present invention are, for example, protein-based entities which exhibit secondary, and in some embodiments tertiary and/or quaternary structures. Biomolecules may have post-translational modification(s) including, for example, glycosylation, phosphorylation, deamidation, and/or oxidation. Ligands and receptors are each example classes of biomolecules for employment in the conjugates of the present invention. Soluble forms of ligands and receptors, for example, generally fusion constructs, are well known in the art, including human IgG1-Fc fusions, for example. Soluble ligand as well as receptor fusion constructs are exemplary classes of biomolecules for employment in the conjugate structures of the present invention. Preferred biomolecules for drug conjugates of the present invention, at this time, are antibodies, particularly monoclonal antibodies (mAb), including bispecific antibodies, and functional fragments thereof. Antibody architecture modifications also represent an example area of biomolecules for use in conjugates of the present invention. See, *Next-Generation Antibodies*, Nature Reviews Drug Discovery, 13:413 (2014). An alternate biomolecule approach is to provide an alternative ligand that can fulfil antibody-like affinity functions, including DARP (designed ankyrin repeat protein) embodiments.

The effectiveness of the conjugates of the invention as therapeutic agents depends on the careful selection of an appropriate cell-binding agent. Cell-binding agents may be of any kind presently known, or that become known and includes peptides and non-peptides. Generally antibodies, ligand fusion constructs, and bispecific antibodies are most preferred. Examples of cell-binding agents include monoclonal antibodies, fragments of antibodies such as Fab, Fab', and F(ab')2, Fv, and, particularly, bispecific antibodies.

Activity and Efficacy

Cell-binding agent maytansinoid conjugates of the invention can be evaluated for their ability to suppress growth and/or proliferation of various cell lines in vitro. For example, cell lines such as the human colon carcinoma line COLO205, the human melanoma cell line A375, the human myeloid leukemia cell line HL60, the human breast carcinoma line SKBR3, or the human epidermoid carcinoma cell line KB can be used for the assessment of cytotoxicity of these conjugates. Cells to be evaluated can be exposed, for example, to the compounds for 24 hours and the surviving fractions of cells measured in direct assays by known methods. See, e.g. Goldmacher et al., 135 J. Immunol. 3648-3651 (1985), and Goldmacher et al., 102 J. Cell Biol. 1312-1319 (1986).) $IC_{50}$ values for growth inbition and/or cell death are calculated from the results of the assays.

Methods of Use

Conjugates described herein can be used in a method for targeting a cytotoxic agent to a selected cell population, the method comprising contacting a cell population or tissue suspected of containing the selected cell population with a cell-binding agent cytotoxic agent conjugate, wherein one or more cytotoxic agents is covalently linked to the cell-binding agent via a linker. The cell-binding agent binds to cells of the selected cell population. Conjugates described herein can also be used in a method of destroying cells, the method comprising contacting the cells with a cell-binding agent maytansinoid conjugate, for example, wherein one or more maytansinoids is covalently linked to the cell-binding agent via a linker, for example, and the cell-binding agent binds to the cells. In some cases, subsequent to binding, CD74, for example, the entire conjugate is internalized by the target cell. Conjugates of the present invention can also be used in a method of treatment of afflictions including but not limited to malignant tumors, autoimmune diseases, graft rejections, graft versus host disease, viral infections, microorganism infections, and parasite infections, the method comprising administering to a subject in need of treatment an effective amount of a cell-binding agent cytotoxic agent conjugate, wherein one or more cytotoxic agents is covalently linked to the cell-binding agent via a linker and the cell-binding agent binds diseased or infected cells of the affliction.

Examples of medical conditions that can be treated according to the methods of the present invention include but are not limited to malignancy of any type including, for example, hematological conditions including blood cancers, MDS, Leukemic conditions, lymphoma, myeloma, cancer of the lung, breast, colon, prostate, kidney, pancreas, ovary, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection.; and other conditions as determined by one of ordinary skill in the art. Conjugates of the present invention can be used to treat oncology conditions, tumors, hematological conditions, particularly B-cell malignancies, multiple myeloma, and B-cell lymphomas, for example.

For clinical in vivo use, conjugates of the present invention can be supplied as a solution or a lyophilized powder that is tested for sterility and toxin levels. Conjugates can be given, for example, weekly for 4 weeks as an intravenous bolus each week. Bolus doses can be given in 50 to 500 ml of normal saline to which 5 to 10 ml of human serum albumin, for example, can be added. Dosages can be 10 mg to 2000 mg per administration, intravenously (range, for example, of 100 ng to 200 mg/kg per day). After one to six (1-6) weeks, for example, two to four (2-4) weeks, for example, of treatment, the patient can continue to receive treatment on a weekly basis.

Conditions of clinical and non-clinical use are readily determined by one of ordinary skill in the art. Specific in vivo clinical protocols with regard to route of administration, excipients, diluents, dosages, times, etc., can be determined by one of ordinary skill in the art as the clinical situation warrants.

Other active agents may be administered along with the conjugate.

Example I

Antibody Drug Conjugation

1. Storage

Protein is stored at −80° C. and drug linker is stored at 4° C. or −20° C. for long-term storage.

2. Calculation

Calculate the amount of protein and drug linker. Protein stock concentration ×1 mg/mL, final desired protein concentration ×2 mg/mL, drug stock concentration ×3 mM, and CB protein to be conjugated ×4 mg. A recommended protein to drug molar ratio is 10:1, but can be as low, e.g., 5:1. Protein MW may cause adjustment of the calculation if it is not 150K.

| Protein stock concentration | mg/mL | 4.5 | 4.5 | X1 |
| Final desired protein concentration | mg/mL | 3 | 3 | X2 |
| Drug stock concentration | mM | 5 | 5 | X3 |
| Protein to be conjugated | mg | 0.1 | 10 | X4 |
| Protein to drug ratio | | 10 | 10 | 10 |
| Protein MW | KDa | 150 | 150 | 150 |
| Final drug linker concentration | uM | 200 | 200 | |
| Reaction volume | uL | 33.3 | 3333.3 | |
| Protein needed for conjugation | uL | 22.2 | 2222.2 | |
| Drug needed for conjugation | uL | 1.3 | 133.3 | |
| PBS buffer needed | uL | 9.8 | 977.8 | |

3. Conjugation

Appropriate amounts of protein and drug linker are prepared at room temperature and mixed for conjugation.

Example 1: [protein stock concentration]=4.5 mg/mL, [final desired protein concentration]=3 mg/mL, [drug stock concentration]=5 mM, 0.1 mg protein for conjugation.

9.8 uL PBS buffer and 1.3 uL drug are added to 22.2 uL protein in a micro tube. Put tube on tube rotator at room temperature (~22° C.) for 16 hours. Typically, this amount of antibody drug conjugate is sufficient for DAR analysis, cell binding and death assays.

Example 2: [protein stock concentration]=4.5 mg/mL, [final desired protein concentration]=3 mg/mL, [drug stock concentration]=5 mM, 10 mg protein for conjugation.

977.8 uL PBS buffer and 133.3 uL drug are added to 2222.2 uL protein in 15 mL centrifuge tube. Put tube on tube rotator at room temperature (~22° C.) for 16 hours conjugation;

Conjugation duration and temperature can vary for different antibody variants. Room temperature and 16 hours are recommended.

4. Free Drug Removal

Free drug can be removed by desalting the conjugation mixture using Thermo scientific zeba spin 7K MWCO deslating columns. Select the column size based on sample volume.

| | Sample volume |
|---|---|
| Zeba Spin Desalting Columns, 7K MWCO, 0.5 mL | 30-130 uL |
| Zeba Spin Desalting Columns, 7K MWCO, 2 mL | 200-700 uL |
| Zeba Spin Desalting Columns, 7K MWCO, 5 mL | 500-2000 uL |
| Zeba Spin Desalting Columns, 7K MWCO, 10 mL | 700-4000 uL |

Example II

Cell Death Assay

Cytotoxicity effects of conjugated biomolecules on target positive cells were measured with a cell proliferation assay. Target positive and target negative cells were obtained from ATCC and maintained in RPMI, high glucose (Cellgro-Mediatech; Manassas, Va.) supplemented with 20% heat-inactivated fetal bovine serum (Hyclone; Thermo Scientific; Waltham, Mass.), 2 mM glutamax (Invitrogen; Carlsbad, Calif.) and 1× Pencillin/streptomycin (Cellgro-Mediatech; Manassas, Va.). A total of 20,000 cells in a volume of 40 μl were seeded in a 96-well half area flat bottom white polystyrene plate on the day of assay. Conjugated leads were formulated at 2× concentration in RPMI medium and filtered through MultiScreen HTS 96-Well Filter Plates (Millipore; Billerica, Mass.). Filter sterilized conjugated leads were added into treatment wells and plates were cultured at 37° C.

in a CO2 incubator for 72 hrs. For cell viability measurement, 80 μl of Cell Titer-Glo® reagent (Promega Corp.; Madison, Wis.) was added into each well, and plates processed as per product instructions. Relative luminescence was measured on an ENVISION® plate reader (Perkin-Elmer; Waltham, Mass.). Relative luminescence readings were converted to % viability using untreated cells as controls. Data was fitted with non-linear regression analysis, using log(inhibitor) vs. response, variable slope, 4 parameter fit equation using GraphPad Prism (GraphPad v 5.00, Software; San Diego, Calif.). Data was expressed as % relative cell viability vs. dose of ADC in nM.

Example III

Synthetic I1

A. Synthesis of Maytan-N-Me-L-Ala Glutaric Acid from Maytan-N-Me-L-Ala

Maytan-N-Me-L-Ala (250 mg, 0.385 mmol) (prepare as per the procedure given in *J. Med. Chem.* 2006, 49, 4392), glutaric anhydride (440 mg, 3.85 mmol) and aqueous saturated $NaHCO_3$ (1 ml) is dissolved in THF (10 ml). The reaction mixture is stirred at room temperature under argon for 2 hrs. The reaction mixture is diluted with water and pH adjusted to 2 with conc. formic acid. The resulting reaction mixture is extracted with ethyl acetate twice. The combined organic layer is washed with brine, dried over anhydrous sodium sulfate and filtered. The crude residue is purified by reverse phase chromatography using C18 column 20-40 micron (50 g), eluted with a gradient (10-95% over 18 mins) of acetonitrile (0.1% AcOH) in water (0.1% AcOH), lyophilized to yield maytan-N-Me-L-Ala glutaric acid 32 (205 mg, 0.268 mmol, 70% yield) as a white solid. MS m/z: 764.7 [MH+], 747.1 [M-18], 786.7 [M+Na]; $^1$H NMR (500 MHz, $CDCl_3$) δ: 0.74 (3H, S), 1.19-1.27 (8H, m), 1.38-1.42 (1H, m), 1.62 (3H, S), 1.80-1.85 (1H, m), 1.91-1.96 (2H, m), 2.12-2.18 (1H, m), 2.30-2.45 (5H, m), 2.55 (1H, t), 2.79 (3H, s), 2.95 (1H, d), 3.05 (1H, d), 3.15 (3H, s), 3.32 (3H, s), 3.44 (1H, d), 3.58 (1H, d), 3.93 (3H, s), 4.24 (1H, t), 4.68-4.72 (1H, m), 5.32 (1H, bs), 5.58-5.63 (1H, m), 6.34-6.39 (1H, m), 6.58-6.65 (2H, m), 6.78 (1H, s).

B. Synthesis of Maytan-N-Me-L-Ala Glutaric Acid NHS Ester from Maytan-N-Me-L-Ala Glutaric Acid A solution of maytan-N-Me-L-Ala glutaric acid (205 mg, 0.268 mmol) is dissolved in dichloromethane (10 ml), and treated with N-hydroxysuccinimide (NHS, 62 mg, 0.54 mmol) and 1-[3-(dimethyamino) propyl]-3-ethylcarbodiimide hydrochloride (EDCI, 128 mg, 0.67 mmol). The reaction mixture is stirred overnight at room temperature under argon. The reaction mixture is washed with water followed by brine, dried over anhydrous sodium sulfate and filtered. The solvent is evaporated under reduced pressure to give the crude residue. The crude residue is purified by reverse phase chromatography using C18 column, 20-40 micron (50 g), eluted with a gradient (10-95% over 18 mins) of acetonitrile (0.1% AcOH) in water (0.1% AcOH), lyophilized to afford maytan-N-Me-L-Ala glutaric acid NHS ester 33 (190 mg, 0.22 mmol, 82% yield) as a white solid. MS m/z: 862.0 [MH+], 844.6 [M-18], 884.0 [M+Na]; $^1$H NMR (500 MHz, $CDCl_3$) δ: 0.73 (3H, s), 1.16-1.24 (8H, m), 1.35-1.42 (1H, m), 1.45-1.54 (4H, m), 1.58 (3H, s), 1.85-1.91 (1H, m), 2.01-2.12 (2H, m), 2.29-2.36 (2H, m), 2.42-2.57 (3H, m), 2.62 (2H, t), 2.78 (3H, s), 2.98 (1H, d), 3.05 (1H, d), 3.12 (3H, s), 3.21 (1H, bs), 3.29 (3H, s), 3.43 (1H, d), 3.56 (1H, d), 3.92 (3H, s), 4.21 (1H, t), 4.71 (1H, dd), 5.28-5.34 (1H, m), 5.57-5.63 (1H, m), 6.15 (1H, s), 6.33-6.38 (1H, m), 6.58 (1H, s), 6.67 (1H, d), 6.75 (1H, s).

C. Synthesis of Maytan-N-Me-L-Ala Glutaric PEG4-Acid from Maytan-N-Me-L-Ala Glutaric Acid NHS Ester A solution of maytan-N-Me-L-Ala glutaric acid NHS ester (190 mg, 0.22 mmol) and amino-PEG4-acid (133 mg, 0.50 mmol) are dissolved in a mixture of acetonitrile (25 ml) and water (8 ml) and treated with aqueous saturated $NaHCO_3$ (6 ml). The reaction mixture is stirred overnight at room temperature under argon and concentrated under reduced pressure. The crude residue is purified by reverse phase chromatography using C18 column, 20-40 micron (50 g), eluted with a gradient (10-95% over 18 mins) of acetonitrile (0.1% AcOH) in water (0.1% AcOH), lyophilized to yield maytan-N-Me-L-Ala glutaric PEG4 acid (170 mg, 0.168 mmol, 76% yield) as a white solid. MS m/z: 1012.7 [MH+], 995.4 [M-18], 1034.2 [M+Na]; $^1$H NMR (500 MHz, $CDCl_3$) δ: 0.73 (3H, s), 1.13-1.28 (8H, m), 1.32-1.42 (1H, m), 1.53-1.61 (5H, m), 1.78-1.85 (1H, m), 1.89-1.95 (1H, m), 2.08-2.13 (1H, m), 2.15-2.28 (3H, m), 2.39-2.47 (1H, m), 2.49-2.55 (2H, m), 2.82 (3H, s), 2.93 (1H, d), 3.05 (1H, d), 3.12 (3H, s), 3.29-3.38 (5H, m), 3.42 (1H, d), 3.50-3.61 (16H, m), 3.66-3.72 (2H, m), 3.95 (3H, s), 4.23 (1H, t), 4.71-4.77 (1H, m), 5.13-5-19 (1H, bs), 5.57-5.62 (1H, m), 6.32-6.38 (2H, m), 6.51-6.59 (2H, m), 6.75 (1H, s).

D. Synthesis of Maytan-N-Me-L-Ala Glutaric PEG4-Acid NHS Ester from Maytan-N-Me-L-Ala Glutaric PEG4-Acid A solution of maytan-N-Me-L-Ala glutaric PEG4 acid (170 mg, 0.168 mmol) is dissolved in dichloromethane (15 ml), and treated with N-hydroxysuccinimide (NHS, 39 mg, 0.336 mmol) and 1-[3-(dimethyamino) propyl]-3-ethylcarbodiimide hydrochloride (EDCI, 81 mg, 0.42 mmol). The reaction mixture is stirred overnight at room temperature under argon and concentrated under reduced pressure. The crude residue is purified by reverse phase chromatography using C18 column, 20-40 micron (50 g), eluted with a gradient (10-95% over 18 mins) of acetonitrile (0.1% AcOH) in water (0.1% AcOH), lyophilized to give maytan-N-Me-L-Ala glutaric PEG4-acid NHS ester (150 mg, 0.135 mmol, 80%) as a white solid. MS m/z: 1109.6 [MH+], 1092.5 [M-18], 1131.3 [M+Na]; $^1$H NMR (500 MHz, $CDCl_3$) δ: 0.74 (3H, s), 1.14-1.27 (8H, m), 1.34-1.42 (1H, m), 1.43-1.52 (4H, m), 1.59 (3H, s), 1.77-1.84 (1H, m), 1.88-1.96 (1H, m), 2.10-2.18 (3H, m), 2.21-2.28 (1H, m), 2.37-2.43 (1H, m), 2.53 (1H, t), 2.82-2.88 (4H, m), 2.96 (1H, d), 3.05 (1H, d), 3.15 (3H, s), 3.29-3.36 (5H, m), 3.42-3.49 (4H, m), 3.52-3.61 (16H, m), 3.78 (1H, t), 3.92 (3H, s), 4.20 (1H, t), 4.69-4.73 (1H, m), 5.28 (1H, bs), 5.55-5.63 (1H, m), 6.18 (1H, s), 6.32-6.40 (1H, m), 6.60-6.68 (2H, m), 6.75 (1H, s).

E. Synthesis of Maytan-N-Me-L-Ala Glutaric PEG4-DIBCO (I1) from Maytan-N-Me-L-Ala Glutaric PEG4 Acid NHS Ester A solution of maytan-N-Me-L-Ala glutaric PEG4 acid NHS ester (150 mg, 0.135 mmol) and tricyclic amine (55 mg, 0.173 mmol) are dissolved in a mixture of acetonitrile (12 ml) and water (4 ml) and treated with aqueous saturated NaHCO$_3$ (3 ml). The reaction mixture is stirred overnight at room temperature under argon and concentrated under reduced pressure. The crude residue is purified by reverse phase chromatography using C18 column, 20-40 micron (50 g), eluting with a gradient (10-95% over 18 mins) of acetonitrile (0.1% AcOH) in water (0.1% AcOH), lyophilized to obtain maytan-N-Me-L-Ala glutaric PEG4-DIBCO (105 mg, 0.08 mmol, 60% yield) as a white solid. MS m/z: 1312.9 [MH+], 1295.4 [M-18], 1334.6 [M+Na]; $^1$H NMR (500 MHz, CDCl$_3$) δ: 0.82 (3H, s), 1.01-1.08 (2H, m), 1.23-1.32 (8H, m), 1.39-1.51 (3H, m), 1.58-1.66 (4H, m), 1.88-1.96 (2H, m), 1.98-2.03 (1H, m), 2.19-2.26 (4H, m), 2.30-2.36 (1H, m), 2.42 (2H, t), 2.47-2.52 (1H, m), 2.59-2.65 (1H, m), 2.88 (3H, s), 3.02-3.14 (4H, m), 3.21 (3H, s), 3.35-3.43 (5H, m), 3.49-3.52 (3H, m), 3.58-3.70 (18H, m), 4.00 (3H, s), 4.31 (1H, t), 4.79-4.82 (1H, m), 5.17 (1H, d), 5.33 (1H, bs), 5.65-5.70 (1H, m), 6.19 (1H, dd), 6.26 (1H, d), 6.32 (1H, dd), 6.41-6.47 (1H, m), 6.68-6.71 (2H, m), 6.84 (1H, s), 7.31-7.44 (7H, m), 7.70-7.72 (1H, m).

F. Synthesis of 6-(2, 2, 2-Trifluoroacetylamino) hexanoic acid from 6-Aminohexanoic acid Ethyl trifluroacetate (5.7 mL, 6.8 g, 48 mmol) and triethylamine (5.4 mL, 3.9 g, 39 mmol) are added to a suspension of 6-aminohexanoic acid (5.00 g, 38.1 mmol) in dry methanol (19 mL). The reaction mixture is stirred for 17 hours at room temperature under argon. Ether (100 mL) is then added, and washed with 100 mL aqueous 2M HCl. The aqueous layer is twice extracted with 100 mL ether. The organic layers are combined, washed with 150 mL brine and dried over anhydrous sodium sulfate. After filtering, concentrating and drying under vacuum, product (8.66 g, 100%, 38.1 mmol) is obtained as an off-white solid. MS (ESI+) m/z: 228 [M$^+$+H$^+$]; MS (ESI-) m/z: 226 [M$^-$-H$^-$]; $^1$HNMR (300 MHz, DMSO-d$_6$) δ:1.21-1.29 (2H, m), 1.41-1.53 (4H, m), 2.16-2.21 (2H, t), 3.12-3.18 (2H, q), 9.39 (1H, s, br), 11.99 (1H, s).

G. Synthesis of 6-(2, 2, 2-Trifluoro-acetylamino)-hexanoyl chloride from 6-(2,2,2-Trifluoroacetylamino)hexanoic acid A suspension of Maytan-N-Me-L-Ala glutaric PEG4-DIBCO (8.66 g, 38.1 mmol) in methylene chloride (190 mL) is cooled to 0° C. Oxalyl chloride (16.1 mL, 24.2 g, 190 mmol) added dropwise over 6 minutes. DMF (8 drops) is then added. The reaction mixture is stirred at 0° C. for 1 hour, and then at room temperature for 2.5 hours. It is then concentrated and dried under vacuum to yield product (9.36 g, 100%, 38.1 mmol) as a light amber syrup. $^1$H NMR (300 MHz, CDCl$_3$) δ: 1.36-1.46 (2H, m), 1.57-1.67 (2H, m), 1.70-1.80 (2H, m), 2.89-2.94 (2H, t), 3.34-3.41 (2H, q), 6.40 (1H, br).

H. Synthesis of Dibenzo[a,d]cyclohepten-5-one oxime from Dibenzo[a,d]cyclohepten-5-one A solution of Dibenzo[a,d]cyclohepten-5-one (25.0 g, 121 mmol) and hydroxylamine HCl (12.6 g, 181 mmol) in pyridine (70 mL) is refluxed for 15.5 hrs. The reaction mixture is allowed to cool to room temperature and concentrated in vacuo. The residue is partitioned between 300 mL 5% aqueous HCl/ice and 200 mL ethyl acetate. The aqueous layer is twice extracted with 150 mL ethyl acetate. The organic layers are combined and washed with 250 mL brine. After drying with anhydrous sodium sulfate, filtering, concentrating and drying, product is obtained as a light yellow-beige solid (26.8 g, 121 mmol). MS (ESI+) m/z: 222 [M$^+$+H$^+$]; MS (ESI-) m/z: 220 [M$^-$-H$^-$]; $^1$HNMR (300 MHz, CDCl$_3$) 6.91-6.92 (2H, d), 7.33-7.43 (6H, m), 7.56-7.61 (1H, m), 7.65-7.68 (1H, m), 8.55 (1H, s).

I. From dibenzo[a,d]cyclohepten-5-one oxime to 5,6-Dihydro-dibenzo[b,f]azocine A solution of diisobutylaluminum hydride in dichloromethane (1.0 M, 192 mL) is cooled on a water bath and solid dibenzo[a,d]cyclohepten-5-one oxime, (8.48 g, 38.3 mmol) is added in portions at a rate to maintain the temperature between 15° C. and 27° C. The water bath is removed and the resultant solution is stirred at ambient temperature for 3 days. The solution is cooled on a water bath and solid sodium sulfate decahydrate (20.4 g, 63.3 mmol) is added in portions at a rate to maintain the temperature between 12° C. and 30° C. Celite is added and the mixture is stirred at ambient temperature for 1 hour. The inorganics are separated by filtration and washed generously with ethyl acetate. The organic solutions are combined and the solvents evaporated in vacuo. The residue is applied to a silica gel column (150 g) and eluted with a gradient of dichloromethane (20% to 100%) in hexanes to afford the product, 5.0 g (63%), as a yellow solid. MS m/z: 208.4 MH$^+$; $^1$H NMR (300 MHz, CDCl$_3$) δ: 4.29 (1H, br s), 4.59 (2H, s), 6.39 (1H, d), 6.50 (1H, d of d), 6.58 (1H, d), 6.61-6.66 (1H, m), 6.89-6.95 (1H, m), 7.00 (1H, d of d), 7.19-7.32 (4H, m).

J. Synthesis of N-[6-(6H-Dibenzo[b,f]azocin-5-yl)-6-oxo-hexyl]-2,2,2-trifluoro-acetamide (26) from 5,6-Dihydro-dibenzo[b,f]azocine and 6-(2,2,2-Trifluoro-acetylamino)-hexanoyl chloride Pyridine (8.5 mL, 8.3 g, 110 mmol) is added to a solution of 5,6-Dihydro-dibenzo[b,f]azocine (7.29 g, 35.2 mmol) in dry methylene chloride (72 mL). Next added is 6-(2,2,2-Trifluoro-acetylamino)-hexanoyl chloride (10.7 g, 45.6 mmol) in 25 mL methylene chloride over 4 minutes. The reaction mixture is stirred at room temperature for about 2 hours then diluted with 180 mL methylene chloride and washed with 3×150 mL water. The organic layer is washed with 150 mL brine, dried with anhydrous sodium sulfate, filtered and concentrated. The crude product is flash chromatographed (Isco) on a 330 g silica gel cartridge with 0-50% ethyl acetate/hexane. After concentrating and drying, 14.0 g (95.9%, 33.6 mmol) of pure product is obtained as a very pale, clear amber gum. MS (ESI+) m/z: 417 [M$^+$+H$^+$], MS (ESI-) m/z: 415 [M$^-$-H$^-$]; $^1$HNMR (300 MHz, DMSO-d$_6$) δ 0.95-1.03 (2H, m), 1.22-1.37 (4H, m), 1.69-1.79 (1H, m), 1.87-1.97 (1H, m), 3.00-3.06 (2H, q), 4.14-4.19 (1H, d), 5.34-5.39 (1H, d), 6.61-6.65 (1H, d), 6.74-6.78 (1H, d), 7.15-7.19 (3H, m), 7.27-7.38 (5H, m), 9.31 (1H, br).

K. Synthesis of N-[6-(11,12-Dibromo-11,12-dihydro-6H-dibenzo[b,f]azocin-5-yl)-6-oxo-hexyl]-2,2,2-trifluoro-acetamide from N-[6-(6H-Dibenzo[b,f]azocin-5-yl)-6-oxo-hexyl]-2,2,2-trifluoro-acetamide Pyridinium tribromide (8.48 g, 26.5 mmol) is added to a solution of N-[6-(6H-Dibenzo[b,f]azocin-5-yl)-6-oxo-hexyl]-2,2,2-trifluoro-acetamide (9.95 g, 23.9 mmol), in methylene chloride (200 mL). The reaction mixture is stirred at room temperature under argon for 4.5 hr then washed with 1) 2×120 mL 0.5M aqueous HCl 2) 120 mL water and 3) 120 mL brine. After drying with anhydrous sodium sulfate, filtering and concentrating, the crude product is flash chromatographed (Isco) on 330 g silica gel cartridge with 0-50% ethyl acetate hexane. After concentrating and drying, product is twice dissolved in 150 mL methylene chloride and concentrated. It is dried in vacuo to give 10.5 g (76.1%, 18.2 mmol) of product as very pale slate grey foam. MS (ESI+) m/z: 577 [M$^+$+H$^+$]; MS (ESI–) m/z: 575 [M$^-$-H$^-$]; $^1$HNMR (300 MHz, DMSO-d$_6$) δ: 1.13-1.20 (2H, m), 1.35-1.59 (4H, m), 1.95-2.29 (2H, m), 3.07-3.13 (2H, q), 4.17-5.08 (1H, m), 5.69-5.87 (2H, m), 6.97-7.31 (7H, m), 7.55-7.65 (1H, m), 9.33 (1H, s).

L. Synthesis of N-(6-Trifluoroacetamidohexanoyl)-5,6-dihydro-11,12-didehydrobenzo[b,f]azocine from N-[6-(11,12-Dibromo-11,12-dihydro-6H-dibenzo[b,f]azocin-5-yl)-6-oxo-hexyl]-2,2,2-trifluoro-acetamide A solution of N-[6-(11,12-Dibromo-11,12-dihydro-6H-dibenzo[b,f]azocin-5-yl)-6-oxo-hexyl]-2,2,2-trifluoro-acetamide (6.76 g, 11.7 mmol) in dry THF (31 mL) is added to 1M potassium tert-butoxide/THF solution (35 mL, 35 mmol). The reaction mixture is stirred at room temperature under argon for 2 hours. About 8.5 mL water is slowly added to quench the reaction, and it is diluted with about 180 mL ethyl acetate. This is then washed with 200 mL 1% aqueous HCL, 200 mL water and 200 mL brine. The organic layer is dried with anhydrous sodium sulfate, filtered and concentrated. The crude product is purified by flash chromatography (Isco) on a 120 g silica gel cartridge with 0-10% ethyl acetate/methylene chloride. After concentrating and drying, product is obtained as a coral-colored gum/foam (3.05 g, 62.8%, 7.36 mmol). MS (ESI–) m/z: 413 [M$^-$-H$^-$]; $^1$H NMR (300 MHz, CDCl$_3$) δ 0.96-1.15 (2H, m), 1.23-1.49 (4H, m), 1.88-1.98 (1H, m), 2.04-2.26 (1H, m), 3.02-3.27 (2H, m), 3.64-3.69 (1H, d), 5.14-5.18 (1H, d), 6.58 (1H, br), 7.24-7.44 (7H, m), 7.68-7.70 (1H, d).

M. Synthesis of N-(6-Aminohexanoyl)-5,6-dihydro-11,12-didehydrodibenzo[b,f]azocine from N-(6-Trifluoroacetamidohexanoyl)-5,6-dihydro-11,12-didehydrobenzo[b,f]azocine A solution of potassium carbonate (1.00 g, 7.24 mmol) in water (7.5 mL) is slowly added to solution of N-(6-Trifluoroacetamidohexanoyl)-5,6-dihydro-11,12-didehydrobenzo[b,f]azocine (1.04 g, 2.51 mmol) in methanol (10 mL). The reaction mixture is stirred at room temperature for 49 hours. It is concentrated and partitioned in 40 mL chloroform/40 mL brine. The aqueous layer is extracted with 40 mL chloroform. The organic layers are combined, and 40 mL ethyl acetate is added to aid in solubility. After drying with anhydrous sodium sulfate, filtering, and concentrating, the crude product is purified by reverse phase flash chromatography (Isco) in 2 injections using a 275 g C18 column, 20-40 micron eluted with 5-95% acetonitrile (0.1% AcOH)/water (0.1% AcOH). After lyophilization, product is obtained as the acetic acid salt (light yellow-beige foam: 0.577 g, 60.7%, 1.52 mmol). MS (ESI+) m/z: 319 [M$^+$+H$^+$]. $^1$H NMR (300 MHz, CDCl$_3$) δ 0.98-1.07 (2H, m), 1.27-1.44 (4H, m), 1.85-1.95 (4H, m), 2.14-2.23 (4H, m), 2.54-2.59 (2H, t), 3.62-3.67 (2H, d), 5.13-5.17 (1H, d), 6.20 (3H, br), 7.23-7.42 (7H, m), 7.67-7.70 (1H, d).

Example IV

Synthetic I4

A. Synthesis of Maytan-N-Me-L-Ala Glutaric N-Me-PEG4-N-Me-DIBCO (14) from Maytan-N-Me-L-Ala Glutaric Acid NHS Ester and DIBCO-Dimethyl-PEG4-Amine A solution of maytan-N-Me-L-Ala glutaric acid NHS ester (160 mg, 0.186 mmol) and DIBCO-dimethyl-PEG4-amine (210 mg, 0.354 mmol) are dissolved in a mixture of acetonitrile (5 ml) and water (1 ml) is treated with aqueous saturated NaHCO$_3$ (0.5 ml). The reaction mixture is stirred overnight at room temperature under argon and then concentrated under reduced pressure. The crude residue is purified by reverse phase chromatography using C18 column, 20-40 micron (50 g), eluting with a gradient (10-95% over 18 min) of acetonitrile (0.1% AcOH) in water (0.1% AcOH), lyophilized to obtain maytan-N-Me-L-Ala glutaric N-Me-PEG4-N-Me-DIBCO (I4) (135 mg, 0.10 mmol, 54% yield) as a white solid. MS m/z: 1340.9 [MH+], 1323.4 [M-18], 1362.6 [M+Na]; $^1$H NMR (500 MHz, CDCl$_3$) δ: 0.82 (3H, s), 0.99-1.01 (2H, m), 1.26-1.33 (8H, m), 1.42-1.48 (3H, m), 1.60-1.67 (4H, m), 1.88-1.96 (2H, m), 1.98-2.03 (1H, m), 2.11 (3H, s), 2.19-2.21 (2H, m), 2.36-2.38 (2H, m), 2.42-2.44 (1H, m), 2.53-2.64 (5H, m), 2.82-2.90 (6H, m), 3.00-3.14 (5H, m), 3.19-3.22 (4H, m), 3.38 (3H, s), 3.47-3.70 (17H, m), 3.78 (2H, m), 4.00 (3H, s), 4.31 (1H, t), 4.78-4.81 (1H, m), 5.19 (1H, d), 5.40 (1H, bs), 5.67-5.72 (1H, m), 6.35 (1H, s), 6.42-6.48 (1H, m), 6.70-6.76 (2H, m), 6.85 (1H, s), 7.29-7.44 (8H, m), 7.72-7.74 (1H, m).

B. Synthesis of 3-[2-(2-{2-[2-(2, 2, 2-Trifluoro-acetylamino)-ethoxy]-ethoxy}-ethoxy)-ethoxy]-propionic acid from 3-(2-{2-[2-(2-Amino-ethoxy)-ethoxy]-ethoxy}-ethoxy)-propionic acid and ethyl trifluoroacetate Ethyl trifluoroacetate (1.4 mL, 1.7 g, 12 mmol) and triethylamine (1.3 mL, 0.94 g, 9.3 mmol) are added to a solution of 3-(2-{2-[2-(2-Amino-ethoxy)-ethoxy]-ethoxy}-ethoxy)-propionic acid (2.43 g, 9.16 mmol) in methanol (8.0 mL). The reaction mixture is stirred at room temperature under argon for 17.5 hours and concentrated. The crude product is then purified by reverse phase flash chromatography (Isco) on a 275 g C18 Isco gold column with 5-95% acetonitrile/water (with 0.1% acetic acid). After lyophilization, the product is obtained as pale yellow syrup (1.79 g, 54.1%, 4.95 mmol). MS m/z MH$^+$ 362; $^1$H NMR (300 MHz, DMSO-d$_6$) δ: 2.40-2.45 (2H, t), 3.32-3.36 (2H, m), 3.47-3.51 (14H, m), 3.56-3.60 (2H, m), 9.47 (1H, br), 12.15 (1H, br).

C. Synthesis of 3-[2-(2-{2-[2-(2, 2, 2-trifluoro-acetylamino)-ethoxy]-ethoxy}-ethoxy)-ethoxy]-propionic acid methyl ester from 3-[2-(2-{2-[2-(2, 2, 2-trifluoro-acetylamino)-ethoxy]-ethoxy}-ethoxy)-ethoxy]-propionic acid A solution of 3-[2-(2-{2-[2-(2,2,2-trifluoro-acetylamino)-ethoxy]-ethoxy}-ethoxy)-ethoxy]-propionic acid (0.520 g, 1.43 mmol) in dichloromethane (10 mL) and methanol (5 mL) is treated with a 2M solution of (trimethylsilyl)diazomethane in diethyl ether (1 mL, 2 mmol) and stirred at rt for 1 hour. An additional aliquot of a 2M solution of (trimethylsilyl) diazomethane in diethyl ether (1 mL, 2 mmol) is added and the solution stirred at r.t. for 1 day. The solvents are evaporated in vacuo. The product is applied to a silica gel column (40 g) and eluted with a gradient (1-10%) methanol in dichloromethane to afford final product as a pale yellow oil, 0.536 g (100%). MS (ESI+) m/z: 376.0 [MH$^+$]. $^1$H NMR (300 MHz, CDCl$_3$) δ: 2.60 (2H, t), 3.51-3.56 (2H, m), 3.60-3.64 (14H, m), 3.66 (3H, s), 3.73 (2H, t) and 7.86 (1H, br s).

D. Synthesis of 3-{2-[2-(2-{2-[methyl-(2,2,2-trifluoro-acetyl)-amino]-ethoxy}-ethoxy)-ethoxy]-ethoxy}-propionic acid methyl ester from 3-[2-(2-{2-[2-(2,2,2-trifluoro-acetylamino)-ethoxy]-ethoxy}-ethoxy)-ethoxy]-propionic acid methyl ester A solution of 3-[2-(2-{2-[2-(2,2,2-trifluoro-acetylamino)-ethoxy]-ethoxy}-ethoxy)-ethoxy]-propionic acid methyl ester 175 (0.290 g, 0.77 mmol) in DMF (4 mL, is treated with potassium carbonate (0.320 g, 2.31 mmol) and methyl iodide (0.287 mL, 4.63 mmol), and the resultant mixture is stirred at rt for 1 day. The mixture is cooled on an ice bath and treated with cold 1N hydrochloric acid (1 mL). The resultant solution is applied to a reverse phase C18 column, 20-40 micron (50 g) and eluted with a gradient (5-95%) of acetonitrile (0.1% AcOH) in water (0.1% AcOH) and lyophilized to afford product, 0.217 g (72%) as a colorless oil, 0.29 g (64%). LCMS (ESI+) m/z: 390.0 [MH$^+$]. $^1$HNMR (300 MHz, CDCl$_3$) δ: 2.60 (2H, t), 3.21 (2H, q), 3.58-3.70 (17H, m) superimposed on 3.68 (3H, s) and 3.75 (2H, t).

E. Synthesis of 3-(2-{2-[2-(2-methylamino-ethoxy)-ethoxy]-ethoxy}-ethoxy)-propionic acid sodium salt from 3-{2-[2-(2-{2-[methyl-(2, 2,2-trifluoro-acetyl)-amino]-ethoxy}-ethoxy)-ethoxy]-ethoxy}-propionic acid methyl ester A solution of 3-{2-[2-(2-{2-[methyl-(2,2,2-trifluoro-acetyl)-amino]-ethoxy}-ethoxy)-ethoxy]-ethoxy}-propionic acid methyl ester (0.433 g, 1.1 mmol) in methanol (1 mL) is treated with 1M aqueous sodium hydroxide (2.9 mL, 2.9 mmol) and heated at 60° C. for 2 hours. The solution is cooled to rt and the solvents evaporated in vacuo. The material is dissolved in acetonitrile, and the solvent is evaporated in vacuo (repeated twice). The resultant residue is dried under vacuum, and used without further purification in the subsequent step. MS (ESI+) m/z: 280.4 [MH$^+$]. $^1$H NMR (300 MHz, DMSO-d$_6$) δ: 1.89 (2H, t), 1.94-1.99 (6H, m), 2.99-3.14 (10H, m), 2.95 (6H, d) and 8.90 (1H, br s).

F. Synthesis of 3-{2-[2-(2-{2-[methyl-(2, 2, 2-trifluoro-acetyl)-amino]-ethoxy}-ethoxy)-ethoxy]-ethoxy}-propionic acid from 3-(2-{2-[2-(2-methyl-amino-ethoxy)-ethoxy]-ethoxy}-ethoxy)-propionic acid sodium salt Trifluoroacetic acid anhydride (6 mL) is added to 3-(2-{2-[2-(2-methylamino-ethoxy)-ethoxy]-ethoxy}-ethoxy)-propionic acid sodium salt and the mixture is stirred at rt for 3 hours. The solvent is evaporated in vacuo. The residue is dissolved in acetonitrile:water (1:1) and applied to a reverse phase C18 column, 20-40 micron (150 g) and eluted with a gradient (5-95%) of acetonitrile (0.1% AcOH) in water (0.1% AcOH) and lyophilized to afford the product as a colorless oil, 0.383 g (92%, for 2 steps). MS (ESI+) m/z: 376.0 [MH$^+$]. MS (ESI-) m/z: 374.0 [M-H]$^-$. $^1$HNMR (300 MHz, CDCl$_3$) δ: 2.58-2.71 (2H, m), 3.13 and 3.22 (3H, each s), 3.63 (16H, m) and 3.76 (2H, t).

G. Synthesis of N-[6-(5,6-dihydro-11,12-didehydrobenzo[b,f]azocin-5-yl)-6-oxo-hexyl]-N-methyl-3-{2-[2-(2-{2-[methyl-(2,2,2-trifluoro-acetyl)-amino]-ethoxy}-ethoxy)-ethoxy]-ethoxy}-propionic acid from 1-(5,6-dihydro-11,12-didehydrobenzo[b,f]azocin-5-yl)-6-methylamino-hexan-1-one acetic acid salt and 3-{2-[2-(2-{2-[methyl-(2,2,2-trifluoro-acetyl)-amino]-ethoxy}-ethoxy)-ethoxy]-ethoxy}-propionic acid A solution of 1-(5,6-dihydro-11,12-didehydrobenzo[b,f]azocin-5-yl)-6-methylamino-hexan-1-one acetic acid salt (0.283 g, 0.721 mmol) in dichloromethane (20 mL) is washed with saturated aqueous sodium bicarbonate (20 mL) and dried over sodium sulfate. The solvent is evaporated in vacuo to afford the free base of 1-(5,6-dihydro-11,12-didehydrobenzo[b,f]azocin-5-yl)-6-methylamino-hexan-1-one, 0.22 g (92%), which is used in the subsequent step.

A solution of 3-{2-[2-(2-{2-[methyl-(2, 2, 2-trifluoro-acetyl)-amino]-ethoxy}-ethoxy)-ethoxy]-ethoxy}-propionic acid (0.248 g, 0.660 mmol) in DMF (4 mL) is treated with pentafluorophenyl diphenylphosphinate (0.305 g, 0.794 mmol) and N, N-diisopropylethylamine. The resultant solution is added to the free base of 1-(5,6-dihydro-11,12-didehydrobenzo[b,f]azocin-5-yl)-6-methylamino-hexan-1-one (0.22 g, 0.662 mmol) and stirred at rt for 20 hours. Water (1 mL) is added and the solution is applied to a reverse phase C18 column, 20-40 micron (150 g) and eluted with a gradient (30-95%) of acetonitrile (0.1% AcOH) in water (0.1% AcOH) and lyophilized to afford product as a colorless oil, 0.322 g (71%). MS (ESI+) m/z: 690.0 [MH$^+$] and 712.0 [MNa$^+$]. $^1$HNMR (300 MHz, CDCl$_3$) δ: 0.92-1.03 (2H, m), 1.26-1.34 (2H, m), 1.35-1.46 (2H, m), 1.87-1.97 (1H, m), 2.15-2.21 (1H, m), 2.50-2.57 (2H, m), 2.79 and 2.89 (together 3H, each s), 3.04-3.07 (1H, m), 3.10 and 3.21 (together 3H, each s), 3.14-3.19 (1H, m), 3.61-3.69 (17H, m), 3.73-3.77 (2H, m), 5.16 (1H, d of d), 7.22-7.43 (7H, m) and 7.70 (1H, d).

H. Synthesis of N-[6-(5,6-dihydro-11,12-didehydrobenzo[b,f]azocin-5-yl)-6-oxo-hexyl]-N-methyl-3-(2-{2-[2-(2-methylamino-ethoxy)-ethoxy]-ethoxy}-ethoxy)-propionamide from N-[6-(5,6-dihydro-11,12-didehydrobenzo[b,f]azocin-5-yl)-6-oxo-hexyl]-N-methyl-3-{2-[2-(2-{2-[methyl-(2,2,2-trifluoro-acetyl)-amino]-ethoxy}-ethoxy)-ethoxy]-ethoxy}-propionamide A solution of N-[6-(5,6-dihydro-11,12-didehydrobenzo[b,f]azocin-5-yl)-6-oxo-hexyl]-N-methyl-3-{2-[2-(2-{2-[methyl-(2,2,2-trifluoro-acetyl)-amino]-ethoxy}-ethoxy)-ethoxy]-ethoxy}-propionamide (0.322 g, 0.467 mmol) in methanol (10 mL) is treated with potassium carbonate (0.323 g, 2.33 mmol), and the mixture is stirred at rt for one day. An additional portion of potassium carbonate (0.323 g, 2.33 mmol) is added and stirring is continued for an additional day. The inorganics are removed by filtration, and the solvent is evaporated in vacuo. The residue is dissolved in acetonitrile/water (1/1) and applied to a reverse phase C18 column, 20-40 micron (150 g) and eluted with a gradient (5-95%) of acetonitrile (0.1% AcOH) in water (0.1% AcOH) and lyophilized to afford N-[6-(5,6-dihydro-11,12-didehydrobenzo[b,f]azocin-5-yl)-6-oxo-hexyl]-N-methyl-3-{2-[2-(2-{2-[methyl-(2,2,2-trifluoro-acetyl)-amino]-ethoxy}- ethoxy)-ethoxy]-ethoxy}-propionamide, 0.218 g (71%), and slightly impure product, 0.048 g (16%). MS (ESI+) m/z: 594.0 [MH⁺]. ¹H NMR (300 MHz, DMSO-d₆) δ: 0.85-0.90 (2H, m), 1.11-1.29 (4H, m), 1.75-1.86 (1H, m), 2.12-2.17 (1H, m), 2.27 (3H, m), 2.40 (1H, t), 2.46 (1H, t), 2.59 (2H, t), 2.66 and 2.80 (together 3H, each s), 2.98-3.09 (2H, m), 3.42-3.63 (17H, m), 5.04 (1H, d), 7.30-7.49 (6H, m), 7.57 (1H, d) and 7.63 (1H, d).

I. Synthesis of 6-Methylaminohexanoic Acid Hydrochloride from N-Methylcaprolactam A solution on N-methylcaprolactam (1.12 g, 8.81 mmol) in 5.3 mL of concentrated aqueous HCl and 6.7 mL water is refluxed for 19.5 hours. The reaction mixture is allowed to cool to room temperature, and 20 mL of water is added. It is then concentrated. 10 mL of water is added, and the mixture is again concentrated. The following is performed twice: 5 mL of acetone is then added and the mixture is concentrated. It is dried in vacuo to yield product (1.57 g, 98.1%, 8.64 mmol) as a cream-colored semi-solid. (45-149) MS m/z MH⁺ 146; ¹H NMR (300 MHz, DMSO-d₆) δ: 1.24-1.34 (2H, m), 1.44-1.62 (4H, m), 2.18-2.23 (2H, t), 2.77-2.86 (2H, m), 8.70 (2H, br), 12.05 (1H, s, br). (45-149-1 NMR)

J. Synthesis of 6-[Methyl-(2, 2, 2-trifluoroacetyl)-amino]hexanoic acid from 6-Methylaminohexanoic acid hydrochloride 6-Methylaminohexanoic acid hydrochloride (5.38 g, 29.6 mmol) is dissolved in 20 mL of methanol, and ethyl trifluoroacetate (4.4 mL, 5.3 g, 37 mmol) and triethylamine (8.3 mL, 6.0 g, 60 mmol) are added. The reaction mixture is stirred for 19.5 hours under argon at room temperature. 80 ml of 2M aqueous HCl is added, and the mixture is extracted with 3×60 mL ether. The combined organic layers are then washed with 100 mL brine, dried with anhydrous sodium sulfate, filtered, concentrated, and dried in vacuo to yield product as a clear, pale yellow syrup (6.86 g, 96.1%, 28.4 mmol). (53-15) MS m/z MH⁺ 242; ¹H NMR (300 MHz, DMSO-d₆) δ: 1.16-1.28 (2H, m), 1.45-1.60 (4H, m), 2.17-2.24 (2H, m), 2.94 (1H, s), 3.06-3.07 (2H, q), 3.32-3.39 (2H, m). (45-150-1 NMR)

K. Synthesis of 6-[Methyl-(2, 2, 2-trifluoroacetyl)-amino]-hexanoyl chloride from 6-[Methyl-(2, 2, 2-trifluoroacetyl)-amino]hexanoic acid A solution of 6-[Methyl-(2, 2, 2-trifluoroacetyl)-amino] hexanoic acid (6.84 g, 28.4 mmol) in methylene chloride (140 mL) under argon is chilled to 0° C. Oxalyl chloride (12 mL, 18 g, 142 mmol) is slowly added, and then 6 drops of DMF are added. The mixture is stirred at 0° C. for 1 hour and at room temperature for 1.5 hours. It is then concentrated and dried in vacuo to yield product as a light amber oil (6.54 g, 88.9%, 25.2 mmol). (53-16)

¹H NMR (300 MHz, CDCl₃) δ: 1.35-1.43 (2H, m), 1.57-1.81 (4H, m), 2.89-2.94 (2H, m), 3.02 (1H, s), 3.11-3.13 (2H, q), 3.37-3.46 (2H, m). (45-152-1 for NMR).

L. Synthesis of Dibenzo[a,d]cyclohepten-5-one oxime from Dibenzo[a,d]cyclohepten-5-one A solution of Dibenzo[a,d]cyclohepten-5-one (25.0 g, 121 mmol) and hydroxylamine HCl (12.6 g, 181 mmol) in pyridine (70 mL) is refluxed for 15.5 hours. The reaction mixture is allowed to cool to rt and concentrated in vacuo. The residue is partitioned between 5% aqueous HCl/ice (300 mL) and ethyl acetate (200 mL). The aqueous layer is twice extracted with ethyl acetate (150 mL). The organic layers are combined and washed with brine (250 mL) and dried over sodium sulfate. The solvent is evaporated in vacuo to afford product as a light yellow-beige solid, 26.8 g (100%). MS (ESI+) m/z: 222 [MH⁺]; MS (ESI−) m/z: 220 [M-H⁻]; ¹H NMR (300 MHz, CDCl₃) δ: 6.91-6.92 (2H, d), 7.33-7.43 (6H, m), 7.56-7.61 (1H, m), 7.65-7.68 (1H, m), 8.55 (1H, s).

M. dibenzo[a,d]cyclohepten-5-one oxime to 5,6-Dihydro-dibenzo[b,f]azocine

A solution of diisobutylaluminum hydride in dichloromethane (1.0 M, 192 mL) is cooled on a water bath and solid dibenzo[a,d]cyclohepten-5-one oxime (8.48 g, 38.3 mmol) is added in portions at a rate to maintain the temperature between 15-27° C. The water bath is removed and the resultant solution is stirred at rt for 3 days. The solution is cooled on a water bath and solid sodium sulfate decahydrate (20.4 g, 63.3 mmol) is added in portions at a rate to maintain the temperature between 12-30° C. Celite is added and the mixture is stirred at rt for 1 hour. The inorganics are separated by filtration and washed generously with ethyl acetate. The organic solutions are combined and the solvents are evaporated in vacuo. The residue is applied to a silica gel column (150 g) and eluted with a gradient of dichloromethane (20-100%) in hexanes to afford the product, 5.0 g (63%), as a yellow solid. MS m/z: 208.4 [MH⁺]; ¹HNMR (300 MHz, CDCl₃) δ: 4.29 (1H, br s), 4.59 (2H, s), 6.39 (1H, d), 6.50 (1H, d of d), 6.58 (1H, d), 6.61-6.66 (1H, m), 6.89-6.95 (1H, m), 7.00 (1H, d of d), 7.19-7.32 (4H, m).

N. Synthesis of N-[6-(6H-Dibenzo[b,f]azocin-5-yl)-6-oxo-hexyl]-2, 2, 2-trifluoro-N-methyl-acetamide from 5, 6-Dihydro-dibenzo[b,f]azocine (24) and 6-[Methyl-(2,2,2-trifluoroacetyl)-amino]-hexanoyl chloride Pyridine (3.6 mL, 3.5 g, 45 mmol) and 6-[Methyl-(2,2,2-trifluoroacetyl)-amino]-hexanoyl chloride (4.64 g, 17.9 mmol) in methylene chloride (8 mL) are added to a solution of N-[6-(6H-Dibenzo[b,f]azocin-5-yl)-6-oxo-hexyl]-2, 2, 2-trifluoro-N-methyl-acetamide (26a) from 5, 6-Dihydrodibenzo[b,f]azocine (3.11 g, 15.0 mmol) in methylene chloride (40 mL). The reaction mixture is stirred at room temperature under argon for 2.5 hours. It is then diluted with 150 mL of methylene chloride, and washed with 150 mL of water. The aqueous layer is extracted with 150 mL of methylene chloride. The combined organic layers are then washed with 150 mL brine, dried with anhydrous sodium sulfate, filtered and concentrated. The crude product is flash chromatographed (Isco) on a 220 g silica gel cartridge (Isco) with 0-50% ethyl acetate/hexane. After concentrating and drying in vacuo, the product is obtained as a thick yellow syrup. (5.64 g, 87.4%, 13.1 mmol). (53-36) MS m/z MH⁺ 431; ¹H NMR (300 MHz, DMSO-d₆) δ: 0.90-1.00 (2H, m), 1.26-1.40 (4H, m), 1.70-1.82 (1H, m), 1.88-1.98 (1H, m), 2.86 (1H, s), 2.99-3.01 (2H, q), 3.18-3.26 (2H, m), 4.12-4.18 (1H, dd), 5.32-5.39 (1H, dd), 6.61-6.66 (1H, dd), 6.73-6.79 (1H, dd), 7.13-7.20 (3H, m), 7.25-7.38 (5H, m). (53-6-1 for NMR).

O. Synthesis of N-[6-(11, 12-dibromo-11, 12-dihydro-6H-dibenzo[b,f]azocin-5-yl)-6-oxo-hexyl]-2, 2, 2-trifluoro-N-methyl-acetamide from N-[6-(6H-Dibenzo[b,f]azocin-5-yl)-6-oxo-hexyl]-2,2,2-trifluoro-N-methyl-acetamide Pyridinium tribromide (1.47 g, 4.60 mmol) is added to a solution of N-[6-(6H-Dibenzo[b,f]azocin-5-yl)-6-oxohexyl]-2,2,2-trifluoro-N-methyl-acetamide (1.80 g, 4.18 mmol) in methylene chloride (7.8 mL). The reaction mixture is stirred for about 3 hours. It is diluted with 100 mL of methylene chloride and washed with 2×55 mL 5% aqueous HCl. The organic layer is then washed with 55 mL of brine, dried with anhydrous sodium sulfate, filtered and concentrated. The crude product is flash chromatographed (Isco) on a 120 g silica cartridge (Isco Gold) with 0-50% ethyl acetate/hexane. It is concentrated and dried in vacuo to give the product as a white foam (1.93 g, 78.1%, 3.27 mmol). (53-21) MS m/z MH+ 591; $^1$H NMR (300 MHz, DMSO-d$_6$) δ: 1.10-1.19 (2H, m), 1.38-1.63 (4H, m), 2.02-2.33 (2H, m), 2.90 (1H, s), 3.02-3.03 (2H, d), 3.28-3.34 (2H, m), 4.18-5.09 (1H, m), 5.69-5.75 (1H, m), 5.81-5.87 (1H, t), 6.97-7.31 (7H, m), 7.55-7.65 (1H, m). (45-162-1 NMR)

P. Synthesis of N-[6-(5,6-dihydro-11,12-didehydrobenzo[b,f]azocin-5-yl)-6-oxo-hexyl]-2,2,2-trifluoro-N-methyl-acetamide from N-[6-(11,12-dibromo-11,12-dihydro-6H-dibenzo[b,f]azocin-5-yl)-6-oxo-hexyl]-2,2,2-trifluoro-N-methyl-acetamide A solution of potassium t-butoxide in THF (1.0 M, 5.3 mL, 5.3 mmol) is added dropwise to a solution of N-[6-(11,12-dibromo-11,12-dihydro-6H-dibenzo[b,f]azocin-5-yl)-6-oxo-hexyl]-2,2,2-trifluoro-N-methyl-acetamide (1.2 g, 2.03 mmol) in THF (15 mL), cooled on an ice bath, and stirred for 1 hour. The solution is diluted with ethyl acetate and slowly poured into 1N HCl with rapid stirring, cooled on an ice bath. The organic layer is separated and the aqueous layer is extracted with ethyl acetate. The combined organic phases is washed with brine and dried over sodium sulfate. The solvents are evaporated in vacuo, and the residue is applied to a silica gel column (40 g) and eluted with a gradient (20-80%) ethyl acetate in hexanes to yield product, 0.681 g (80%), as an amber oil. MS (ESI+) m/z: 429.2 [MH+]. $^1$H NMR (300 MHz, CDCl$_3$): 0.93-1.05 (2H, m), 1.31-1.48 (4H, m), 1.87-1.99 (1H, m), 2.15-2.24 (1H, m), 2.94 (3H, d), 3.14-3.27 (2H, m), 3.66 (1H, d of d), 5.16 (1H, d of d), 7.24-7.431 (7H, m) and 7.70 (1H, d).

Q. Synthesis of 1-(5,6-dihydro-11,12-didehydrobenzo[b,f]azocin-5-yl)-6-methylamino-hexan-1-one acetic acid salt (29a) from N-[6-(5,6-dihydro-11,12-didehydrobenzo[b,f]azocine)-6-oxo-hexyl]-2,2,2-trifluoro-N-methyl-acetamide (28a)

A solution of N-[6-(5,6-dihydro-11,12-didehydrobenzo[b,f]azocine)-6-oxo-hexyl]-2,2,2-trifluoro-N-methyl-acetamide (0.681 g, 1.61 mmol) in methanol (10 mL) is treated with potassium carbonate (0.67 g, 4.85 mmol) and water (1 mL) and stirred at rt for 18 hours. The solvent is evaporated in vacuo, and the residue is dissolved in dichloromethane and washed with water. The solvent is evaporated in vacuo, and the residue applied to a reverse phase C18 column, 20-40 micron (150 g) and eluted with a gradient (5-95%) of acetonitrile (0.1% AcOH) in water (0.1% AcOH). The solvents are removed by lyophilization to yield product, as the acetic acid salt, 0.533 g (84%), a sticky tan solid. MS (ESI+) m/z: 333.2 [MH+]. $^1$HNMR (300 MHz, DMSO-d$_6$) δ: 0.88-0.96 (2H, m), 1.11-1.28 (4H, m), 1.75-1.85 (1H, m) superimposed on 1.80 (3H, s), 2.07-2.18 (1H, m), 2.22 (3H, s), 2.31 (2H, t), 3.61 (1H, d), 5.04 (1H, d) and 7.28-7.64 (8H, m).

All publications and patents cited herein are incorporated by reference. Modifications and variations of the described compositions and methods are now apparent to those skilled in the art without departing from the scope and spirit of this disclosure. Although the invention has been described in connection with specific embodiments, it should be understood that the invention as claimed should not be limited to the specific embodiments. Indeed, modifications of the described compositions and modes for carrying out the invention, now apparent to those skilled in the art, in view of this disclosure, are intended to be within the scope of the claimed subject matter.

What is claimed is:
1. A compound of Formula I

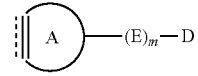

Formula I wherein
A is dibenzocyclooctynyl, cyclooct-4-ynoxyl, or (1R,8S,9S)-bicyclo[6.1.0]non-4-yn-9-ylmethyloxy;
D is a maytansinoid;
m is 1;
E is

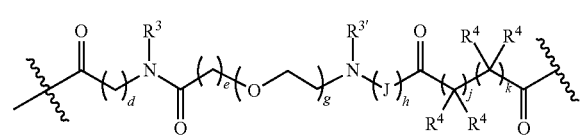

E4 wherein:
J is an amino acid or peptide;
h is an integer from 0 to 30;
d, e, g, j, and k are each independently an integer from 1 to 30;
each $R^4$ is independently H, alkyl, —N($R^3$)$_2$, —S$R^3$, and C1-C8 alkoxy, aryl;
each of $R^3$ or $R^{3'}$ is H, C1-C8 alkyl; and
"d is 5" and "$R^{3'}$ is H" are not satisfied simultaneously.
2. A compound of Formula I according to claim 1, wherein E4 is

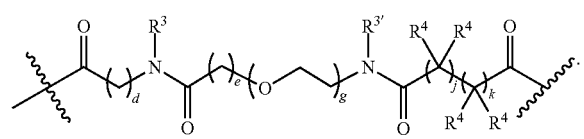

3. A compound of Formula I according to claim 2, wherein d is an integer from 1 to 5;
each $R^4$ is H.

4. A compound of Formula I according to claim 3 wherein each $R^3$ is H; and $R^{3'}$ is methyl.

5. A compound according to claim 4, wherein e is 2; g is 4; and j is 1 and k is 2, or j is 2 and k is 1.

6. A compound according to claim 1 wherein the maytansinoid is of the structure

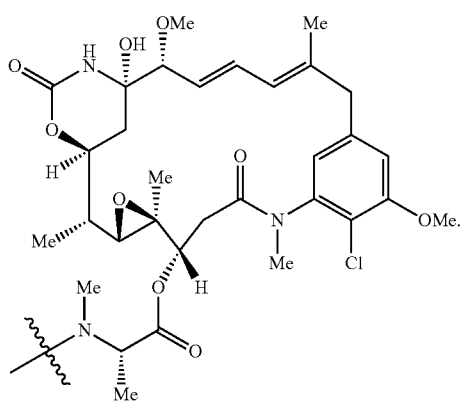

C2

7. A compound of Formula I according to claim 6, wherein E4 is

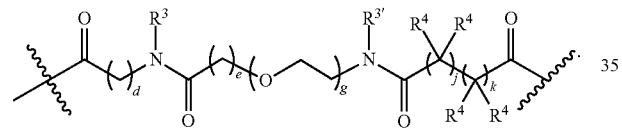

8. A compound of Formula I according to claim 7, wherein d is an integer from 1 to 5; each $R^4$ is H.

9. A compound of Formula I according to claim 8, wherein $R^3$ is hydrogen; and $R^{3'}$ is methyl.

10. A compound of Formula I according to claim 9, wherein e is 2; g is 4; and j is 1 and k is 2, or j is 2 and k is 1.

11. A compound of Formula I according to claim 10, wherein d is 2.

12. A compound of Formula I

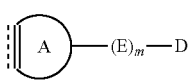

Formula I wherein
A is

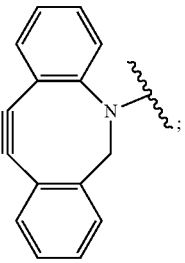 [SMILES: *N1Cc2ccccc2C#Cc2ccccc21]

D is

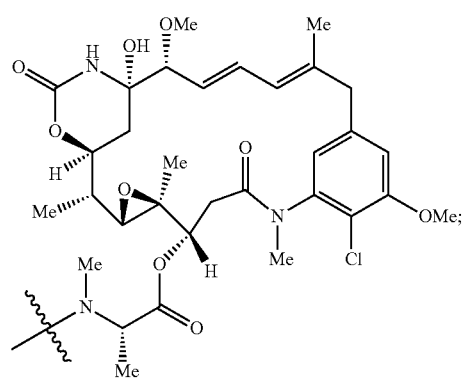 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

E is

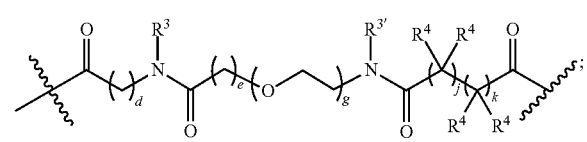

m is 1;
d is an integer from 1 to 3;
e, g, j, and k are each independently an integer from 1 to 5;
each $R^4$ is independently H, alkyl, —$N(R^3)_2$, —$SR^3$, and C1-C8 alkoxy, aryl;
each of $R^3$ or $R^{3'}$ is H, C1-C8 alkyl.

13. A compound according to claim 12, wherein each $R^4$ is H.

14. A compound according to claim 13, wherein $R^3$ is H; and $R^{3'}$ is methyl.

15. A compound according to claim 14, wherein e is 2; g is 4; and j is 1 and k is 2, or j is 2 and k is 1.

16. A compound of Formula I according to claim 15, wherein d is 2.

* * * * *